(12) United States Patent
Sokoloff et al.

(10) Patent No.: US 11,767,353 B2
(45) Date of Patent: Sep. 26, 2023

(54) TRAIL COMPOSITIONS WITH REDUCED IMMUNOGENICITY

(71) Applicant: Theraly Fibrosis, Inc., Gaithersburg, MD (US)

(72) Inventors: Alex Sokoloff, Madison, WI (US); Viktor Roschke, Bethesda, MD (US); Kang Choon Lee, Seoul (KR); Seulki Lee, Ellicott City, MD (US); Yumin Oh, Clarksville, MD (US)

(73) Assignee: THERALY FIBROSIS, INC., Gaithersburg, MD (US)

( * ) Notice: Subject to any disclaimer, the term of this patent is extended or adjusted under 35 U.S.C. 154(b) by 0 days.

(21) Appl. No.: 17/223,283

(22) Filed: Apr. 6, 2021

(65) Prior Publication Data

US 2021/0380653 A1    Dec. 9, 2021

Related U.S. Application Data

(60) Provisional application No. 63/035,472, filed on Jun. 5, 2020.

(51) Int. Cl.
| | | |
|---|---|---|
| *C07K 14/47* | (2006.01) | |
| *A61K 45/06* | (2006.01) | |
| *A61P 35/00* | (2006.01) | |
| *A61K 47/65* | (2017.01) | |
| *A61K 47/60* | (2017.01) | |
| *C07K 14/705* | (2006.01) | |
| *A61K 38/00* | (2006.01) | |

(52) U.S. Cl.
CPC .......... *C07K 14/4703* (2013.01); *A61K 45/06* (2013.01); *A61K 47/60* (2017.08); *A61K 47/65* (2017.08); *A61P 35/00* (2018.01); *C07K 14/70575* (2013.01); *A61K 38/00* (2013.01); *C07K 2319/00* (2013.01); *C07K 2319/21* (2013.01); *C07K 2319/73* (2013.01)

(58) Field of Classification Search
None
See application file for complete search history.

(56) References Cited

U.S. PATENT DOCUMENTS

| | | |
|---|---|---|
| 6,261,801 B1 | 7/2001 | Wei |
| 6,747,126 B1 * | 6/2004 | Eckert .................. C07K 14/005 424/188.1 |
| 6,908,963 B2 | 6/2005 | Roberts |
| 7,056,698 B2 | 6/2006 | Levitt |
| 7,060,272 B2 | 6/2006 | Jian |
| 7,160,924 B2 | 1/2007 | Kinstler |
| 7,368,295 B2 | 5/2008 | Tovar |
| 7,411,051 B2 | 8/2008 | Rosen |
| 7,521,056 B2 | 4/2009 | Chang |
| 7,534,866 B2 | 5/2009 | Chang |
| 7,550,143 B2 | 6/2009 | Chang |
| 7,615,233 B2 | 11/2009 | Yano |
| 7,795,404 B1 | 9/2010 | Lin |
| 7,906,118 B2 | 3/2011 | Chang |
| 7,994,281 B2 | 8/2011 | Tur |
| 8,003,111 B2 | 8/2011 | Chang |
| 8,034,352 B2 | 10/2011 | Chang |
| 8,075,916 B2 | 12/2011 | Song |
| 8,114,845 B2 | 2/2012 | Langermann |
| 8,143,380 B2 | 3/2012 | Walker |
| 8,158,129 B2 | 4/2012 | Chang |
| 8,282,934 B2 | 10/2012 | Chang |
| 8,287,888 B2 | 10/2012 | Song |
| 8,435,540 B2 | 5/2013 | Chang |
| 8,440,787 B2 | 5/2013 | McManus |
| 8,586,020 B2 | 11/2013 | Song |
| 8,597,659 B2 | 12/2013 | Chang |
| 8,609,089 B2 | 12/2013 | Langermann |
| 8,628,801 B2 | 1/2014 | Garreta |
| 8,673,923 B2 | 3/2014 | El-Deiry |
| 8,709,416 B2 | 4/2014 | Langermann |
| 9,017,726 B2 | 4/2015 | Song |
| 9,102,735 B2 | 8/2015 | Govindan |

(Continued)

FOREIGN PATENT DOCUMENTS

| | | | | |
|---|---|---|---|---|
| KR | 20150086021 A * | 2/2016 | | |
| WO | 2003/099196 | 5/2003 | | |
| WO | 2003099196 | 5/2003 | | |
| WO | WO-2005002500 A2 * | 1/2005 | .......... | C07K 14/005 |
| WO | 2006/107617 | 10/2006 | | |
| WO | 2006/107786 | 10/2006 | | |
| WO | 2006107617 | 10/2006 | | |
| WO | 2006107786 | 10/2006 | | |
| WO | 2006/133396 | 12/2006 | | |
| WO | 2006133396 | 12/2006 | | |
| WO | 2007/005874 | 1/2007 | | |
| WO | 2007005874 | 1/2007 | | |

(Continued)

OTHER PUBLICATIONS

Machine translation of KR20150086021A dowloaded from Google Patents on Sep. 7, 2022 (Year: 2022).*

(Continued)

*Primary Examiner* — Christina Bradley
(74) *Attorney, Agent, or Firm* — PABST PATENT GROUP LLP

(57) ABSTRACT

Fusion polypeptides with modified multimerization domains that provide high expression, solubility, stability, and low immunogenicity to the fusion polypeptides have been developed. TRAIL compositions with the modified multimerization domains show improved physico-chemical and biological properties relative to TRAIL compositions with unmodified multimerization domains. The TRAIL compositions also have lower immunogenicity in the mammalian host when compared to that of TRAIL compositions with unmodified multimerization domains. The TRAIL compositions induce apoptosis of cancer cells and cancer-associated fibroblasts in vivo, reducing tumor size.

35 Claims, 19 Drawing Sheets

Specification includes a Sequence Listing.

(56) References Cited

U.S. PATENT DOCUMENTS

| | | | |
|---|---|---|---|
| 9,150,846 | B2 | 10/2015 | Jefferies |
| 9,321,825 | B2 * | 4/2016 | Lee .................. A61P 37/00 |
| 2004/0186051 | A1 | 9/2004 | Kelley |
| 2006/0099203 | A1 | 5/2006 | Pease |
| 2006/0110383 | A1 | 5/2006 | Honjo |
| 2006/0188498 | A1 | 8/2006 | Ashkenazi |
| 2007/0166281 | A1 | 7/2007 | Kosak |
| 2008/0044421 | A1 | 2/2008 | Ashkenazi |
| 2008/0199423 | A1 | 8/2008 | Godowski |
| 2008/0305038 | A1 | 12/2008 | Rosenecker |
| 2009/0022683 | A1 | 1/2009 | Song |
| 2009/0081157 | A1 | 3/2009 | Kornbluth |
| 2009/0203599 | A1 | 8/2009 | Lee |
| 2009/0258017 | A1 | 10/2009 | Callahan |
| 2009/0325867 | A1 | 12/2009 | Cohen |
| 2010/0209490 | A1 | 8/2010 | Morita |
| 2010/0239554 | A1 | 9/2010 | Schellenberger |
| 2011/0020273 | A1 | 1/2011 | Chang |
| 2011/0104103 | A1 | 5/2011 | Heetebrij |
| 2013/0079280 | A1 | 3/2013 | Baca |
| 2013/0178416 | A1 | 7/2013 | Chilkoti |
| 2013/0217091 | A1 | 8/2013 | Chang |
| 2014/0004081 | A1 | 1/2014 | Cobbold |
| 2014/0079722 | A1 | 3/2014 | Prudent |
| 2014/0086907 | A1 | 3/2014 | Shah |
| 2014/0096274 | A1 | 4/2014 | Quax |
| 2014/0161766 | A1 | 6/2014 | Chang |
| 2015/0056159 | A1 | 2/2015 | Kontermann |
| 2015/0174269 | A1 | 6/2015 | Govindan |
| 2015/0183875 | A1 | 7/2015 | Cobbold |
| 2015/0218282 | A1 | 8/2015 | Shah |
| 2015/0250896 | A1 | 9/2015 | Zhao |
| 2015/0259397 | A1 | 9/2015 | Lee |
| 2015/0284416 | A1 | 10/2015 | Zhao |
| 2015/0301058 | A1 | 10/2015 | Schettini |
| 2016/0280761 | A1 | 9/2016 | Rozanov |

FOREIGN PATENT DOCUMENTS

| | | |
|---|---|---|
| WO | 2007/046893 | 4/2007 |
| WO | 2007046893 | 4/2007 |
| WO | 2009/058379 | 5/2009 |
| WO | 2009/126558 | 5/2009 |
| WO | 2009058379 | 5/2009 |
| WO | 2009126558 | 5/2009 |
| WO | 2010/093395 | 8/2010 |
| WO | 2010093395 | 8/2010 |
| WO | 2011/025904 | 3/2011 |
| WO | 2011025904 | 3/2011 |
| WO | 2014/126537 | 8/2014 |
| WO | 2014126537 | 8/2014 |
| WO | 2015/010615 | 1/2015 |
| WO | 2015010615 | 1/2015 |
| WO | 2015/028850 | 3/2015 |
| WO | 2015/037000 | 3/2015 |
| WO | 2015028850 | 3/2015 |
| WO | 2015037000 | 3/2015 |
| WO | 2015/127685 | 9/2015 |
| WO | 2015127685 | 9/2015 |
| WO | 2016/160576 | 10/2016 |
| WO | 2016160576 | 10/2016 |

OTHER PUBLICATIONS

Amiram, et al., "Injectable protease-operated depots of glucagon-like peptide-1 provide extended and tunable glucose control", PNAS, 110(8):2792-2792 (2013).

Audo, et al., "Mechanisms and clinical relevance of TRAIL-triggered responses in the synovial fibroblasts of patients with rheumatoid arthritis", Arthritis and Rheumatism, 63(4):904-913 (2011).

Audo, et al., "The two directions of TNF-related apoptosis-inducing ligand in rheumatoid arthritis", Cytokine, 63(2):81-90 (2013).

Benedict, et al., "TRAIL: not just for tumors anymore?", J. Exp. Med., 209(11):1903-1906 (2012).

Berger, et al., "Phase I safety and pharmacokinetic study of CT-011, a humanized antibody interacting with PD-1, in patients with advanced hematologic malignancies", Clin. Cancer Res., 14(10):3044-51 (2008).

Brocchini, et al., "PEGylation of native disulfide bonds in proteins", Nature protocols, 1(5):2241-2252 (2006).

Bryson, et al., "Prediction of immunogenicity of therapeutic proteins: Validity of Computational Tools", Biodrugs, 24(1):1-8 (2010).

Butte, et al., "Programmed Death-1 Ligand 1 Interacts Specifically with the B7-1 Costimulatory Molecule to Inhibit T Cell Responses", Immunity, 27(1): 111-122 (2007).

Carillo, et al., "The Multiple Sequence Alignment Problem in Biology", SIAM J Applied Math., 48(5):1073-1082 (1988).

Chae, et al., "Improved Antitumor Activity and Tumor Targeting of NH2-Terminal-Specific PEGylated Tumor Necrosis Factor-Related Apoptosis-Inducing Ligand", Molecular Cancer Therapeutics, 9(6):1719-29 (2010).

Cong, et al., "Site-specific PEGylation at histidine tags", Bioconjugate Chemistry, 23(2):248-263 (2012).

Cubillos-Ruiz, et al., "Polyethylenimine-based siRNA nanocomplexes reprogram tumor-associated dendritic cells via TLR5 to elicit therapeutic antitumor immunity", J. Clin. Invest. 119(8):2231-2244 (2009).

Database Genesq Online, "ILz(6)-TRAIL fusion protein, Seq ID 13", retrieved from EBI accession No. BCD92582 (Oct. 22, 2015).

Di Modugno, et al., "3D models in the new era of immune oncology: focus on T cells, CAF and ECM", Journal of Experimental and Clinical Cancer Research, 38:117 (2019).

Erbe, et al., "Small molecule ligands define a binding site on the immune regulatory protein B7.1 ", J. Biol. Chem., 277(9):7363-7368 (2002).

Fee, "Size comparison between proteins PEGylated with branched and linear poly(ethylene glycol) molecules", Biotechnol Bioeng., 98(4):725-3 (2007).

Freeman, "Structures of PD-1 with its ligands: Sideways and dancing cheek to cheek" PNAS, 105:10275-10276 (2008).

Gong, et al., "Site-specific PEGylation of exenatide analogues markedly improved their glucoregulatory activity", British Journal of Pharmacology, 163(2):399-412 (2011).

Han, et al., "PD-1/PD-L1 pathway: current researches in cancer", Am. J. Cancer Res., 10(3)L727-742 (2020).

Harbury, et al., "Crystal structure of an isoleucine-zipper trimer", Nature, 371 (6492):80-83 (1994).

Hooge, et al., "Soluble TRAIL concentrations are raised in patients with systemic lupus erythematosus", Ann. Rheum. Dis., 64(6):854-858 (2005).

Huang, et al., "Parallelization of a local similarity algorithm", Computer App Biosci., 8(2):155-165 (1992).

Kim, et al., "The secretable form of trimeric TRAI, a potent inducer of apoptosis", Biochem. and Biophys. Res. Communications, 321(4):930-935 (2004).

Kim, et al., "PEGylated TNF-Related Apoptosis-Inducing Ligand (TRAIL) Analogues: Pharmacokinetics and Antitumor Effects", Bioconjugate Chem., 22 (8):1631-1637 (2011).

Kim, et al., "Ionic complex systems based on hyaluronic acid and PEGylated TNF-related apoptosis-inducing ligand for treatment of rheumatoid arthritis", Biomaterials, 31(34):9057-64 (2010).

Kim, et al., "A sulfate polysaccharide/TNF-related apoptosis-inducing ligand (TRAIL) complex for the long-term delivery of TRAIL in poly(lactic-co-glycolicacid) (PLGA) microspheres", Journal of Pharmacy and Pharmacology, 65(1):11-21 (2013).

Klener, et al., "Immunotherapy Approaches in Cancer Treatment", Current Pharmaceutical Biotechnology, 16(9):771-781 (2015).

Lamhamedi-Cherradi, et al., "Critical Roles of Tumor Necrosis Factor-Related Apoptosis-Inducing Ligand in Type 1 Diabetes", Diabetes, 52(9):2274-2278 (2003).

Molineux, "The design and development of pegfilgrastim (PEG-rmetHuG-CSF, Neulasta)", Current pharmaceutical design, 10(11):1235-1244 (2004).

(56) References Cited

OTHER PUBLICATIONS

Molnar, et al., "Crystal structure of the complex between programmed death-1 (PD-1) and its ligand PD-L2", PNAS, 105(30):10483-10488 (2008).
Needleman, et al., "A general method applicable to the search for similarities in the amino acid sequence of two proteins", J. Mol. Biol., 48(3):443-453 (1970).
Oh, et al., "Systemic PEGylated TRAIL Treatment Ameliorates Liver Cirrhosis in Rats by Eliminating Activated Hepatic Stellate Cells", Hepatology, 64(1):209-223 (2016).
Oshaben, et al., "The Native GCN4 Leucine-Zipper Domain Does Not Uniquely Specify a Dimeric Oligomerization State", Biochemistry, 51(47):9581-9591 (2012).
Park, et al., "Targeting of dermal myofibroblasts through death receptor 5 arrests fibrosis in mouse models of scleroderma", Nat. Comm., 10(1):1128 (2019).
Rozanov, et al., "Engineering a leucine zipper-TRAIL homotrimer with improved cytotoxicity in tumor cells", Mol. Cancer Ther., 8(6):1515-1525 (2009).
Rozanov, et al., "A Humanized Leucine Zipper-TRAIL Hybrid Induces Apoptosis of Tumors both In Vitro and In Vivo", PLoS One, 10(4):e0122980 (2015).
Sammartino, et al., "Anti-GBM disease following CTLA4 blockade in a patient with metastatic melanoma", NDT Plus, 3(2):135-137 (2010).
Sliepen, et al., "Immunosilencing a Highly Immunogenic Protein Trimerization Domain", J of Biological Chemistry, 290(12):7436-7442 (2015).
Tur, "DR4-selective tumor necrosis factor-related apoptosis-inducing ligand (TRAIL) variants obtained by structure-based design", Biological Chemistry, 283(29):20560-8 (2008).
Van Der Sloot, et al., "Designed tumor necrosis factor-related apoptosis-inducing ligand variants initiating apoptosis exclusively via the DR5 receptor", PNAS, 103(23):8634-9 (2006).
Walczak, et al., "Tumoricidal activity of tumor necrosis factor-related apoptosis-inducing ligand in vivo", Nature Medicine, 5(2):157-163 (1999).
Weiner, "Cancer immunology for the clinician", Clinical Advances in Hematology & Oncology, 13(5):299-306 (2015).
Wu, et al., "TRAIL and chemotherapeutic drugs in cancer therapy", Vitam. Horm., 67:365-83 (2004).
Xiang, et al., "Tissue distribution, stability, and pharmacokinetics of Apo2 ligand/tumor necrosis factor-related apoptosis-inducing ligand in human colon carcinoma COLO205 tumor-bearing nude mice", Drug Metabolism and Disposition, 32(11):1230-1238 (2004).
Yang, et al., "Target specific hyaluronic acid—interferon alpha conjugate for the treatment of hepatitis C virus infection", Biomaterials, 32(33):8722-8729 (2011).
Zheng, et al., "Critical roles of TRAIL in hepatic cell death and hepatic inflammation", J. Clin. Invest., 113(1):58-64 (2004).
International Search Report for PCT/US2021/035997 dated Oct. 21, 2021.
Han, et al., "PD-1/PD-L1 pathway: current researches in cancer", Am. J. Cancer Res., 10(3):727-742 (2020).
Keener, et al., "Immunotherapy Approaches in Cancer Treatment", Current Pharmaceutical Biotechnology, 16(9):771-781 (2015).
Lamhamedi-Chfrradi, et al., "Critical Roles of Tumor Necrosis Factor-Related Apoptosis-Inducing Ligand in Type 1 Diabetes", Diabetes, 52(9):2274-2278 (2003).

* cited by examiner

| Position | 1 | 2 | 3 | 4 | 5 | 6 | 7 | 8 | 9 | # | # | # | # | # | # | # | # | 20 | # | # | # | 27 | # | # | # | # | # | # | # | # | # | # | # | Total score |
|---|---|---|---|---|---|---|---|---|---|---|---|---|---|---|---|---|---|---|---|---|---|---|---|---|---|---|---|---|---|---|---|---|---|---|
| SEQ ID 3 | P | G | M | C | G | G | K | Q | I | E | D | K | H | E | I | L | S | K | Y | H | I | E | I | A | R | I | K | L | I | G | E | D | G | V | |
| IG score | | | | | | | | | | | | | | | 4 | | | 14 | | 2 | 24 | | 2 | | | | | | | | | | | 50 |
| SEQ ID 6 | M | G | R | M | K | Q | I | E | D | K | H | E | I | L | S | K | Y | H | I | E | I | A | R | I | K | E | L | I | G | E | D | G | V | |
| IG score | | | | | | | | | | | | | | 4 | | | 14 | | 2 | 0 | | 2 | | | 0 | | | | | | | | 24 |
| SEQ ID 7 | M | G | R | M | K | Q | I | E | D | K | H | E | I | L | S | K | Y | H | I | E | N | I | A | R | I | K | Q | L | I | G | E | D | G | V | |
| IG score | | | | | | | | | | | | | | | 4 | | | 14 | | 2 | 7 | | 2 | | | | | | | | | | | 33 |
| SEQ ID 8 | M | G | R | M | K | Q | I | E | D | K | H | E | I | L | S | K | Y | H | V | E | N | I | A | R | I | K | Q | L | I | G | E | D | G | V | |
| IG score | | | | | | | | | | | | | | | 4 | | | 7 | | 2 | 7 | | 2 | | | | | | | | | | | 24 |
| SEQ ID 4 | M | G | R | M | K | Q | I | E | D | K | H | E | I | L | S | K | Y | H | V | E | N | I | A | R | I | K | E | L | I | G | E | D | G | V | |
| IG score | | | | | | | | | | | | | | | 4 | | | 7 | | 2 | 0 | | 2 | | | 0 | | | | | | | | 15 |

FIG. 6

TLY012: 30 ng/ml for 3 hours
Gemcitabine 50 µM for 24 hours
Doxorubicin 10 µM for 24 hours
Cisplatin 50 µM for 24 hours
5-FU 25 µg/mL for 24 hours
Irinotecan 10 µM for 24 hours

SEQUENCE LISTING

<160> NUMBER OF SEQ ID NOS: 56

<210> SEQ ID NO 1
<211> LENGTH: 30
<212> TYPE: PRT
<213> ORGANISM: Artificial Sequence
<220> FEATURE:
<223> OTHER INFORMATION: Synthetic Peptide

```
<400> SEQUENCE: 1

Lys Gln Ile Glu Asp Lys Ile Glu Glu Ile Leu Ser Lys Ile Tyr His
1               5                   10                  15

Ile Glu Asn Glu Ile Ala Arg Ile Lys Lys Leu Ile Gly Glu
            20                  25                  30

<210> SEQ ID NO 2
<211> LENGTH: 34
<212> TYPE: PRT
<213> ORGANISM: Artificial Sequence
<220> FEATURE:
<223> OTHER INFORMATION: Synthetic Peptide

<400> SEQUENCE: 2

Gly Arg Met Lys Gln Ile Glu Asp Lys Ile Glu Glu Ile Leu Ser Lys
1               5                   10                  15

Ile Tyr His Ile Glu Asn Glu Ile Ala Arg Ile Lys Lys Leu Ile Gly
            20                  25                  30

Glu Arg

<210> SEQ ID NO 3
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 3

Pro Gly Met Cys Gly Gly Lys Gln Ile Glu Asp Lys Ile Glu Glu Ile
1               5                   10                  15

Leu Ser Lys Ile Tyr His Ile Glu Asn Glu Ile Ala Arg Ile Lys Lys
            20                  25                  30

Leu Ile Gly Glu Asp Gly Val
        35

<210> SEQ ID NO 4
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 4

Lys Gln Ile Glu Asp Lys Ile Glu Glu Ile Leu Ser Lys Ile Tyr His
1               5                   10                  15

Val Glu Asn Glu Ile Ala Arg Ile Lys Glu Leu Ile Gly Glu
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 5

Lys Gln Ile Glu Asp Lys Ile Glu Glu Ile Leu Ser Lys Ile Tyr His
1               5                   10                  15

Val Glu Asn Glu Ile Ala Arg Ile Lys Lys Leu Ile Gly Glu
            20                  25                  30
```

<210> SEQ ID NO 6
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 6

Lys Gln Ile Glu Asp Lys Ile Glu Glu Ile Leu Ser Lys Ile Tyr His
1               5                   10                  15

Ile Glu Asn Glu Ile Ala Arg Ile Lys Glu Leu Ile Gly Glu
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 7

Lys Gln Ile Glu Asp Lys Ile Glu Glu Ile Leu Ser Lys Ile Tyr His
1               5                   10                  15

Ile Glu Asn Glu Ile Ala Arg Ile Lys Gln Leu Ile Gly Glu
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 8

Lys Gln Ile Glu Asp Lys Ile Glu Glu Ile Leu Ser Lys Val Tyr His
1               5                   10                  15

Ile Glu Asn Glu Ile Ala Arg Ile Lys Glu Leu Ile Gly Glu
            20                  25                  30

<210> SEQ ID NO 9
<211> LENGTH: 281
<212> TYPE: PRT
<213> ORGANISM: Homo sapiens

<400> SEQUENCE: 9

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

```
Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
                180                 185                 190

Gln Glu Glu Ile Lys Glu Asn Thr Lys Asn Asp Lys Gln Met Val Gln
                195                 200                 205

Tyr Ile Tyr Lys Tyr Thr Ser Tyr Pro Asp Pro Ile Leu Leu Met Lys
210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
                260                 265                 270

Ser Phe Phe Gly Ala Phe Leu Val Gly
                275                 280

<210> SEQ ID NO 10
<211> LENGTH: 243
<212> TYPE: PRT
<213> ORGANISM: Homo sapiens

<400> SEQUENCE: 10

Thr Asn Glu Leu Lys Gln Met Gln Asp Lys Tyr Ser Lys Ser Gly Ile
1               5                   10                  15

Ala Cys Phe Leu Lys Glu Asp Asp Ser Tyr Trp Asp Pro Asn Asp Glu
                20                  25                  30

Glu Ser Met Asn Ser Pro Cys Trp Gln Val Lys Trp Gln Leu Arg Gln
                35                  40                  45

Leu Val Arg Lys Met Ile Leu Arg Thr Ser Glu Glu Thr Ile Ser Thr
50                  55                  60

Val Gln Glu Lys Gln Gln Asn Ile Ser Pro Leu Val Arg Glu Arg Gly
65                  70                  75                  80

Pro Gln Arg Val Ala Ala His Ile Thr Gly Thr Arg Gly Arg Ser Asn
                85                  90                  95

Thr Leu Ser Ser Pro Asn Ser Lys Asn Glu Lys Ala Leu Gly Arg Lys
                100                 105                 110

Ile Asn Ser Trp Glu Ser Ser Arg Ser Gly His Ser Phe Leu Ser Asn
                115                 120                 125

Leu His Leu Arg Asn Gly Glu Leu Val Ile His Glu Lys Gly Phe Tyr
130                 135                 140

Tyr Ile Tyr Ser Gln Thr Tyr Phe Arg Phe Gln Glu Glu Ile Lys Glu
145                 150                 155                 160

Asn Thr Lys Asn Asp Lys Gln Met Val Gln Tyr Ile Tyr Lys Tyr Thr
                165                 170                 175

Ser Tyr Pro Asp Pro Ile Leu Leu Met Lys Ser Ala Arg Asn Ser Cys
                180                 185                 190

Trp Ser Lys Asp Ala Glu Tyr Gly Leu Tyr Ser Ile Tyr Gln Gly Gly
                195                 200                 205

Ile Phe Glu Leu Lys Glu Asn Asp Arg Ile Phe Val Ser Val Thr Asn
210                 215                 220
```

Glu His Leu Ile Asp Met Asp His Glu Ala Ser Phe Phe Gly Ala Phe
225                 230                 235                 240

Leu Val Gly

<210> SEQ ID NO 11
<211> LENGTH: 241
<212> TYPE: PRT
<213> ORGANISM: Homo sapiens

<400> SEQUENCE: 11

Glu Leu Lys Gln Met Gln Asp Lys Tyr Ser Lys Ser Gly Ile Ala Cys
1               5                   10                  15

Phe Leu Lys Glu Asp Asp Ser Tyr Trp Asp Pro Asn Asp Glu Glu Ser
            20                  25                  30

Met Asn Ser Pro Cys Trp Gln Val Lys Trp Gln Leu Arg Gln Leu Val
        35                  40                  45

Arg Lys Met Ile Leu Arg Thr Ser Glu Glu Thr Ile Ser Thr Val Gln
50                  55                  60

Glu Lys Gln Gln Asn Ile Ser Pro Leu Val Arg Glu Arg Gly Pro Gln
65                  70                  75                  80

Arg Val Ala Ala His Ile Thr Gly Thr Arg Gly Arg Ser Asn Thr Leu
                85                  90                  95

Ser Ser Pro Asn Ser Lys Asn Glu Lys Ala Leu Gly Arg Lys Ile Asn
            100                 105                 110

Ser Trp Glu Ser Ser Arg Ser Gly His Ser Phe Leu Ser Asn Leu His
        115                 120                 125

Leu Arg Asn Gly Glu Leu Val Ile His Glu Lys Gly Phe Tyr Tyr Ile
130                 135                 140

Tyr Ser Gln Thr Tyr Phe Arg Phe Gln Glu Glu Ile Lys Glu Asn Thr
145                 150                 155                 160

Lys Asn Asp Lys Gln Met Val Gln Tyr Ile Tyr Lys Tyr Thr Ser Tyr
                165                 170                 175

Pro Asp Pro Ile Leu Leu Met Lys Ser Ala Arg Asn Ser Cys Trp Ser
            180                 185                 190

Lys Asp Ala Glu Tyr Gly Leu Tyr Ser Ile Tyr Gln Gly Gly Ile Phe
        195                 200                 205

Glu Leu Lys Glu Asn Asp Arg Ile Phe Val Ser Val Thr Asn Glu His
210                 215                 220

Leu Ile Asp Met Asp His Glu Ala Ser Phe Phe Gly Ala Phe Leu Val
225                 230                 235                 240

Gly

<210> SEQ ID NO 12
<211> LENGTH: 191
<212> TYPE: PRT
<213> ORGANISM: Homo sapiens

<400> SEQUENCE: 12

Met Ile Leu Arg Thr Ser Glu Glu Thr Ile Ser Thr Val Gln Glu Lys
1               5                   10                  15

Gln Gln Asn Ile Ser Pro Leu Val Arg Glu Arg Gly Pro Gln Arg Val
            20                  25                  30

Ala Ala His Ile Thr Gly Thr Arg Gly Arg Ser Asn Thr Leu Ser Ser
        35                  40                  45

Pro Asn Ser Lys Asn Glu Lys Ala Leu Gly Arg Lys Ile Asn Ser Trp

```
            50                  55                  60
Glu Ser Ser Arg Ser Gly His Ser Phe Leu Ser Asn Leu His Leu Arg
 65                  70                  75                  80

Asn Gly Glu Leu Val Ile His Glu Lys Gly Phe Tyr Tyr Ile Tyr Ser
                 85                  90                  95

Gln Thr Tyr Phe Arg Phe Gln Glu Glu Ile Lys Glu Asn Thr Lys Asn
            100                 105                 110

Asp Lys Gln Met Val Gln Tyr Ile Tyr Lys Tyr Thr Ser Tyr Pro Asp
        115                 120                 125

Pro Ile Leu Leu Met Lys Ser Ala Arg Asn Ser Cys Trp Ser Lys Asp
    130                 135                 140

Ala Glu Tyr Gly Leu Tyr Ser Ile Tyr Gln Gly Gly Ile Phe Glu Leu
145                 150                 155                 160

Lys Glu Asn Asp Arg Ile Phe Val Ser Val Thr Asn Glu His Leu Ile
                165                 170                 175

Asp Met Asp His Glu Ala Ser Phe Phe Gly Ala Phe Leu Val Gly
            180                 185                 190

<210> SEQ ID NO 13
<211> LENGTH: 190
<212> TYPE: PRT
<213> ORGANISM: Homo sapiens

<400> SEQUENCE: 13

Ile Leu Arg Thr Ser Glu Glu Thr Ile Ser Thr Val Gln Glu Lys Gln
  1               5                  10                  15

Gln Asn Ile Ser Pro Leu Val Arg Glu Arg Gly Pro Gln Arg Val Ala
             20                  25                  30

Ala His Ile Thr Gly Thr Arg Gly Arg Ser Asn Thr Leu Ser Ser Pro
         35                  40                  45

Asn Ser Lys Asn Glu Lys Ala Leu Gly Arg Lys Ile Asn Ser Trp Glu
     50                  55                  60

Ser Ser Arg Ser Gly His Ser Phe Leu Ser Asn Leu His Leu Arg Asn
 65                  70                  75                  80

Gly Glu Leu Val Ile His Glu Lys Gly Phe Tyr Tyr Ile Tyr Ser Gln
                 85                  90                  95

Thr Tyr Phe Arg Phe Gln Glu Glu Ile Lys Glu Asn Thr Lys Asn Asp
            100                 105                 110

Lys Gln Met Val Gln Tyr Ile Tyr Lys Tyr Thr Ser Tyr Pro Asp Pro
        115                 120                 125

Ile Leu Leu Met Lys Ser Ala Arg Asn Ser Cys Trp Ser Lys Asp Ala
    130                 135                 140

Glu Tyr Gly Leu Tyr Ser Ile Tyr Gln Gly Gly Ile Phe Glu Leu Lys
145                 150                 155                 160

Glu Asn Asp Arg Ile Phe Val Ser Val Thr Asn Glu His Leu Ile Asp
                165                 170                 175

Met Asp His Glu Ala Ser Phe Phe Gly Ala Phe Leu Val Gly
            180                 185                 190

<210> SEQ ID NO 14
<211> LENGTH: 187
<212> TYPE: PRT
<213> ORGANISM: Homo sapiens

<400> SEQUENCE: 14

Thr Ser Glu Glu Thr Ile Ser Thr Val Gln Glu Lys Gln Gln Asn Ile
```

```
              1               5                  10                 15
            Ser Pro Leu Val Arg Glu Arg Gly Pro Gln Arg Val Ala Ala His Ile
                            20                 25                 30

Thr Gly Thr Arg Gly Arg Ser Asn Thr Leu Ser Ser Pro Asn Ser Lys
                            35                 40                 45

Asn Glu Lys Ala Leu Gly Arg Lys Ile Asn Ser Trp Glu Ser Ser Arg
                            50                 55                 60

Ser Gly His Ser Phe Leu Ser Asn Leu His Leu Arg Asn Gly Glu Leu
             65                 70                 75                 80

Val Ile His Glu Lys Gly Phe Tyr Tyr Ile Tyr Ser Gln Thr Tyr Phe
                            85                 90                 95

Arg Phe Gln Glu Glu Ile Lys Glu Asn Thr Lys Asn Asp Lys Gln Met
                            100                105                110

Val Gln Tyr Ile Tyr Lys Tyr Thr Ser Tyr Pro Asp Pro Ile Leu Leu
                            115                120                125

Met Lys Ser Ala Arg Asn Ser Cys Trp Ser Lys Asp Ala Glu Tyr Gly
                            130                135                140

Leu Tyr Ser Ile Tyr Gln Gly Gly Ile Phe Glu Leu Lys Glu Asn Asp
            145                150                155                160

Arg Ile Phe Val Ser Val Thr Asn Glu His Leu Ile Asp Met Asp His
                            165                170                175

Glu Ala Ser Phe Phe Gly Ala Phe Leu Val Gly
                            180                185

<210> SEQ ID NO 15
<211> LENGTH: 168
<212> TYPE: PRT
<213> ORGANISM: Homo sapiens

<400> SEQUENCE: 15

Val Arg Glu Arg Gly Pro Gln Arg Val Ala Ala His Ile Thr Gly Thr
1               5                   10                  15

Arg Gly Arg Ser Asn Thr Leu Ser Ser Pro Asn Ser Lys Asn Glu Lys
                20                  25                  30

Ala Leu Gly Arg Lys Ile Asn Ser Trp Glu Ser Ser Arg Ser Gly His
                35                  40                  45

Ser Phe Leu Ser Asn Leu His Leu Arg Asn Gly Glu Leu Val Ile His
            50                  55                  60

Glu Lys Gly Phe Tyr Tyr Ile Tyr Ser Gln Thr Tyr Phe Arg Phe Gln
65                  70                  75                  80

Glu Glu Ile Lys Glu Asn Thr Lys Asn Asp Lys Gln Met Val Gln Tyr
                85                  90                  95

Ile Tyr Lys Tyr Thr Ser Tyr Pro Asp Pro Ile Leu Leu Met Lys Ser
                100                 105                 110

Ala Arg Asn Ser Cys Trp Ser Lys Asp Ala Glu Tyr Gly Leu Tyr Ser
                115                 120                 125

Ile Tyr Gln Gly Gly Ile Phe Glu Leu Lys Glu Asn Asp Arg Ile Phe
            130                 135                 140

Val Ser Val Thr Asn Glu His Leu Ile Asp Met Asp His Glu Ala Ser
145                 150                 155                 160

Phe Phe Gly Ala Phe Leu Val Gly
                165

<210> SEQ ID NO 16
<211> LENGTH: 150
```

<212> TYPE: PRT
<213> ORGANISM: Homo sapiens

<400> SEQUENCE: 16

```
Arg Ser Asn Thr Leu Ser Ser Pro Asn Ser Lys Asn Glu Lys Ala Leu
1               5                   10                  15

Gly Arg Lys Ile Asn Ser Trp Glu Ser Ser Arg Ser Gly His Ser Phe
                20                  25                  30

Leu Ser Asn Leu His Leu Arg Asn Gly Glu Leu Val Ile His Glu Lys
            35                  40                  45

Gly Phe Tyr Tyr Ile Tyr Ser Gln Thr Tyr Phe Arg Phe Gln Glu Glu
        50                  55                  60

Ile Lys Glu Asn Thr Lys Asn Asp Lys Gln Met Val Gln Tyr Ile Tyr
65                  70                  75                  80

Lys Tyr Thr Ser Tyr Pro Asp Pro Ile Leu Leu Met Lys Ser Ala Arg
                85                  90                  95

Asn Ser Cys Trp Ser Lys Asp Ala Glu Tyr Gly Leu Tyr Ser Ile Tyr
            100                 105                 110

Gln Gly Gly Ile Phe Glu Leu Lys Glu Asn Asp Arg Ile Phe Val Ser
        115                 120                 125

Val Thr Asn Glu His Leu Ile Asp Met Asp His Glu Ala Ser Phe Phe
130                 135                 140

Gly Ala Phe Leu Val Gly
145                 150
```

<210> SEQ ID NO 17
<211> LENGTH: 281
<212> TYPE: PRT
<213> ORGANISM: Artificial Sequence
<220> FEATURE:
<223> OTHER INFORMATION: Synthetic Peptide

<400> SEQUENCE: 17

```
Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
                20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Asp Ser Tyr
        50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
```

```
                  180                 185                 190
Gln Glu Glu Ile Lys Glu Asn Thr Lys Asn Asp Lys Gln Met Val Gln
            195                 200                 205

Tyr Ile Tyr Lys Tyr Thr Ser Tyr Pro His Pro Ile Leu Leu Met Lys
            210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
            245                 250                 255

Phe Val Ser Val Thr Asn Glu His Leu Ile Asp Met Asp His Glu Ala
            260                 265                 270

Ser Phe Phe Gly Ala Phe Leu Val Gly
            275                 280

<210> SEQ ID NO 18
<211> LENGTH: 281
<212> TYPE: PRT
<213> ORGANISM: Artificial Sequence
<220> FEATURE:
<223> OTHER INFORMATION: Synthetic Peptide

<400> SEQUENCE: 18

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Asp Ser Tyr
        50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
            115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
            195                 200                 205

Tyr Ile Tyr Lys Tyr Thr Ser Tyr Pro Tyr Pro Ile Leu Leu Met Lys
            210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
            245                 250                 255

Phe Val Ser Val Thr Asn Glu His Leu Ile Asp Met Asp His Glu Ala
```

Ser Phe Phe Gly Ala Phe Leu Val Gly
            275                 280

<210> SEQ ID NO 19
<211> LENGTH: 281
<212> TYPE: PRT
<213> ORGANISM: Artificial Sequence
<220> FEATURE:
<223> OTHER INFORMATION: Synthetic Peptide

<400> SEQUENCE: 19

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met His His Glu Ala
            260                 265                 270

Ser Phe Phe Gly Ala Phe Leu Val Gly
            275                 280

<210> SEQ ID NO 20
<211> LENGTH: 281
<212> TYPE: PRT
<213> ORGANISM: Artificial Sequence
<220> FEATURE:
<223> OTHER INFORMATION: Synthetic Peptide

<400> SEQUENCE: 20

```
Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Ser Tyr
        50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Asn Ile Ser Pro
                100                 105                 110

Leu Val Arg Glu Arg Gly Pro Gln Arg Val Ala Ala His Ile Thr Gly
            115                 120                 125

Thr Arg Gly Arg Ser Asn Thr Leu Ser Ser Pro Asn Ser Lys Asn Glu
            130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
                180                 185                 190

Gln Glu Arg Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
            245                 250                 255

Phe Val Ser Val Thr Asn Glu His Leu Ile Asp Met His His Glu Ala
            260                 265                 270

Ser Phe Phe Gly Ala Phe Leu Val Gly
        275                 280

<210> SEQ ID NO 21
<211> LENGTH: 281
<212> TYPE: PRT
<213> ORGANISM: Artificial Sequence
<220> FEATURE:
<223> OTHER INFORMATION: Synthetic Peptide

<400> SEQUENCE: 21

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Ser Tyr
        50                  55                  60

Trp Asp Pro Asn Asp Glu Glu Ser Met Asn Ser Pro Cys Trp Gln Val
65                  70                  75                  80
```

```
Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Arg Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met His His Glu Ala
            260                 265                 270

Ser Phe Phe Gly Ala Phe Leu Val Gly
        275                 280

<210> SEQ ID NO 22
<211> LENGTH: 281
<212> TYPE: PRT
<213> ORGANISM: Artificial Sequence
<220> FEATURE:
<223> OTHER INFORMATION: Synthetic Peptide

<400> SEQUENCE: 22

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Pro Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160
```

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
        210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
            275                 280

<210> SEQ ID NO 23
<211> LENGTH: 281
<212> TYPE: PRT
<213> ORGANISM: Artificial Sequence
<220> FEATURE:
<223> OTHER INFORMATION: Synthetic Peptide

<400> SEQUENCE: 23

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
                20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Asp Ser Tyr
        50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Cys Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
        210                 215                 220

Ser Ala Arg Asn Ser Cys Trp Ser Lys Asp Ala Glu Tyr Gly Leu Tyr
225                 230                 235                 240

```
Ser Ile Tyr Gln Gly Gly Ile Phe Glu Leu Lys Glu Asn Asp Arg Ile
            245                 250                 255

Phe Val Ser Val Thr Asn Glu His Leu Ile Asp Met Asp His Glu Ala
            260                 265                 270

Ser Phe Phe Gly Ala Phe Leu Val Gly
            275                 280

<210> SEQ ID NO 24
<211> LENGTH: 281
<212> TYPE: PRT
<213> ORGANISM: Artificial Sequence
<220> FEATURE:
<223> OTHER INFORMATION: Synthetic Peptide

<400> SEQUENCE: 24

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
            275                 280

<210> SEQ ID NO 25
<211> LENGTH: 281
<212> TYPE: PRT
<213> ORGANISM: Artificial Sequence
<220> FEATURE:
```

<223> OTHER INFORMATION: Synthetic Peptide

<400> SEQUENCE: 25

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Gly Lys Gln Gln Asn Ile Ser Pro
            100                 105                 110

Leu Val Arg Glu Arg Gly Pro Gln Arg Val Ala Ala His Ile Cys Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 26
<211> LENGTH: 281
<212> TYPE: PRT
<213> ORGANISM: Artificial Sequence
<220> FEATURE:
<223> OTHER INFORMATION: Synthetic Peptide

<400> SEQUENCE: 26

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

```
Trp Asp Pro Asn Asp Glu Glu Ser Met Asn Ser Pro Cys Trp Gln Val
 65                  70                  75                  80

Lys Trp Gln Leu Arg Gln Leu Val Arg Lys Met Ile Leu Arg Thr Ser
             85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp Cys Glu Ala
                260                 265                 270

Ser Phe Phe Gly Ala Phe Leu Val Gly
            275                 280

<210> SEQ ID NO 27
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 27

Lys Gly Ser Gly
1

<210> SEQ ID NO 28
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 28

Arg Gly Ser Gly
1

<210> SEQ ID NO 29
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 29
```

```
Pro Gly Met Cys Gly Gly
1               5
```

<210> SEQ ID NO 30
<211> LENGTH: 203
<212> TYPE: PRT
<213> ORGANISM: Artificial Sequence
<220> FEATURE:
<223> OTHER INFORMATION: Synthetic Peptide

<400> SEQUENCE: 30

```
Gly Arg Met Lys Gln Ile Glu Asp Lys Ile Glu Ile Leu Ser Lys
1               5                   10                  15

Ile Tyr His Val Glu Asn Glu Ile Ala Arg Ile Lys Glu Leu Ile Gly
                20                  25                  30

Glu Asp Gly Val Arg Glu Arg Gly Pro Gln Arg Val Ala Ala His Ile
            35                  40                  45

Thr Gly Thr Arg Gly Arg Ser Asn Thr Leu Ser Ser Pro Asn Ser Lys
    50                  55                  60

Asn Glu Lys Ala Leu Gly Arg Lys Ile Asn Ser Trp Glu Ser Ser Arg
65                  70                  75                  80

Ser Gly His Ser Phe Leu Ser Asn Leu His Leu Arg Asn Gly Glu Leu
                85                  90                  95

Val Ile His Glu Lys Gly Phe Tyr Tyr Ile Tyr Ser Gln Thr Tyr Phe
            100                 105                 110

Arg Phe Gln Glu Glu Ile Lys Glu Asn Thr Lys Asn Asp Lys Gln Met
        115                 120                 125

Val Gln Tyr Ile Tyr Lys Tyr Thr Ser Tyr Pro Asp Pro Ile Leu Leu
    130                 135                 140

Met Lys Ser Ala Arg Asn Ser Cys Trp Ser Lys Asp Ala Glu Tyr Gly
145                 150                 155                 160

Leu Tyr Ser Ile Tyr Gln Gly Gly Ile Phe Glu Leu Lys Glu Asn Asp
                165                 170                 175

Arg Ile Phe Val Ser Val Thr Asn Glu His Leu Ile Asp Met Asp His
            180                 185                 190

Glu Ala Ser Phe Phe Gly Ala Phe Leu Val Gly
        195                 200
```

<210> SEQ ID NO 31
<211> LENGTH: 204
<212> TYPE: PRT
<213> ORGANISM: Artificial Sequence
<220> FEATURE:
<223> OTHER INFORMATION: Synthetic Peptide

<400> SEQUENCE: 31

```
Met Gly Arg Met Lys Gln Ile Glu Asp Lys Ile Glu Ile Leu Ser
1               5                   10                  15

Lys Ile Tyr His Val Glu Asn Glu Ile Ala Arg Ile Lys Glu Leu Ile
                20                  25                  30

Gly Glu Asp Gly Val Arg Glu Arg Gly Pro Gln Arg Val Ala Ala His
            35                  40                  45

Ile Thr Gly Thr Arg Gly Arg Ser Asn Thr Leu Ser Ser Pro Asn Ser
    50                  55                  60

Lys Asn Glu Lys Ala Leu Gly Arg Lys Ile Asn Ser Trp Glu Ser Ser
65                  70                  75                  80

Arg Ser Gly His Ser Phe Leu Ser Asn Leu His Leu Arg Asn Gly Glu
                85                  90                  95
```

```
Leu Val Ile His Glu Lys Gly Phe Tyr Tyr Ile Tyr Ser Gln Thr Tyr
            100                 105                 110

Phe Arg Phe Gln Glu Glu Ile Lys Glu Asn Thr Lys Asn Asp Lys Gln
        115                 120                 125

Met Val Gln Tyr Ile Tyr Lys Tyr Thr Ser Tyr Pro Asp Pro Ile Leu
    130                 135                 140

Leu Met Lys Ser Ala Arg Asn Ser Cys Trp Ser Lys Asp Ala Glu Tyr
145                 150                 155                 160

Gly Leu Tyr Ser Ile Tyr Gln Gly Gly Ile Phe Glu Leu Lys Glu Asn
                165                 170                 175

Asp Arg Ile Phe Val Ser Val Thr Asn Glu His Leu Ile Asp Met Asp
            180                 185                 190

His Glu Ala Ser Phe Phe Gly Ala Phe Leu Val Gly
            195                 200
```

<210> SEQ ID NO 32
<211> LENGTH: 216
<212> TYPE: PRT
<213> ORGANISM: Artificial Sequence
<220> FEATURE:
<223> OTHER INFORMATION: Synthetic Peptide

<400> SEQUENCE: 32

```
Met Gly His His His His His His Pro Gly Met Cys Gly Gly
1               5                   10                  15

Lys Gln Ile Glu Asp Lys Ile Glu Ile Leu Ser Lys Ile Tyr His
            20                  25                  30

Ile Glu Asn Glu Ile Ala Arg Ile Lys Lys Leu Ile Gly Glu Asp Gly
        35                  40                  45

Val Arg Glu Arg Gly Pro Gln Arg Val Ala Ala His Ile Thr Gly Thr
    50                  55                  60

Arg Gly Arg Ser Asn Thr Leu Ser Ser Pro Asn Ser Lys Asn Glu Lys
65                  70                  75                  80

Ala Leu Gly Arg Lys Ile Asn Ser Trp Glu Ser Ser Arg Ser Gly His
                85                  90                  95

Ser Phe Leu Ser Asn Leu His Leu Arg Asn Gly Glu Leu Val Ile His
            100                 105                 110

Glu Lys Gly Phe Tyr Tyr Ile Tyr Ser Gln Thr Tyr Phe Arg Phe Gln
        115                 120                 125

Glu Glu Ile Lys Glu Asn Thr Lys Asn Asp Lys Gln Met Val Gln Tyr
    130                 135                 140

Ile Tyr Lys Tyr Thr Ser Tyr Pro Asp Pro Ile Leu Leu Met Lys Ser
145                 150                 155                 160

Ala Arg Asn Ser Cys Trp Ser Lys Asp Ala Glu Tyr Gly Leu Tyr Ser
                165                 170                 175

Ile Tyr Gln Gly Gly Ile Phe Glu Leu Lys Glu Asn Asp Arg Ile Phe
            180                 185                 190

Val Ser Val Thr Asn Glu His Leu Ile Asp Met Asp His Glu Ala Ser
        195                 200                 205

Phe Phe Gly Ala Phe Leu Val Gly
    210                 215
```

<210> SEQ ID NO 33
<211> LENGTH: 663
<212> TYPE: DNA
<213> ORGANISM: Artificial Sequence
<220> FEATURE:
<223> OTHER INFORMATION: Nucleotide sequence encoding a fusion
    polypeptide

<400> SEQUENCE: 33

| | | |
|---|---|---|
| catatgggcc atcatcacca ccatcatcat cacccaggca tgtgcggcgg caaacagatc | 60 |
| gaagataaga ttgaagaaat tctgtccaag atttaccaca tcgagaatga aatcgcacgt | 120 |
| atcaaaaagc tgatcggtga ggacggtgtc cgcgagcgtg gtccgcagcg tgttgcggcg | 180 |
| catatcacgg gtactcgtgg tcgcagcaac accctgagca gcccgaatag caaaaatgaa | 240 |
| aaggctctgg tcgtaagat taactcctgg gagagcagcc gctccggtca cagcttcctg | 300 |
| agcaatctgc acttgcgtaa cggtgagctg gttattcacg agaaaggctt ctattacatt | 360 |
| tacagccaaa cctattttcg ttttcaagag gaaatcaaag agaataccaa aaacgataag | 420 |
| caaatggttc agtacatcta caagtacacc tcgtatccgg acccgatcct gttgatgaaa | 480 |
| agcgcgcgta atagctgttg gtctaaagat gcagagtatg gtctgtatag catttaccag | 540 |
| ggtggcattt tcgagctgaa agaaaacgac cgcatctttg tctctgtgac gaacgaacac | 600 |
| ctgattgaca tggatcacga agcgagcttc tttggcgcct tcctggtggg ttaataagag | 660 |
| ctc | 663 |

<210> SEQ ID NO 34
<211> LENGTH: 627
<212> TYPE: DNA
<213> ORGANISM: Artificial Sequence
<220> FEATURE:
<223> OTHER INFORMATION: Nucleotide sequence encoding a fusion
    polypeptide

<400> SEQUENCE: 34

| | | |
|---|---|---|
| catatgggga ggatgaagca aatagaggat aagatcgagg agatcctctc gaagatatac | 60 |
| cacgtcgaga acgagatagc ccgtatcaaa gagcttattg gggaagatgg agtcagggag | 120 |
| aggggtcccc agagagtggc agcacacatt accggtacaa gaggccgtag taatacccte | 180 |
| agtagcccta atagtaaaaa cgagaaagcc ctcggacgca agattaactc gtgggaatct | 240 |
| tctcgctccg ggcactcttt tctttcgaac ttgcatctga gaaatgggga gctggtgatt | 300 |
| cacgagaagg gattctacta catctattcc cagacgtact tccggttcca ggaggagata | 360 |
| aaagagaaca cgaagaacga caagcagatg gtccagtaca tctacaagta cacgtcttac | 420 |
| ccggacccta tcctcttaat gaagtcggcg cgtagctcct gttggtctaa agacgcagag | 480 |
| tatggattgt acagtattta ccagggaggg atattcgagc tgaaggaaaa cgatcggatc | 540 |
| ttcggatcgg ttaccgatga gcacctgata gacatggatc atgaggctag cttctttgga | 600 |
| gcattttttgg tgggataata agagctc | 627 |

<210> SEQ ID NO 35
<211> LENGTH: 663
<212> TYPE: DNA
<213> ORGANISM: Artificial Sequence
<220> FEATURE:
<223> OTHER INFORMATION: Nucleotide sequence encoding a fusion
    polypeptide

<400> SEQUENCE: 35

| | | |
|---|---|---|
| catatgggcc atcatcacca ccatcatcat cacccaggca tgtgcggcgg caaacagatc | 60 |
| gaagataaga ttgaagaaat tctgtccaag atttaccaca tcgagaatga aatcgcacgt | 120 |
| atcaaaaagc tgatcggtga ggacggtgtc cgcgagcgtg gtccgcagcg tgttgcggcg | 180 |

```
catatcacgg gtactcgtgg tcgcagcaac accctgagca gcccgaatag caaaaatgaa    240
aaggctctgg gtcgtaagat taactcctgg gagagcagcc gctccggtca cagcttcctg    300
agcaatctgc acttgcgtaa cggtgagctg gttattcacg agaaaggctt ctattacatt    360
tacagccaaa cctatttttcg ttttcaagag gaaatcaaag agaataccaa aaacgataag    420
caaatggttc agtacatcta caagtacacc tcgtatccgg acccgatcct gttgatgaaa    480
agcgcgcgta atagctgttg gtctaaagat gcagagtatg gtctgtatag catttaccag    540
ggtggcattt tcgagctgaa agaaaacgac cgcatctttg tctctgtgac gaacgaacac    600
ctgattgaca tggatcacga agcgagcttc tttggcgcct tcctggtggg ttaataagag    660
ctc                                                                 663
```

<210> SEQ ID NO 36
<211> LENGTH: 663
<212> TYPE: DNA
<213> ORGANISM: Artificial Sequence
<220> FEATURE:
<223> OTHER INFORMATION: Nucleotide sequence encoding a fusion polypeptide

<400> SEQUENCE: 36

```
catatgggcc atcatcacca ccatcatcat cacccaggca tgtgcggcgg caaacagatc     60
gaagataaga ttgaagaaat tctgtccaag atttaccacg tggagaatga atcgcacgt    120 atcaaagaac tgatcggtga ggacggtgtc cgcgagcgtg gtccgcagcg tgttgcggcg    180
catatcacgg gtactcgtgg tcgcagcaac accctgagca gcccgaatag caaaaatgaa    240
aaggctctgg gtcgtaagat taactcctgg gagagcagcc gctccggtca cagcttcctg    300
agcaatctgc acttgcgtaa cggtgagctg gttattcacg agaaaggctt ctattacatt    360
tacagccaaa cctatttttcg ttttcaagag gaaatcaaag agaataccaa aaacgataag    420
caaatggttc agtacatcta caagtacacc tcgtatccgg acccgatcct gttgatgaaa    480
agcgcgcgta atagctgttg gtctaaagat gcagagtatg gtctgtatag catttaccag    540
ggtggcattt tcgagctgaa agaaaacgac cgcatctttg tctctgtgac gaacgaacac    600
ctgattgaca tggatcacga agcgagcttc tttggcgcct tcctggtggg ttaataagag    660
ctc                                                                 663
```

<210> SEQ ID NO 37
<211> LENGTH: 663
<212> TYPE: DNA
<213> ORGANISM: Artificial Sequence
<220> FEATURE:
<223> OTHER INFORMATION: Nucleotide sequence encoding a fusion polypeptide

<400> SEQUENCE: 37

```
catatgggcc atcatcacca ccatcatcat cacccaggca tgtgcggcgg caaacagatc     60
gaagataaga ttgaagaaat tctgtccaag atttaccacg tggagaatga atcgcacgt    120 atcaaaaagc tgatcggtga ggacggtgtc cgcgagcgtg gtccgcagcg tgttgcggcg    180
catatcacgg gtactcgtgg tcgcagcaac accctgagca gcccgaatag caaaaatgaa    240
aaggctctgg gtcgtaagat taactcctgg gagagcagcc gctccggtca cagcttcctg    300
agcaatctgc acttgcgtaa cggtgagctg gttattcacg agaaaggctt ctattacatt    360
tacagccaaa cctatttttcg ttttcaagag gaaatcaaag agaataccaa aaacgataag    420
```

```
caaatggttc agtacatcta caagtacacc tcgtatccgg acccgatcct gttgatgaaa    480
agcgcgcgta atagctgttg gtctaaagat gcagagtatg gtctgtatag catttaccag    540
ggtggcattt tcgagctgaa agaaaacgac cgcatctttg tctctgtgac gaacgaacac    600
ctgattgaca tggatcacga agcgagcttc tttggcgcct tcctggtggg ttaataagag    660
ctc                                                                  663
```

<210> SEQ ID NO 38
<211> LENGTH: 663
<212> TYPE: DNA
<213> ORGANISM: Artificial Sequence
<220> FEATURE:
<223> OTHER INFORMATION: Nucleotide sequence encoding a fusion
      polypeptide

<400> SEQUENCE: 38

```
catatgggcc atcatcacca ccatcatcat cacccaggca tgtgcggcgg caaacagatc     60
gaagataaga ttgaagaaat tctgtccaag atttaccaca tcgagaatga aatcgcacgt    120
atcaaagaac tgatcggtga ggacggtgtc cgcgagcgtg gtccgcagcg tgttgcggcg    180
catatcacgg gtactcgtgg tcgcagcaac accctgagca gcccgaatag caaaaatgaa    240
aaggctctgg gtcgtaagat taactcctgg gagagcagcc gctccggtca cagcttcctg    300
agcaatctgc acttgcgtaa cggtgagctg gttattcacg agaaaggctt ctattacatt    360
tacagccaaa cctattttcg ttttcaagag gaaatcaaag agaataccaa aaacgataag    420
caaatggttc agtacatcta caagtacacc tcgtatccgg acccgatcct gttgatgaaa    480
agcgcgcgta atagctgttg gtctaaagat gcagagtatg gtctgtatag catttaccag    540
ggtggcattt tcgagctgaa agaaaacgac cgcatctttg tctctgtgac gaacgaacac    600
ctgattgaca tggatcacga agcgagcttc tttggcgcct tcctggtggg ttaataagag    660
ctc                                                                  663
```

<210> SEQ ID NO 39
<211> LENGTH: 663
<212> TYPE: DNA
<213> ORGANISM: Artificial Sequence
<220> FEATURE:
<223> OTHER INFORMATION: Nucleotide sequence encoding a fusion
      polypeptide

<400> SEQUENCE: 39

```
catatgggcc atcatcacca ccatcatcat cacccaggca tgtgcggcgg caaacagatc     60
gaagataaga ttgaagaaat tctgtccaag atttaccaca tcgagaatga aatcgcacgt    120
atcaaacaac tgatcggtga ggacggtgtc cgcgagcgtg gtccgcagcg tgttgcggcg    180
catatcacgg gtactcgtgg tcgcagcaac accctgagca gcccgaatag caaaaatgaa    240
aaggctctgg gtcgtaagat taactcctgg gagagcagcc gctccggtca cagcttcctg    300
agcaatctgc acttgcgtaa cggtgagctg gttattcacg agaaaggctt ctattacatt    360
tacagccaaa cctattttcg ttttcaagag gaaatcaaag agaataccaa aaacgataag    420
caaatggttc agtacatcta caagtacacc tcgtatccgg acccgatcct gttgatgaaa    480
agcgcgcgta atagctgttg gtctaaagat gcagagtatg gtctgtatag catttaccag    540
ggtggcattt tcgagctgaa agaaaacgac cgcatctttg tctctgtgac gaacgaacac    600
ctgattgaca tggatcacga agcgagcttc tttggcgcct tcctggtggg ttaataagag    660
ctc                                                                  663
```

<210> SEQ ID NO 40
<211> LENGTH: 663
<212> TYPE: DNA
<213> ORGANISM: Artificial Sequence
<220> FEATURE:
<223> OTHER INFORMATION: Nucleotide sequence encoding a fusion
      polypeptide

<400> SEQUENCE: 40

```
catatgggcc atcatcacca ccatcatcat cacccaggca tgtgcggcgg caaacagatc    60
gaagataaga ttgaagaaat tctgtccaag atttaccacg tggagaatga aatcgcacgt   120
atcaaacaac tgatcggtga ggacggtgtc cgcgagcgtg gtccgcagcg tgttgcggcg   180
catatcacgg gtactcgtgg tcgcagcaac accctgagca gcccgaatag caaaaatgaa   240
aaggctctgg gtcgtaagat taactcctgg gagagcagcc gctccggtca cagcttcctg   300
agcaatctgc acttgcgtaa cggtgagctg gttattcacg agaaaggctt ctattacatt   360
tacagccaaa cctattttcg ttttcaagag gaaatcaaag agaataccaa aaacgataag   420
caaatggttc agtacatcta caagtacacc tcgtatccgg acccgatcct gttgatgaaa   480
agcgcgcgta atagctgttg gtctaaagat gcagagtatg gtctgtatag catttaccag   540
ggtggcattt tcgagctgaa agaaaacgac cgcatctttg tctctgtgac gaacgaacac   600
ctgattgaca tggatcacga agcgagcttc tttggcgcct cctggtggg ttaataagag    660
ctc                                                                663
```

<210> SEQ ID NO 41
<211> LENGTH: 25
<212> TYPE: DNA
<213> ORGANISM: Artificial Sequence
<220> FEATURE:
<223> OTHER INFORMATION: Synthetic primer

<400> SEQUENCE: 41

```
gggaagaaga ttctcctgag atgtg                                         25
```

<210> SEQ ID NO 42
<211> LENGTH: 23
<212> TYPE: DNA
<213> ORGANISM: Artificial Sequence
<220> FEATURE:
<223> OTHER INFORMATION: thetic primer

<400> SEQUENCE: 42

```
acattgtcct cagccccagg tcg                                           23
```

<210> SEQ ID NO 43
<211> LENGTH: 19
<212> TYPE: DNA
<213> ORGANISM: Artificial Sequence
<220> FEATURE:
<223> OTHER INFORMATION: Synthetic primer

<400> SEQUENCE: 43

```
aagacccttg tgctcgttg                                                19
```

<210> SEQ ID NO 44
<211> LENGTH: 20
<212> TYPE: DNA
<213> ORGANISM: Artificial Sequence
<220> FEATURE:
<223> OTHER INFORMATION: Synthetic primer

```
<400> SEQUENCE: 44
aggtggacac aatccctctg                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic primer

<400> SEQUENCE: 45
ccagagccat tgtcacacac                                              20

<210> SEQ ID NO 46
<211> LENGTH: 18
<212> TYPE: DNA
<213> ORGANISM: Artificial Sequence
<220> FEATURE:
<223> OTHER INFORMATION: Synthetic primer

<400> SEQUENCE: 46
cagccaagca ctgtcagg                                                18

<210> SEQ ID NO 47
<211> LENGTH: 18
<212> TYPE: DNA
<213> ORGANISM: Artificial Sequence
<220> FEATURE:
<223> OTHER INFORMATION: Synthetic primer

<400> SEQUENCE: 47
cttccagccg aggtcctt                                                18

<210> SEQ ID NO 48
<211> LENGTH: 20
<212> TYPE: DNA
<213> ORGANISM: Artificial Sequence
<220> FEATURE:
<223> OTHER INFORMATION: Synthetic primer

<400> SEQUENCE: 48
ccctggacac caactattgc                                              20

<210> SEQ ID NO 49
<211> LENGTH: 20
<212> TYPE: DNA
<213> ORGANISM: Artificial Sequence
<220> FEATURE:
<223> OTHER INFORMATION: Synthetic primer

<400> SEQUENCE: 49
agcaggtcct tggaaacctt                                              20

<210> SEQ ID NO 50
<211> LENGTH: 20
<212> TYPE: DNA
<213> ORGANISM: Artificial Sequence
<220> FEATURE:
<223> OTHER INFORMATION: Synthetic primer

<400> SEQUENCE: 50
gaaaaggagt tggacttggc                                              20

<210> SEQ ID NO 51
```

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 51
aaatggaacc tggcgaaagc                                              20

<210> SEQ ID NO 52
<211> LENGTH: 20
<212> TYPE: DNA
<213> ORGANISM: Artificial Sequence
<220> FEATURE:
<223> OTHER INFORMATION: Synthetic primer

<400> SEQUENCE: 52
gatgagcccc tcaggcattt                                              20

<210> SEQ ID NO 53
<211> LENGTH: 20
<212> TYPE: DNA
<213> ORGANISM: Artificial Sequence
<220> FEATURE:
<223> OTHER INFORMATION: Synthetic primer

<400> SEQUENCE: 53
gtcttgggag ccagggtgac                                              20

<210> SEQ ID NO 54
<211> LENGTH: 21
<212> TYPE: DNA
<213> ORGANISM: Artificial Sequence
<220> FEATURE:
<223> OTHER INFORMATION: Synthetic primer

<400> SEQUENCE: 54
tgaaaagtgc aaatggcaag c                                            21

<210> SEQ ID NO 55
<211> LENGTH: 20
<212> TYPE: DNA
<213> ORGANISM: Artificial Sequence
<220> FEATURE:
<223> OTHER INFORMATION: Synthetic primer

<400> SEQUENCE: 55
ctaccacatc caaggaagca                                              20

<210> SEQ ID NO 56
<211> LENGTH: 21
<212> TYPE: DNA
<213> ORGANISM: Artificial Sequence
<220> FEATURE:
<223> OTHER INFORMATION: Synthetic primer

<400> SEQUENCE: 56
tttttcgtca ctacctcccc g                                            21
```

TRAIL COMPOSITIONS WITH REDUCED IMMUNOGENICITY

CROSS REFERENCE TO RELATED APPLICATIONS

This application claims benefit of and priority to U.S. Provisional Application No. 63/035,472 filed Jun. 5, 2020, which is specifically incorporated by reference herein in its entirety.

STATEMENT REGARDING FEDERALLY SPONSORED RESEARCH

This invention was made with Government support under Grant No. 4U44AA026111-03 awarded by the National Institutes of Health. The Government has certain rights in the invention.

REFERENCE TO SEQUENCE LISTING

The Sequence Listing submitted Apr. 5, 2021 as a text file named "THER_116_US_ST25.txt," created on Apr. 1, 2021, and having a size of 60,786 bytes is hereby incorporated by reference pursuant to 37 C.F.R. § 1.52(e)(5).

FIELD OF THE INVENTION

The invention is generally directed to fusion polypeptides containing Tumor necrosis factor-Related Apoptosis-Inducing Ligand (TRAIL) containing a modified isoleucine zipper (miLZ) domain.

BACKGROUND OF THE INVENTION

Tumor necrosis factor-related apoptosis-inducing ligand (TRAIL) is a type II transmembrane protein in the TNF-α superfamily with sequence homology with TNF and FasL. TRAIL can be proteolytically cleaved from the cell surface and released in soluble form. Soluble TRAIL is intrinsically a homotrimer and subsequently trimerizes TRAIL-receptors after binding. Five TRAIL receptors have been identified in humans, but only TRAIL-R1/DR4 and TRAIL-R2/DR5 receptors initiate apoptosis similar to Fas/FasL and TNF-R/TNF signaling pathways. TRAIL receptor binding stimulates formation of death-inducing signaling complex (DISC) with the recruited adaptor protein, Fas-associated protein with death domain (FADD). FADD recruits procaspases 8 and 10, and DISC allows auto-activation of these caspases. Downstream of this signaling is the proteolytic cleavage and activation of caspases 3/6/7, resulting in apoptosis. Another pathway of apoptosis is the induction of mitochondrial dysfunction and membrane permeabilization causing release of cytochrome c that activates caspase 9 and finally cleavage of caspase 3/7, resulting in apoptosis. TRAIL can also bind to its decoy receptors, TRAIL-R3/DcR1 and TRAIL-R4/DcR2, but these receptors lack a functional death domain and are unable to induce apoptosis.

A major difference between TRAIL and other members of the TNF superfamily, such as TNF and CD95L, is TRAIL's failure to induce cell death of normal tissues. A variety of medical or pharmaceutical applications have been attempted using TNF and CD95L to induce cell death. Since TNF and CD95L proteins induce death of normal cells as well as cancer cells and over-activated immune cells, they have limited applicability. In contrast, TRAIL induces apoptosis in a wide range of cancer cells and over-activated immune cells with little effect on normal cells. This is due to the differential expression of TRAIL receptors between cell types.

Five TRAIL receptors have been identified. Among them, DR4 (TRAIL-R1) and DR5 (TRAIL-R2) are representative cell death-related receptors. When TRAIL binds to DR4 or DR5, an intracellular death domain of the receptor is activated and thereby transduces apoptotic signals via various signal transduction pathways, leading to apoptotic cell death. TRAIL can also bind to DcR1, DcR2 and osteoprotegerin (OPG), which do not induce apoptosis. No marked difference has been seen in the expression levels of the cell death-inducing receptors DR4 and DR5 between normal and tumor cells. In contrast, the three other receptors not inducing apoptosis are expressed at high levels in normal cells, but are either expressed at low levels or are not expressed at all in tumor cells. Thus, in normal cells, TRAIL binds mostly to DcR1, DcR2 and OPG, which do not contain a death domain, and thereby do not induce cell death. In contrast, in cancer cells and over-activated immune cells, apoptosis is induced by the binding of TRAIL to DR4 and DR5, which contain death domains. Such selective apoptosis induction of TRAIL is a particularly attractive feature in medical or pharmaceutical applications.

TRAIL-mediated apoptosis has been observed in various types of cancer cells, including colon carcinoma, glioma, lung carcinoma, prostate carcinoma, brain tumors and multiple myeloma cells. TRAIL has been proven to have very high anticancer activity in animals. Good anticancer efficacy of TRAIL has been obtained through the use of TRAIL alone, as well as in combination with other anticancer agents, such as paclitaxel and doxorubicin, and radiotherapy. In addition to cancer, TRAIL has been used to treat arthritis, an autoimmune disease, relieving and treating arthropathy by inducing the death of overactivated immune cells. In addition to protein therapy, gene therapy has been attempted through the delivery of the TRAIL gene. TRAIL may also be useful in the treatment of T cell-mediated autoimmune disorders such as lupus, rheumatoid arthritis and type I diabetes.

However, native TRAIL has some problems as a therapeutic. The major problem is the low trimer formation ratio of native TRAIL. TRAIL monomers do not bind to the TRAIL receptors, and thus do not induce apoptosis. In this regard, many studies have been performed with the goal of improving the trimeric structure and trimer formation ratio of TRAIL. Zinc ions play a critical role in trimerization of native TRAIL. Mutants of TRAIL have been developed based on computer analysis results. For the formation of TRAIL trimers, the most useful method appears to be the introduction of an amino acid sequence favoring trimeric folding. Such sequences include a leucine zipper (LZ) motif and an isoleucine zipper (iLZ) motif. Henning Walczak reported the anticancer efficacy of a trimeric TRAIL derivative in which a leucine zipper motif is added to the N terminus of native TRAIL (Walczak et al., *Nature Medicine*, 5:157-163 (1999)). Kim reported a TRAIL derivative containing a isoleucine zipper motif and having good apoptotic activity (Kim et al., *BBRC*, 321:930-935 (2004)).

TRAIL has different half-lives in different species. For example, TRAIL has been reported to have a half-life of several minutes in rodents and about 30 minutes in apes (Xiang, et al., *Drug Metabolism and Disposition*, 32:1230-1238 (2004)). Most TRAIL is rapidly excreted via the kidneys. This short half-life is considered a drawback to the pharmaceutical usefulness of TRAIL, resulting in a need for TRAIL or derivatives thereof having an extended half-life.

Other problems to be solved include the low solubility and solution stability of TRAIL. Recombinant TRAIL has an extremely short half-life, is unstable and aggregates at high concentrations. As a result, unmodified TRAIL has limited use for in vivo drug development.

Another problem in the clinical applications of TRAIL involves cytotoxicity in normal cells of some tissues. Most normal cells are resistant to cytotoxicity, resulting from the expression of the various TRAIL receptors, but some hepatocytes and keratinocytes are sensitive to TRAIL-mediated cytotoxicity (Yagita et al., *Cancer Sci.*, 95:777-783 (2004); Jo et al., *Nature Medicine*, 6:564-567 (2000); Zheng et al., *J. Clin. Invest.*, 113:58-64 (2004)).

There remains a need for biologically active, highly pure TRAIL compositions and TRAIL conjugates that retain biological activity of native TRAIL, have a prolonged serum half-life, increased solubility, and which are not cytotoxic to healthy cells and non-immunogenic in the host.

Therefore, it is the object of the present invention to provide non-immunogenic TRAIL compositions and TRAIL conjugates with prolonged serum half-life, high solubility, high bioactivity, and low toxicity to healthy cells.

It is another object of the present invention to provide methods of making the non-immunogenic TRAIL compositions and TRAIL conjugates.

It is yet another object of the present invention to provide methods of using the non-immunogenic TRAIL compositions and TRAIL conjugates.

SUMMARY OF THE INVENTION

Fusion polypeptides with a modified multimerization domain and a TRAIL domain have high expression, solubility, and stability. The fusion polypeptides typically have low immunogenicity in a host when compared to that of other TRAIL polypeptides in the art with unmodified multimerization domain. Conjugates of the fusion polypeptides, polynucleotides encoding the fusion polypeptides, and compositions thereof, have been developed. Typically, the fusion polypeptides are recombinant fusion polypeptides containing a first sequence containing a modified isoleucine zipper (miLZ) domain and a second sequence. The first sequence may include any one of SEQ ID NO:4-8. The second sequence is typically a TRAIL domain and may include any one of SEQ ID NOs: 9-26. The first sequence may be joined to the second sequence via a linker, such as an amino acid linker. The fusion polypeptide may include an expression sequence preceding the first sequence. An exemplary fusion polypeptide has an amino acid sequence as shown in SEQ ID NO:30.

The modified isoleucine zipper (miLZ) domains of the fusion polypeptides have modifications of the isoleucine residue at position 17 and the lysine residue at position 26 of the isoleucine zipper (iLZ) known in the art (iLZ containing a sequence as shown in SEQ ID NO:1 and miLZ containing a sequence as shown in SEQ ID NO:4-8). These modifications of the iLZ do not affect the multimerization of the fusion polypeptide, so they can be used to produce a TRAIL trimer that is stable, soluble, has an increased half-life in vivo, and reduced immunogenicity. This is contrary to the art showing that the isoleucine residues at this position (Ile at position 20 of SEQ ID NO:2 (corresponding to position 17 in SEQ ID NO:1) was needed and conferred stable trimer formation to TRAIL (Harbury et al, *Nature*, 371:80-83 (1994); Rozanov et al., *Mol Cancer Ther*, 8:1515-1525 (2009), disclosing SEQ ID NO:3).

The fusion polypeptides in the multimeric form, such as in a trimeric form, typically are highly soluble, having a solubility in physiological buffer and pH and room temperature at between about 0.2 mg/ml and 100 mg/ml. The fusion polypeptides in the multimeric form, such as in a trimeric form, have half maximal inhibitory concentration (IC50) in vitro significantly lower than that for a fusion polypeptide containing an unmodified iLZ domain. The IC50 for a fusion polypeptide may be between about 2 and about 10 fold or more lower when compared to that for a fusion polypeptide containing an unmodified iLZ domain. The fusion polypeptide typically has a half-life in vivo greater than 1 hour, such as between about 1 hour and about 24 hours, between about 1 and about 12 hours, or between about 1 and about 6 hours.

Fusion polypeptides stably conjugated to a half-life extending molecule, such as to a polyethylene glycol (PEG) or a derivative thereof, have been developed. Typically, the PEG or the derivative thereof has a molecular weight between about 5 000 Da and about 100 000 Da. The conjugates generally are highly soluble, having a solubility of up to about 30 mg/ml, such as about 25 mg/ml, in presence of a physiological concentration of salts. The conjugates are typically highly stable and do not have substantially reduced solubility and activity with repeat freeze-thaw cycles. The conjugates typically have a long in vivo half-life, such as a half-life in vivo between about 20 hours and about 50 hours in non-human primates. The IC50 for the conjugate may be between about 2 and about 10 fold or more lower when compared to than that for a conjugate containing an unmodified iLZ domain. The conjugate typically has a substantially lower immunogenicity in a mammalian host when compared to that of a conjugate containing an unmodified iLZ domain.

Polynucleotides that encode the recombinant fusion polypeptide have also been developed. The polynucleotides may be in an expression vector. The expression vector typically includes a promoter operably linked to the polynucleotide. The promoter can be any promoter including a constitutively active, inducible, conditional, or tissue specific promoter. The polynucleotide can be used for expression in yeast (such as *Pichia pastoris*) or *E. coli* expression systems.

Pharmaceutical compositions contain an effective amount of the fusion polypeptides, polynucleotides, or the conjugate. These are typically formulated for administration by injection.

Methods of making the fusion polypeptides have been developed. Such methods include transfecting an expression host such as *E. coli* cells with an expression vector containing a polynucleotide encoding the fusion polypeptide and an inducible promoter. The transfected *E. coli* cells are used to inoculate a media. The media typically includes zinc ions, such as in a form of zinc chloride.

Methods of treating proliferative, autoimmune, or fibrotic diseases in a subject in need thereof require administering the fusion polypeptides, the conjugates, the polynucleotides, or the pharmaceutical compositions to the subject. The fusion polypeptides, the conjugates, the polynucleotides, or the pharmaceutical compositions are particularly effective at inducing cancer associated fibroblast apoptosis.

BRIEF DESCRIPTION OF THE DRAWINGS

FIG. 1A is a diagram of prior art (Chae, et al., *Molecular cancer therapeutics* 9(6):1719-29 (2010)) histidine tag-containing iLZ-TRAIL (His-iLZ-TRAIL) sequence with a recombinant human TRAIL (amino acids 114-281) preceded by an isoleucine zipper with low expression sequence and immunogenic epitopes, and preceded by a histidine (His) tag; FIG. 1B shows miLZ-TRAIL—a recombinant human TRAIL (amino acids 114-281) preceded by an isoleucine zipper with an improved expression sequence, deimmunized epitopes and without a histidine (His) tag (FIG. 1B); and FIG. 1C shows the sequence in FIG. 1B PEGylated with a 5 kDa PEG at the N-terminus.

FIG. 6 is a table showing the output of in silico immunogenicity analysis of the various miLZ domains using the ProPred based algorithm. The software interrogates a broad range of human MHC-II alleles for the ability to bind potential T-cell epitopes (linear nonapeptides) presented in the protein sequence. Each amino acid in the potential T-cell epitope is assigned an immunogenicity score. The score is proportional to the likelihood of the peptide to bind to a certain MHC-II allele and trigger a T-cell immune response.

DETAILED DESCRIPTION OF THE INVENTION

I. Definitions

Figure 1A:
FIGS. 1A-1C are diagrams showing sequences for the known fusion polypeptides and the modified fusion polypeptides.

As used herein, the term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, the term "variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (0.4); threonine (−0.7); serine (−0.8); tryptophan (−0.9); tyrosine (−1.3); proline (1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, and antigens. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity. The following hydrophilicity values have been assigned to amino acid residues: arginine (+3.0); lysine (+3.0); aspartate (+3.0±1); glutamate (+3.0±1); serine (+0.3); asparagine (+0.2); glutamnine (+0.2); glycine (0); proline (−0.5±1); threonine (−0.4); alanine (−0.5); histidine (−0.5); cysteine (1.0); methionine (−1.3); valine (−1.5); leucine (−1.8); isoleucine (−1.8); tyrosine (2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. In particular, embodiments of the polypeptides can include variants having about 50%, 60%, 70%, 80%, 90%, and 95% sequence identity to the polypeptide of interest.

As used herein, the term "identity," as known in the art, is a relationship between two or more polypeptide sequences, as determined by comparing the sequences. In the art, "identity" also means the degree of sequence relatedness between polypeptide as determined by the match between strings of such sequences. "Identity" can also mean the degree of sequence relatedness of a polypeptide compared to the full-length of a reference polypeptide. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Various programs and alignment algorithms are described in: Smith & Waterman, *Adv Appl Math* 2, 482 (1981); Needleman & Wunsch, *J Mol Biol* 48, 443 (1970); Pearson & Lipman, *Proc Natl Acad Sci USA* 85, 2444 (1988); Higgins & Sharp, *Gene* 73, 237-244 (1988); Higgins & Sharp, *CABIOS* 5, 151-153 (1989); Corpet et al, *Nuc Acids Res* 16, 10881-10890 (1988); Huang et al, *Computer App Biosci* 8, 155-165 (1992); and Pearson et al, *Meth Mol Bio* 24, 307-331 (1994). In addition, Altschul et al, *J Mol Biol* 215, 403-410 (1990), presents a detailed consideration of sequence alignment methods and homology calculations.

The NCBI Basic Local Alignment Search Tool (BLAST) (Altschul et al, (1990) supra) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site. BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Preferred methods to determine identity are designed to give the largest match between the sequences tested. Methods to determine identity and similarity are codified in publicly available computer programs. The percent identity between two sequences can be determined using analysis software (i.e., Sequence Analysis Software Package of the Genetics Computer Group, Madison Wis.) that incorporates the Needelman and Wunsch, (*J. Mol. Biol.*, 48: 443-453, 1970) algorithm (e.g., NBLAST, and XBLAST). The default parameters are used to determine the identity for the polypeptides.

By way of example, a polypeptide sequence may be identical to the reference sequence, that is be 100% identical, or it may include up to a certain integer number of amino acid alterations as compared to the reference sequence such that the percent identity is less than 100%. Such alterations are selected from at least one amino acid deletion, substitution, including conservative and non-conservative substitution, or insertion, and wherein the alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given percent identity is determined by multiplying the total number of amino acids in the reference polypeptide by the numerical percent of the respective percent identity (divided by 100) and then subtracting that product from said total number of amino acids in the reference polypeptide.

The term "percent (%) sequence identity" is defined as the percentage of nucleotides or amino acids in a candidate sequence that are identical with the nucleotides or amino acids in a reference nucleic acid or polypeptide sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

As used herein, the term "recombinant polynucleotide" generally refers to a polynucleotide obtained through genetic engineering techniques.

As used herein, the term "recombinant polynucleotide" generally refers to a polypeptide obtained from a recombinant polynucleotide. A recombinant nucleic acid or polypeptide is one that has a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques. A recombinant polypeptide can also refer to a polypeptide that has been made using recombinant nucleic acids, including recombinant nucleic acids transferred to a host organism that is not the natural source of the polypeptide.

As used herein, the term "purified" and like terms relate to the molecule or compound in a form that is substantially free (at least 60% free, preferably 75% free, and most preferably 90% free) from other components normally associated with the molecule or compound in a native environment.

As used herein, the term "fusion polypeptide" refers to a polypeptide formed by the joining of two or more polypeptides through a peptide bond formed between the amino terminus of one polypeptide and the carboxyl terminus of another polypeptide, or through linking of one polypeptide to another through amino acid linkers, or reactions between amino acid side chains (for example, disulfide bonds between cysteine residues on each polypeptide). The fusion protein can be formed by the chemical coupling of the constituent polypeptides or it can be expressed as a single polypeptide from a nucleic acid sequence encoding the single contiguous fusion protein. Fusion proteins can be prepared using conventional techniques in molecular biology to join the two genes in frame into a single nucleic acid sequence, and then expressing the nucleic acid in an appropriate host cell under conditions in which the fusion protein is expressed.

As used herein, the term "monomer" refers to a single fusion polypeptide molecule. As used herein, the terms "dimers", "trimers", "tetramers", or "multimers" refer to two, three, four, or more monomers, respectively, forming one polypeptide molecule. The dimers, trimers, tetramers, or multimers may be homodimers, homotrimers, homotetramers, or homomultimers containing the same amino acid sequences for each of the monomers forming the dimers, trimers, tetramers, or multimers. The dimers, trimers, tetramers, or multimers may be heterodimers, heterotrimers, heterotetramers, or heteromultimers containing different amino acid sequences for each of the monomers forming the dimers, trimers, tetramers, or multimers.

As used herein, the term "solubility" refers to maximum concentration of the polypeptide or conjugate in a physiological buffer, at physiological pH and room temperature, at which the polypeptide or conjugate does not substantially aggregate. Solubility and/or aggregation may be detected by chromatography, gel electrophoresis, or melting/aggregations analyses.

As used herein, the term "half-life in vivo" generally refers to a half of the maximum time the polypeptide or conjugate is retained in circulation in vivo. The half-life in vivo may be measured by activity assays specific to the polypeptide or conjugate after obtaining plasma samples at different time intervals from a subject administered the polypeptide or conjugate. The half-life in vivo may be measured by detection assays detecting the presence of the polypeptide or conjugate in plasma samples obtained at different time intervals from a subject administered the polypeptide or conjugate.

As used herein, the term "nucleic acid" refers to any natural or synthetic linear and sequential arrays of nucleotides and nucleosides, for example, DNA including complementary DNA (cDNA), replicating RNA (repRNA), and messenger RNA (mRNA). The term "nucleic acid" further includes modified or derivatized nucleotides and nucleosides such as, but not limited to, halogenated nucleotides such as 5-bromouracil, and derivatized nucleotides such as biotin-labeled nucleotides.

As used herein, the term "polynucleotide" refers to a single molecule including one or more nucleic acid molecules, wherein each nucleic acid molecule encodes for a different protein and/or performs a different function in an expression vector. The polynucleotide may be in an expression vector, such as in a plasmid, cosmid, or a viral vector.

As used herein, the term "expression vector" refers to a recombinant genetic molecule having one or more isolated polynucleotide sequences. Expression vectors used for polynucleotide expression in a host organism include in the 5'-3' direction, a promoter sequence; a sequence encoding a polynucleotide of interest; and a termination sequence. The vector may also include selectable marker gene(s) and other regulatory elements for expression. The vector may be suitable for expression in prokaryotic cells, such as E. coli, or in eukaryotic cells, such as in yeast cells or mammalian cells.

As used herein, the term "host", "subject" or "patient" refers to any individual who is the target of administration.

As used herein, the term "immunogenicity", in the context of a polypeptide, conjugate, or a composition refers to a polypeptide, a conjugate, or a composition that can induce an immune response and is therefore antigenic. By "immune response" means any reaction by the immune system. These reactions include the alteration in the activity of an organism's immune system in response to a polypeptide, polynucleotide, conjugate, or compositions thereof, and can involve, for example, antibody production, induction of cell-mediated immunity, complement activation, or development of immunological tolerance.

As used herein, the phrase "substantially lower immunogenicity" specifies a reduction or inhibition of immunogenicity score of greater than at least about 25%, at least about 20%, at least about 15%, at least about 12.5%, at least about 10%, or at least about 5%, relative to the immunogenicity of a corresponding polypeptide or a corresponding conjugate in a host predicted by the in silico modeling, or in immune cells ex vivo.

As used herein, the term "corresponding polypeptide" refers to a polypeptide formed generally of similar first sequence and/or similar second sequence as a reference polypeptide, but without the modifications of the reference polypeptide.

As used herein, the term "corresponding conjugate" refers to a conjugate formed generally of the same or similar first sequence and/or the same or similar second sequence as a reference conjugate, but without the modifications of the reference conjugate.

As used herein, the term "treating" includes inhibiting, alleviating, preventing or eliminating one or more symptoms or side effects associated with the disease, condition, or disorder being treated.

The term "reduce", "inhibit", "alleviate" or "decrease" are used relative to a control. One of skill in the art would readily identify the appropriate control to use for each experiment. For example, a decreased response in a subject or cell treated with a polypeptide is compared to a control, such as to a response in subject or cell that is not treated with the polypeptide, or treated with a corresponding polypeptide or corresponding conjugate. The decrease may be a complete inhibition or reduction of in activity, expression, or a symptom, or a partial inhibition or reduction. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% reduction in activity, expression, or a symptom relative to a control.

As used herein the term "effective amount" or "therapeutically effective amount" means a dosage sufficient to treat, inhibit, or alleviate one or more symptoms of a disease state being treated or to otherwise provide a desired pharmacologic and/or physiologic effect. The precise dosage will vary according to a variety of factors such as subject-dependent variables (e.g., age, immune system health, etc.), the disease or disorder, and the treatment being administered. The effect of the effective amount can be relative to a control. Such controls are known in the art and discussed herein, and can be, for example, the condition of the subject prior to or in the absence of administration of the drug, or drug combination, or in the case of drug combinations, the effect of the combination can be compared to the effect of administration of only one of the drugs.

As used herein, the term "combination therapy" refers to treatment of a disease or symptom thereof, or a method for achieving a desired physiological change, including administering an effective amount of two or more chemical agents or components to treat the disease or symptom thereof, or to produce the physiological change, wherein the chemical agents or components are administered together, such as part of the same composition, or administered separately and independently at the same time or at different times (i.e., administration of each agent or component is separated by a finite period of time from each other).

As used herein, the term "dosage regime" refers to a regime of administration of the polypeptide, polynucleotide, conjugate or compositions thereof, route of administration, dose, dosing interval and treatment duration.

As used herein, the term "substantially" refers to comparative measure of at least about 25%, at least about 20%, at least about 15%, at least about 12.5%, at least about 10%, or at least about 5%, relative to a control.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10.

II. Compositions

A. Modified Fusion Polypeptides

Fusion polypeptides contain a modified multimerization domain as a first sequence and a protein of interest as a second sequence. Also described are conjugates of the fusion polypeptides. The conjugates typically include the fusion polypeptide and a half-life extending molecule. The modified multimerization domains provide high expression, solubility, stability, and low immunogenicity to the fusion polypeptides.

TRAIL compositions with the modified multimerization domains show improved physico-chemical and biological properties relative to TRAIL compositions with multimerization domains of the art. The TRAIL compositions also have lower immunogenicity when compared to that of TRAIL compositions with multimerization domains of the art.

Also described are polynucleotides encoding the fusion polypeptides. The polynucleotides may be included in an expression vector. The fusion polypeptides produced through expression of the vector in a prokaryotic or eukaryotic cells may be stored as frozen in the cells, or purified from the cells for further use.

The fusion polypeptides typically include a first sequence and a second sequence. The first sequence is an amino acid sequence of a modified multimerization domain, such as a modified isoleucine zipper (miLZ) domain. The second sequence is an amino acid sequence for a protein or peptide that has a tertiary structure as a dimer, trimer, tetramer, or a multimer. An exemplary protein or peptide is the TRAIL protein monomer, which, in its tertiary structure, is a homotrimer.

1. First Sequence

Typically, the first amino acid sequence includes a modified multimerization sequence for a yeast GCN4-pII leucine zipper (LZ). The art recognizes the GCN4-pII modified at certain amino acid locations to substitute leucine (Leu (L)) with isoleucine (Ile (I)) (Harbury et al, *Nature*, 371:80-83 (1994); Rozanov et al., *Mol Cancer Ther*, 8:1515-1525 (2009)), forming isoleucine zipper (iLZ) sequences. The art also recognizes that these modifications and the use of these zipper sequences can be immunogenic in humans (US 2016/0280761).

In the fusion polypeptides described herein, the first sequences typically include modified isoleucine zipper (miLZ) sequences with reduced immunogenicity in mammalian hosts. The modified isoleucine zipper sequences are presented below and, in this section, the modified amino acids are presented at positions relative to:

1) a core sequence (SEQ ID NO:1),
2) a prior art iLZ sequence (SEQ ID NO:2; described in Rozanov et al., *Mol Cancer Ther,* 8:1515-1525 (2009)); and
3) a second prior art iLZ sequence (SEQ ID NO:3).

The prior art LZ and iLZ sequences are represented as:
KQIEDKIEEILSKIYHIENEIARIKKLIGE (SEQ ID NO:1, segment from the modified yeast GCN4-pII leucine zipper (LZ) motif containing isoleucine substitutions at positions 6, 10, 13, 17, 20, 24, 27 and 31 (GRMKQIEDK-IEEILSKIYHIENEIARIKKLIGER, SEQ ID NO:2, iLZ); Harbury et al, *Nature,* 371:80-83 (1994); Rozanov et al., *Mol Cancer Ther,* 8:1515-1525 (2009)), or PGMCGGKQIEDK-IEEILSKIYHIENEIARIKKLIGEDGV (SEQ ID NO:3), iLZ).

For consistency throughout this disclosure, the first sequences are presented with their SEQ ID NOs, and the modified amino acids are presented at positions relative to SEQ ID NO:1.

The first sequence, containing miLZ, typically includes any one of the SEQ ID NOs: 4-8 as a portion of the miLZ:
KQIEDKIEEILSKIYHVENEIARIKELIGE (SEQ ID NO:4; I17V, K26E; or I20V, K29E relative to SEQ ID NO:2, or I23V, K32E relative to SEQ ID NO:3)
KQIEDKIEEILSKIYHVENEIARIKKLIGE (SEQ ID NO:5; I17V, or I20V relative to SEQ ID NO:2, or I23V relative to SEQ ID NO:3)
KQIEDKIEEILSKIYHIENEIARIKQLIGE (SEQ ID NO:6; K26E, or K29E relative to SEQ ID NO:2, or K32E relative to SEQ ID NO:3)
KQIEDKIEEILSKIYHIENEIARIKQLIGE (SEQ ID NO:7; K26Q; K29Q relative to SEQ ID NO:2, or K32Q relative to SEQ ID NO:3)
KQIEDKIEEILSKVYHIENEIARIKELIGE (SEQ ID NO:8; I14V, K26E, or I17V; K29E relative to SEQ ID NO:2, or I17V, K32E relative to SEQ ID NO:3).

The miLZ domains of the fusion polypeptides have modifications of the isoleucine residues at position 17, and the lysine residue at position 26 of the iLZ known in the art (iLZ containing a sequence as shown in SEQ ID NO:1 and miLZ containing a sequence as shown in SEQ ID NO:4-8). These modifications of the prior art iLZ do not affect the multimerization of the fusion polypeptide and produce a TRAIL trimer that is stable, soluble, has an increased half-life in vivo, and reduced immunogenicity. This is contrary to the art showing that the isoleucine residues at these positions (Ile at position 20 of SEQ ID NO:2 (corresponding to position17 in SEQ ID NO:1) were needed and conferred stable trimer formation to TRAIL (Harbury et al, *Nature,* 371:80-83 (1994); Rozanov et al., *Mol Cancer Ther,* 8:1515-1525 (2009), disclosing SEQ ID NO:3).

2. Second Sequence

The second sequence may be an amino acid sequence to a protein or polypeptide that is typically functional as a homo- or hetero-dimer, -trimer, -tetramer, or -multimer. An exemplary second sequence is a full sequence or a fragment, variant, or homolog of the human TRAIL polypeptide.

TRAIL/Apo2L (TNFSF10) was originally identified in searches of EST databases for genes with homology to known TNF superfamily ligands (Benedict et al., *J. Exp. Med.,* 209(11):1903-1906 (2012)). In humans, TRAIL binds to two proapoptotic death receptors (DRs), TRAIL-R1 and —R2 (TNFRSF10A and 10B), as well as to two other membrane receptors that do not induce death and instead may act as decoys for death signaling. TRAIL binding to its cognate DRs induces formation of a death-inducing signaling complex, ultimately leading to caspase activation and initiation of apoptosis (Benedict et al., *J. Exp. Med.,* 209 (11):1903-1906 (2012)).

In some embodiments, the second sequence includes an amino acid sequence of a TRAIL peptide monomer.

Nucleic acid and amino acid sequence for human TRAIL are known in the art. For example, an amino acid sequence for human TRAIL is MAM-MEVQGGPSLGQTCVLIVIFTVLLQSLCVAVTYVYFT-NELKQMQ DKYSKSGI-ACFLKEDDSYWDPNDEESMNSPCWQVKWQLRQ-LVRKM ILRTSEETISTVQEKQQNISPLVRERGPQR-VAAHITGTRGRSNTLSSPN SKNEKALGRKINSW-ESSRSGHSFLSNLHLRNGELVIHEKGFYYIYSQT YFRFQEEIKENTKNDKQMVQYIYKYTSYPDPILL-MKSARNSCWSKD AEYGLYSIYQGGIFELKEND-RIFVSVTNEHLIDMDHEASFFGAFLVG (SEQ ID NO:9, (UniProtKB database accession no. P50591 (TNF10_HUMAN)). In some embodiments, the second sequence includes a TRAIL peptide including or having the amino acid sequence of SEQ ID NO:10.

TRAIL homologs or variants can have at least 50%, at least 60%, at least 70%, at least 80%, at least 90%, at least 95%, at least 98%, at least 99% or 100% identity to SEQ ID NO: 9. A conservative amino acid substitution is a substitution of one amino acid to an amino acid that is similar in structure.

Preferably, the TRAIL is a soluble TRAIL. Endogenous, full-length TRAIL includes a cytoplasmic domain, a transmembrane domain, and an extracellular domain. Typically, soluble TRAIL is a fragment of full-length TRAIL without the cytoplasmic domain and the transmembrane domain. Therefore, soluble TRAIL can be the extracellular domain of TRAIL (e.g., extracellular domain of SEQ ID NO:9), or a functional fragment thereof. A consensus extracellular domain for the TRAIL of SEQ ID NO:9 is amino acids 39-281 of SEQ ID NO:9 (SEQ ID NO:10). Therefore, in some embodiments, the second sequence includes a TRAIL peptide including or having amino acids 39-281 (SEQ ID NO:10), 41-281 (SEQ ID NO:11), 91-281 (SEQ ID NO:12), 92-281 (SEQ ID NO:13), 95-281 (SEQ ID NO:14), and 114-281 (SEQ ID NO:15) of SEQ ID NO:9, or a functional fragment or variant thereof.

In some embodiments, the second sequence includes a functional fragment or variant of SEQ ID NO:7 that can agonize signaling through TRAIL-R1 and/or TRAIL-R2. The fragment or variant of SEQ ID NO:9 can have 50, 60, 70, 75, 80, 85, 90, 95, 96, 97, 98, 99, or more than 99% sequence identity to SEQ ID NO:9.

Preferably, the functional fragment or variant thereof includes the extracellular domain of SEQ ID NO:9, or a functional fragment thereof. It is believed that the C-terminal 150 amino acid of TRAIL includes the receptor binding domain. Therefore, in some embodiments, the functional fragment includes amino acids 132-281 of SEQ ID NO:9 (SEQ ID NO:16). In other particular embodiments, the fragment is amino acids 95-281 of SEQ ID NO:9 (SEQ ID NO:14), or amino acids 114-281 of SEQ ID NO:9 (SEQ ID NO:15).

Variants can have one or more substitutions, deletions, or additions, or any combination thereof relative to SEQ ID NOs:9-15. In some embodiments, the variant is a naturally occurring alternative sequence, splice variant, or substitution, addition or deletion variant, or the extracellular domain or function fragment thereof or an alternative sequence, splice variant, or substitution, addition or deletion variant.

Naturally occurring alternative sequences and variants are disclosed in UniProtKB database accession no. P50591 (TNF10_HUMAN), version 140 (last modified Jan. 22, 2014).

a. TRAIL Analogues

TRAIL can interact with its receptors as a trimer. In some embodiments, the second sequence can form a multimer, preferably a trimer. The trimer can be a homotrimer or a heterotrimer.

All of the TRAIL proteins described herein can be made using standard techniques for isolation of natural or recombinant proteins, and chemically modified as described herein.

The second sequence can include a TRAIL analogue, or an agonistic TRAIL receptor binding fragment or variant thereof. TRAIL analogues are known in the art. In preferred embodiments, the analogues have increased affinity or specificity for one or more agonistic TRAIL receptors (e.g., TRAILR1 (DR4) and/or TRAIL-R2 (DR5)), reduced affinity or specificity for one or more antagonistic or decoy TRAIL receptors (e.g., receptors DcR1 and DcR2) or a combination thereof compared to wild-type or endogenous TRAIL.

In some embodiments, the analogue is a DR4-selective mutant of wild-type TRAIL. DR-4 selective mutants are known in the art and described in, for example, Tur, *J. Biological Chemistry*, 283(29):20560-8 (2008). In particular embodiments, the analogue is a variant of SEQ ID NO:9 having a D218H (SEQ ID NO: 17) or a D218Y (SEQ ID NO:18) substitution, or a functional fragment thereof (e.g., the extracellular domain).

In some embodiments, the analogue is a DR5-selective mutant of wildtype TRAIL. Particular DR-5-selective mutants include variants of SEQ ID NO:9 having D269H (SEQ ID NO:19), D269H/E195R (SEQ ID NO:20), or D269H/T214R (SEQ ID NO:21), and functional fragments thereof (e.g., the extracellular domain). Such variants are described in van der Sloot, *Proc. Nat. Acad. Sci. USA* 103(23):8634-9 (2006).

b. Other TRAIL Analogs

In still further examples, the second sequence includes one or more stabilizing mutations such as S133P (SEQ ID NO:22), S156C (SEQ ID NO:23), L196C (SEQ ID NO:24), T127C (SEQ ID NO:25), or H270C (SEQ ID NO:26) to the native TRAIL sequence, SEQ ID NO:9. Examples of sequences with such mutations include SEQ ID NOs: 21-26.

Typically, the second amino acid sequence includes a sequence of any one of SEQ ID NOs: 9-26.

3. Linker

The first sequence may be fused with the second sequence with or without a linker.

The linker may be amino acid linker, such as an amino acid linker having a length between one and four or between one and six, amino acids. Exemplary amino acid linkers include D, G, DG, KGSG (SEQ ID NO:27), GSG, SG, and RGSG (SEQ ID NO:28).

4. Expression Sequence

The fusion polypeptides may include expression sequences preceding the first amino acid sequences. The expression sequences may have a length between two and six or between two and eight, amino acids. Exemplary expression sequences include RM, GRM, CGG, PGMCGG (SEQ ID NO:29).

5. Exemplary Fusion Polypeptide

An exemplary fusion polypeptide is presented with SEQ ID NO:30 and contains SEQ ID NO:4 as the first amino acid sequence, SEQ ID NO: 15 as the second amino acid sequence, joined together by DG linker (underlined), and preceded with GRM expression sequence (underlined): GRMKQIEDKIEEILSKIYHVENEIARIKELIGE DGVRERGPQRVAAHIT GTRGRSNTLSSPNSKNEKAL-GRKINSWESSRSGHSFLSNLHLRNGELV IHEK-GFYYIYSQTYFRFQEEIKENTKNDKQMVQYIYKYT-SYPDPILLM KSARNSCWSKDAEYGLYSIYQGGIFELKEND-RIFVSVTNEHLIDMDH EASFFGAFLVG (SEQ ID NO:30, used in Examples as clone #5).

Another exemplary sequence is SEQ ID NO:31: MGRMKQIEDKIEEILSKIYH$\boxed{\text{V}}$ENEIARIK $\boxed{\text{E}}$LIGEDGVRERGPQRVAA HITGTRGRSNTLSSPNSK-NEKALGRKINSWESSRSGHSFLSNLHLRNGELVI HEKGFYYIYSQTYFRFQEEIKENT-KNDKQMVQYIYKYTSYPDPILLMKSAR NSCWSK-DAEYGLYSIYQGGIFELKENDRIFVSVTNEHLIDMD-HEASFFGA FLVG, which shows miLZ sequence having more favorable properties than the iLZ sequence in prior art. This contains SEQ ID NO:4 (in bold) and SEQ ID NO:15 (italic).

An exemplary prior art construct is SEQ ID NO:32: MGHHHHHHHHPGMCGGKQIEDKIEEILSKIYH $\boxed{\text{I}}$ENEIARI$\boxed{\text{K}}$LIGE DGVRERGPQRVAAHITGTR-GRSNTLSSPNSKNEKALGRKINSWESSRSGH SFL-SNLHLRNGELVIHEKGFYYIYSQTYFRFQEEIKENT-KNDKQMVQYIYK YTSYPDPILLMKSARNSCWSKDAEYGLYSIYQG-GIFELKENDRIFVSVTNE HLIDMDHEASFFGAFLVG, containing SEQ ID NO:3 (in bold) and SEQ ID NO:15 (italic) as iLZ and TRAIL sequences, respectively.

Other exemplary fusion polypeptides include polypeptides containing any one of sequence SEQ ID NOs:4-8 in combination with any one of SEQ ID NOs:9-26.

The fusion polypeptides can be dimerized, trimerized, or multimerized. Dimerization, trimerization, or multimerization can occur between or among two or more fusion proteins through dimerization, trimerization, or multimerization domains. Alternatively, dimerization, trimerization, or multimerization of fusion proteins can occur by chemical crosslinking. The dimers, trimers, or multimers that are formed can be homodimeric/homomultimeric or heterodimeric/heteromultimeric.

6. Properties of the Fusion Polypeptides

The fusion polypeptides show improved physico-chemical and biological properties relative to TRAIL compositions with multimerization domains of the art. The fusion polypeptides also have lower immunogenicity when compared to that of TRAIL compositions with multimerization domains of the art.

a. Solubility

Typically, the fusion polypeptides have a solubility of between about 0.2 mg/ml and 30 mg/ml (in physiological buffer, physiological pH, and room temperature). Typically, no substantial or detectable aggregation is observed in solutions containing the fusion polypeptides at a concentration between 0.2 mg/ml and 30 mg/ml. The solutions containing the fusion polypeptides at concentrations of between about 0.2 mg/ml and 30 mg/ml, between about 0.5 mg/ml and 25 mg/ml, between about 0.5 mg/ml and 20 mg/ml, between about 0.5 mg/ml and 15 mg/ml, between about 0.5 mg/ml and 10 mg/ml, or between about 0.5 mg/ml and 5 mg/ml do not show substantial or detectable aggregation of the polypeptide.

b. Stability and Half-life

Typically, the fusion polypeptides have improved stability when stored at 4° C. or frozen. The fusion polypeptides also have improved stability when stored frozen in cells (as frozen cell mass) expressing the fusion polypeptide. The expression cells may produce the fusion polypeptide at a production level of about 1 g of the fusion polypeptides per ml of the cell culture. The expression cells with the fusion polypeptides may be stored for a period of one, two, three, four, five, six, seven, eight, nine, ten, 11, or 12 months or more without substantial loss of the soluble fusion polypeptide when thawed. The fusion polypeptides typically stay stable with repeat freeze-thaw cycles inside the expression cells.

Figure 2A:
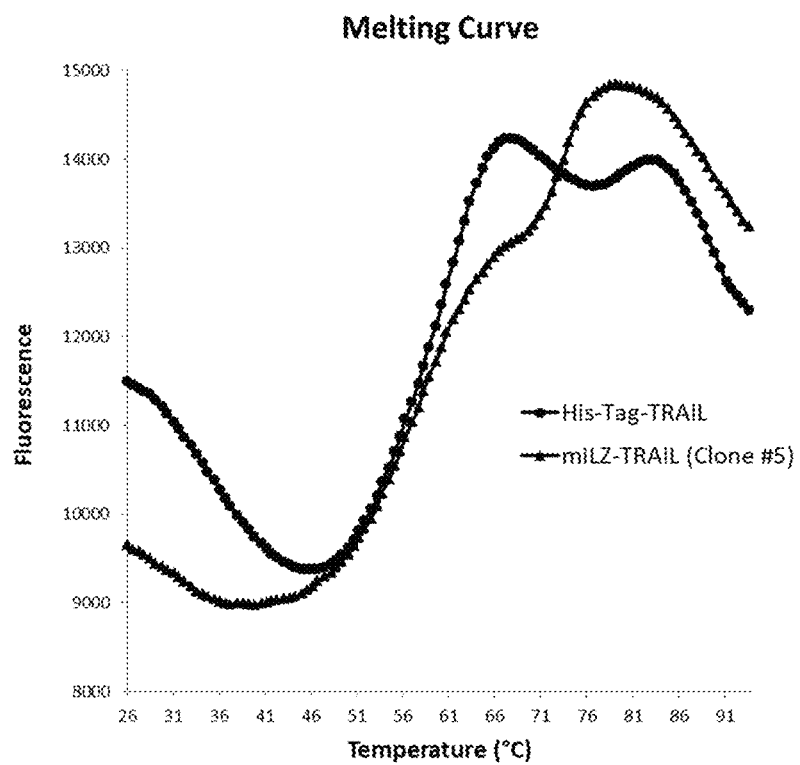
FIG. 2A is a graph showing the melting curve (change in fluorescence over a range of temperatures (25-98° C.)) of a prior art His-TRAIL and miLZ-TRAIL, clone #5, with amino acid sequence as in FIG. 1C.

As shown in the examples below, a fusion polypeptide containing SEQ ID NO: 4 as the first sequence and SEQ ID NO:15 as the second sequence, had a statistically higher thermodynamic stability in a thermal shift assay when compared to the fusion polypeptides in the art having an iLZ motif and a His-tag purification sequence (SEQ ID NO:3 and SEQ ID NO:15; FIG. 2A).

The fusion polypeptides typically have a half-life in vivo between about 1 hour and 36 hours.

c. Biological Activity

Typically, the fusion polypeptides have improved biological activity when compared to the fusion polypeptides in the art having the iLZ motif. Generally, the fusion polypeptides have a half maximal inhibitory concentration (IC50) in vitro between about 0.001 nM and about 0.1 nM, preferably between about 0.001 nM and about 0.05 nM when tested on COLO 205 cells.

The fusion polypeptides typically have at least about 1.5, at least about 2, at least about 3, at least about 4, at least about 5, at least about 6, at least about 7, at least about 8, at least about 9, at least about 10 or more fold higher biological activity (such as IC50) when compared to the fusion polypeptides in the art having an iLZ motif.

Figure 2B:
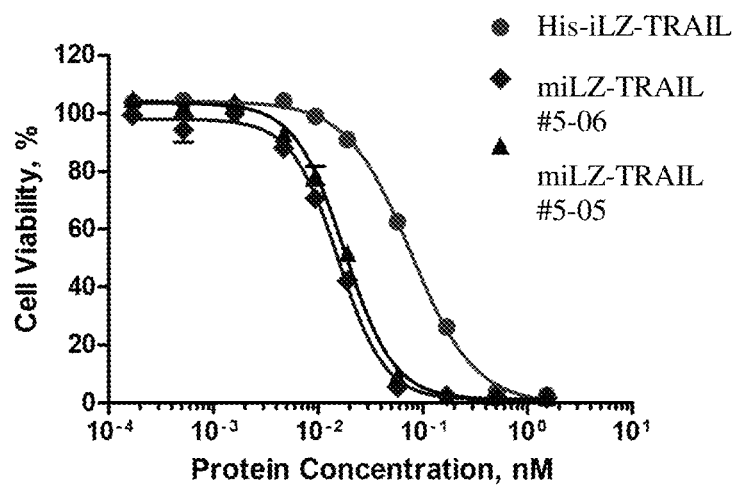
FIG. 2B is a line graph showing the biological activity (a change in cell viability (%) over a range of protein concentrations (nM)) for the prior art His-iLZ-TRAIL and miLZ-TRAIL, clone #5, tested on COLO205 cells.

As shown in the examples below, a fusion polypeptide containing SEQ ID NO: 4 as the first sequence and SEQ ID NO:15 as the second sequence, had about 5-fold higher biological activity in a cell viability assay when compared to a fusion polypeptide including an iLZ motif and a His-tag purification sequence (SEQ ID NO:3 and SEQ ID NO:15; FIG. 2B).

d. Low Immunogenicity

Typically, the modified fusion polypeptides carrying miLZ have a lower immunogenicity in a host when compared to the immunogenicity of unmodified polypeptides carrying iLZ in the same host. Generally, the host is a mammal, preferably, human.

The lower immunogenicity may be a lower immunogenicity score for the modified fusion polypeptides carrying miLZ when compared to that of the unmodified polypeptides carrying iLZ.

For therapeutic applications "immune response" in human subjects is of particular concern as it may cause toxicity, modify or neutralize therapeutic effects of a therapeutic modality such as a polypeptide. In order to predict the immunogenicity of iLZ-TRAIL fusion polypeptide in silico analysis of the primary amino acid sequence has been used. The method is based on a well-established PROPRED model for predicting MHC Class II binding regions in antigenic protein sequences (Singh & Raghava, *Bioinformatics*, v17, N 12, p 1236; and Brison et al., *Biodrugs*, v.24, N 1, p 1, 2010). As the next step of comparing the immunogenicity of the fusion polypeptides with a modified multimerization domain and TRAIL compositions with multimerization domains of the art an in situ test is being performed using the EPISCREEN™ DC: T cell assays provided by ABZENA (San Diego, Calif.). The assays employ dendritic cells (DC) derived from peripheral blood mononuclear cells (PBMCs), typically from 50 individual donors, with a distribution of HLA-DR allotypes (coverage and frequency) representing the human population of interest. The DCs are differentiated to immature DC phenotype and loaded with the test protein. Once matured, the DCs are incubated with autologous CD4+ T cells and markers of T cell activation are measured.

Typically, the modified fusion polypeptides carrying miLZ produce minimal or lower levels of T cell activation markers in a host when compared to the level of T cell activation makers produced by unmodified polypeptides carrying iLZ in the same host, as detected by the EPISCREEN™ DC: T cell assay or an equivalent assay.

The fusion polypeptides typically have at least about 15%, at least about 30%, at least about 50% lower total immunogenicity score when compared to the fusion polypeptide in the art having an iLZ motif (such as SEQ ID NO:3).

For example, two protein sequences of interest were analyzed by Abzena using predictive algorithm iTope-AI to identify peptides that bind to human MHC class II and/or share homology to known T cell epitopes. From this analysis, it was determined that SEQ ID NO:32 (contains SEQ ID NO:3 and SEQ ID NO:15) and SEQ ID NO:31 (contains SEQ ID NO:4 and SEQ ID NO:15) had a Total Score of 27 and 5 respectively, with none of the peptide sequences matching a T cell epitope from the TCED™ (Abzena database).

SEQ ID NO:31 contains miLZ sequence with more favorable properties than the iLZ sequence in SEQ ID NO:32, shown below) and has a significantly better Total Score (5 vs 27) which matches the best scores of monoclonal human antibodies.

The low immunogenicity of miLZ-TRAIL conjugates in general is comparable to the immunogenicity of therapeutic human proteins such as monoclonal human antibodies. Thus the total MHCII-binding score in silico for miLZ-TRAIL (SEQ ID 4 and SEQ ID 15) is comparable or better than the immunogenicity of typical human monoclonal antibodies. The lower immunogenicity of miLZ-TRAIL, as compared to iLZ-TRAIL, is several-fold reduced Total Score (5 vs 27) for MHCII binding in silico. Typically, the immunogenicity of the modified fusion polypeptides is reduced by at least about 1.5, 2, 3, 4, 5, 6, 7, 8, 9, 10, or more fold, preferably between about 2 and 10 fold.

B. Fusion Peptide Conjugates

The fusion polypeptides may be conjugated to one or more half-life extending molecules. The conjugates are typically stable conjugates and do not release the half-life extending molecules in vivo.

1. Half-Life Extending Molecules

The use of hydrophilic polymers such as polyalkylene oxides or copolymers thereof such as the PLURONIC®s sold by BASF can be covalently bound to the fusion polypeptides to improve their pharmacokinetic and pharmacodynamic profiles (Kim, et al., *Bioconjugate Chem.*, 22 (8), pp 1631-1637 (2011)).

In other embodiments, the fusion polypeptides can be derivatized as a long-acting with an extended half-life using biopolymers or polypeptides through reported methods, for example, but not limited to, using chemically conjugated hyaluronic acid (Yang et al., *Biomaterials*, 32(33):8722-8729 (2011), depot forming polypeptides (Amiram et al., *Proc Natl Acad Sci USA*, 110(8):2792-2792 (2013), U.S. Published Application No. US 2013/0178416 A1) and the fusion polypeptides linked to extended recombinant polypeptides (U.S. Published Application No. US 2010/0239554 A1).

2. Fusion Polypeptide-PEG Conjugates

The fusion polypeptides may be stably conjugated with one or more molecules of PEG.

Studies show that TRAIL analogues derivatized with PEG maintain anti-cancer activity (such as induction of apoptosis in cancer cells) while also exhibiting higher metabolic stabilities in plasma, extended pharmacokinetic profiles, and greater circulating half-lives (Chae, et al., *Molecular cancer therapeutics* 9(6):1719-29 (2010); Kim, et al., *Bioconjugate chemistry*, 22(8):1631-7 (2011a); Kim, et al., *Journal of pharmaceutical sciences* 100(2):482-91 (2011b); Kim, et al., *Journal of controlled release: official journal of the Controlled Release Society* 150(1):639 (2011c)).

Therefore, in some embodiments, the fusion polypeptide is derivatized with one or more ethylene glycol (EG) units, more preferably 2 or more EG units (i.e., polyethylene glycol (PEG)), or a derivative thereof. Derivatives of PEG include, but are not limited to, methoxypolyethylene glycol succinimidyl propionate, methoxypolyethylene glycol N-hydroxysuccinimide, methoxypolyethylene glycol aldehyde, methoxypolyethylene glycol maleimide, and multiple-branched polyethylene glycol.

The precise number of EG or derivative units depends on the desired activity, plasma stability, and pharmacokinetic profile. For example, Kim, et al. (Kim et al., 2011a) reported that 2K, 5K, 10K, 20K, and 30K-PEG-TRAIL resulted in greater circulating half-lives of 3.9, 5.3, 6.2, 12.3, and 17.7 h respectively in mice, versus 1.1 h for TRAIL. In some embodiments, the molecular weight of the PEG is between about 1 and 100 kDa. For example, the PEG can have a molecular weight of "N" kDa, wherein N is any integer between 1 and 100. The PEG can have a molecular weight of "N" Da, wherein N is any integer between 1,000 and 1,000,000. In a particular embodiment, the molecular weight of the PEG is "N" Da, wherein "N" is between 5,000 and 50,000, preferably 5,000.

The fusion polypeptide can be conjugated with linear or branched PEG. Some studies have shown that proteins derivatized with branched PEG have extended in vivo circulation half-lives compared to linear PEG-proteins, thought to be due partly to a greater hydrodynamic volume of branched PEG-proteins Fee, et al., *Biotechnol Bioeng.*, 98(4):725-3 (2007).

Peptide ligands can be derivatized at the C-terminus, or preferably at the N-terminus, using methods that are known in the art.

The conjugates may be depicted by the following formula:

X-L-(PEG)$_n$, wherein

X represents a TRAIL protein or TRAIL fusion polypeptide,

L represents a linker,

PEG represents a linear or branched poly(ethylene glycol) chain, and n is an integer selected from 2, 3, 4, 5, 6, 7 or 8.

In certain embodiments, n is 2.

The polyalkylene oxide is coupled to the protein via a linker. The linker may be a polyakylene oxide, and preferably connects two polyalkylene oxide polymers to the protein.

In a particular embodiment, the fusion polypeptide conjugate is a PEG-conjugate that includes a TRAIL domain including a truncated form of human TRAIL, for example, from arginine-114 to glycine-281 of the full-length form (1-281) of human TRAIL, and PEG having a molecular weight between 1,000 and 100,000 Daltons, and preferably between 5,000 and 100,000 Daltons, such as between 5,000 and 80,000 Daltons, between 5,000 and 60,000 Daltons, or between 5,000 and 40,000 Daltons.

N-terminal modified PEG-TRAIL conjugates can be obtained by reacting an N-terminal amine of the TRAIL domain with an aldehyde group of the PEG in the presence of a reducing agent. PEG and TRAIL can be reacted at a molar ratio (PEG/TRAIL) of 2 to 50, or preferably 5 to 7.5. Both linear or branched PEG molecules may be used.

The PEG chains are preferably, but not necessarily, of equal molecular weight. Exemplary molecular weight ranges for each PEG chain is between about 10 kDa and 60 kDa, and preferably about 20 kDa and 40 kDa. PEG40 is a branched PEG moiety was synthesized and has a molecular weight of 40 kDa: 20+20 kDa (each PEG chain).

A trimeric PEG moiety can consist of a branched PEG chain attached to a linker arm. A visual description of the trimer PEG moiety is provided immediately below.

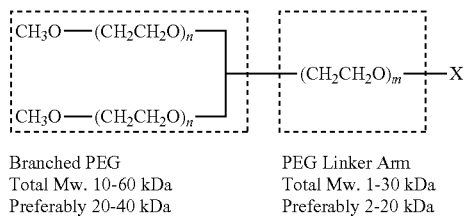

Branched PEG
Total Mw. 10-60 kDa
Preferably 20-40 kDa

PEG Linker Arm
Total Mw. 1-30 kDa
Preferably 2-20 kDa

The following trimeric PEGs were synthesized: YPEG42, YPEG43.5, YPEG45, YPEG50 and YPEG60.

YPEG42 is a trimeric PEG moiety which has a molecular weight of 42 kDa: (20+20 kDa) (branched PEG)+2 kDa (linker arm).

YPEG43.5 is a trimeric PEG moiety which has a molecular weight of 43.5 kDa: (20+20 kDa) (branched PEG)+3.5 kDa (linker arm).

YPEG45 is a trimeric PEG moiety which has a molecular weight of 45 kDa: (20+20 kDa) (branched PEG)+5 kDa (linker arm).

YPEG50 is a trimeric PEG moiety which has a molecular weight of 50 kDa: (20+20 kDa) (branched PEG)+10 kDa (linker arm).

YPEG60 is a trimeric PEG moiety which has a molecular weight of 60 kDa: (20+20 kDa) (branched PEG)+20 kDa (linker arm).

a. Linker Moiety

The fusion polypeptide may be covalently joined to the PEG moiety via a linker. The linker is a polymer, and generally has an atomic length of at least 800 angstroms. Typically, the linker has an atomic length from about 800 to about 2,000 angstrom, from about 800 to about 1,500 angstrom, from about 800 to about 1,000 angstrom, or from about 900 to about 1,000 angstrom. The atomic distances refer to fully extended polymers, and that when in the solid state or solution the linker may fold or curl in ways such that the actual distance between the branched PEG and protein or peptide is less than the atomic lengths listed above.

In certain embodiments, the linker is a poly(ethylene glycol) derivative with a molecular weight between about 1 kDa to 30 kDa, preferably from about 2 kDa to 20 kDa. A linker may also be a natural or unnatural amino acid of at least 80 units in length.

PEG alternatives for the linker may include synthetic or natural water-soluble biocompatible polymers such as polyethylene oxide, polyvinyl alcohol, polyacrylamide, proteins such as hyaluronic acid and chondroitin sulfate, celluloses such as hydroxymethyl cellulose, polyvinyl alcohol, and polyhydroxyalkyl (meth)acrylates.

The fusion polypeptide may be covalently bound to the linker using conventional chemistries. Primary amine groups, such as found at the N-terminus or in lysine residues, will react with aldehydes and their equivalents under reductive conditions to give amines (Molineux, *Current pharmaceutical design*, 10(11):1235-1244 (2004)). Mercapto (—SH) groups, such as found in cysteine residues, can undergo a conjugate addition with a variety of Michael acceptors, including acrylic and methacrylic acid derivatives, as well as maleimides (Gong et al., *British Journal of Pharmacology*, 163(2):399-412 (2011)). Other suitable nucleophilic groups found in peptides and proteins include disulfide bonds (Brocchini, et al., *Nature protocols*, 1:2241-2252 (2006)) and histidine residues (Cong, et al., *Bioconjugate Chemistry*, 23(2):248-263 (2012)) in the fusion polypeptide.

The linker can be covalently joined to the protein or peptide using conventional chemistries. For instance, the linker polymer may be derivatized at one end with an electrophilic group such as an aldehyde, epoxide, halogen (chlorine, bromide, iodine), sulfonate ester (tosylate, mesylate), Michael acceptor, or activated carboxylates and then reacted with a nucleophilic amine or thiol group in the protein or peptide. Suitable Michael acceptors include acylic and methacrylic acid derivatives such as acrylamides, methacrylamides, acrylates and methacrylates, as well as maleimides. Suitable activated carboxylates include nitrophenyl carbonate and NHS (N-hydroxy succinate) esters. In other embodiments, peptides and proteins containing arginine residues may be covalently joined with a linker containing a reactive 1,3 diketone functional group.

The conjugates may be prepared by first joining the linker with the fusion polypeptide, followed by joining the linker with the branched poly(ethylene glycol), or by first joining the linker with the branched poly(ethylene glycol), followed by joining the linker with the fusion polypeptide. The optimal sequence of bond formation is determined by the specific chemical transformations involved.

3. Properties of Conjugates

The long-acting fusion polypeptide-PEG conjugates have a lower immunogenicity when compared to that of the conjugates with iLZ domains of the art. Typically, the long-acting conjugates have increased solubility, lower immunogenicity, and significantly improved potency over the long-acting conjugates of the art.

a. Solubility

Typically, the conjugates have a solubility of between about 0.2 mg/ml and 50 mg/ml (in physiological buffer, physiological pH, and room temperature). Typically, no substantial or detectable aggregation is observed in solutions containing the conjugates at a concentration between 0.2 mg/ml and 50 mg/ml. The solutions containing the conjugates at concentrations of between about 0.2 mg/ml and 50 mg/ml, between about 0.2 mg/ml and 40 mg/ml, between about 0.2 mg/ml and 30 mg/ml, or between about 0.2 mg/ml and 25 mg/ml, generally do not show a substantial or detectable aggregation of the conjugate.

b. Stability and Half-life

Typically, the conjugates have improved stability when stored at 4° C. in the presence of physiological concentrations of salt or when frozen. The conjugates are typically stable with repeat freeze-thaw cycles without substantial loss of bioactivity.

The stability may be evaluated by measuring the ratio of soluble material to the insoluble material that can be separated by centrifugation. The intact structure of stored material can also be confirmed by IEX-HPLC (SP-NPR) and RP-HPLC (C4).

As presented in Example 5 below, an exemplary conjugate containing SEQ ID NO: 4 as the first sequence and SEQ ID NO:15 as the second sequence, at a concentration of 21-22 mg/ml, was resistant to multiple freeze-thaw cycles both in term of biological activity and the appearance in HPLC analysis. This example shows that an exemplary fusion polypeptide-PEG conjugate is highly soluble and stable to repeat freeze-thaw cycles.

The fusion polypeptides typically have a half-life in vivo between about 20 hours and about 50 hours in non-human primates, between about 20 hours and about 40 hours, or between about 25 hours and about 40 hours in non-human primates.

The half-life ($t_{1/2}$) of His-iLZ-TRAIL (containing SEQ ID 3 and SEQ ID 15) injected IV into monkeys was 0.9 h as compared to the $t_{1/2}$ of 8.6 h observed for the same protein after PEGylation (*Hepatology*, 64(1): 209-223 (2016)). The PEGylated iLZ TRAIL variants, with circulation $t_{1/2}$ exceeding the $t_{1/2}$ of non-PEGylated TRAIL by several fold, are considered long-acting conjugates. The Examples below demonstrate that PEGylated miLZ TRAIL has several fold greater tin, (about 20 hours, about 30 hours, about 40 hours, such as between 15 hours and 50 hours) than the $t_{1/2}$ for the PEGylated iLZ TRAIL (8.6 h).

c. Biological Activity

Figure 4:
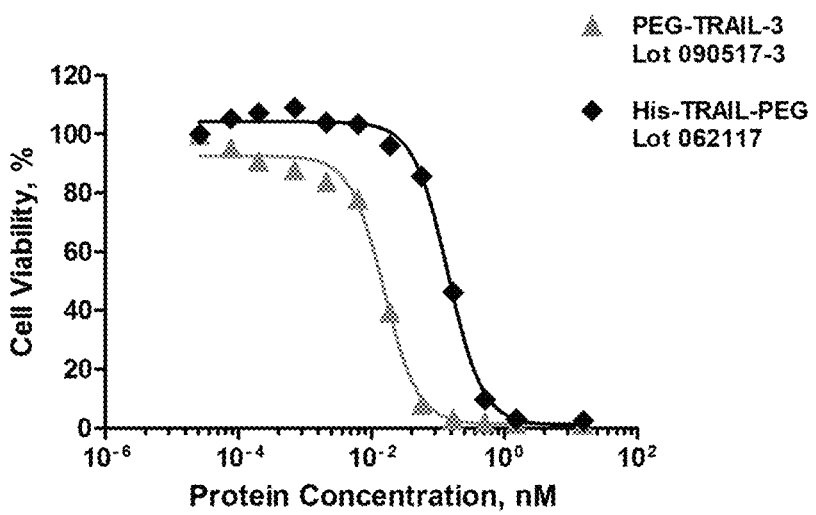
FIG. 4 is a line graph showing the cytotoxicity (a change in cell viability (%) over a range of protein concentrations (nM)) for the PEGylated His-iLZ-TRAIL (His-TRAIL-PEG, containing SEQ ID NO:3 and SEQ ID NO:15, as in SEQ ID NO:32) and PEGylated miIL-TRAIL (containing SEQ ID NO:4 and SEQ ID NO:15, as in SEQ ID NO:31) tested on COLO-205 colorectal cancer cells.
Figure 5A:
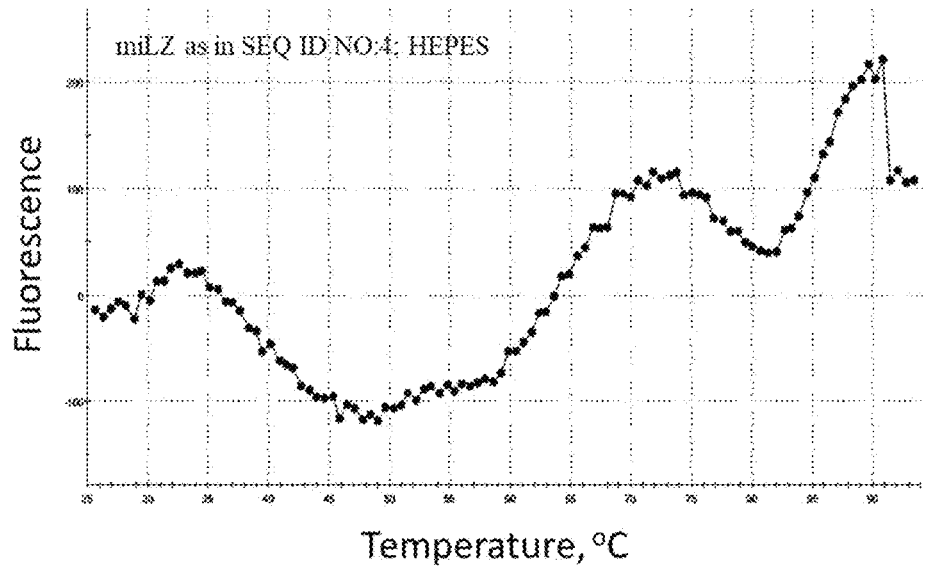
FIGS. 5A-5H are graphs showing change in fluorescence (−R*[T]) over a range of temperatures (25-98° C.) as stability profiles in 30 mM Hepes, 1 M NaCl, 5 mM DTT (pH 8.0) (FIGS. 5A-5D) or in 50 mM MES, 0.5 M NaCl, 5 mM DTT (pH 6.0) (FIGS. 5E-5H) for miLZ-TRAIL 1876 (I23V, K32E) containing SEQ ID NO:4 (FIGS. 5A and 5E); iLZ-TRAIL 1877 containing SEQ ID NO:3 (FIGS. 5B and 5F); miLZ-TRAIL 1878 (K32E) containing SEQ ID NO:6 (FIGS. 5C and 5G); and miLZ-TRAIL 1879 (K32Q) containing SEQ ID NO:7 (FIGS. 5D and 5H).
Figure 5B:
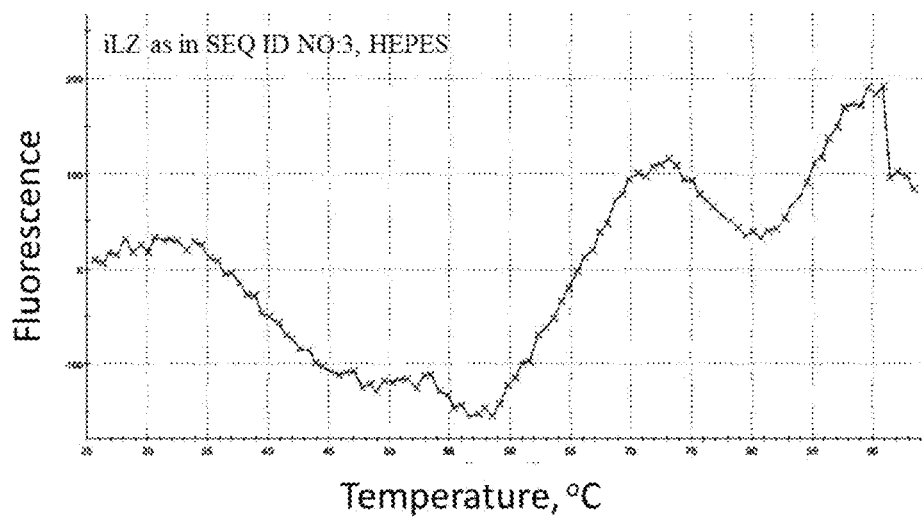
Figure 5C:
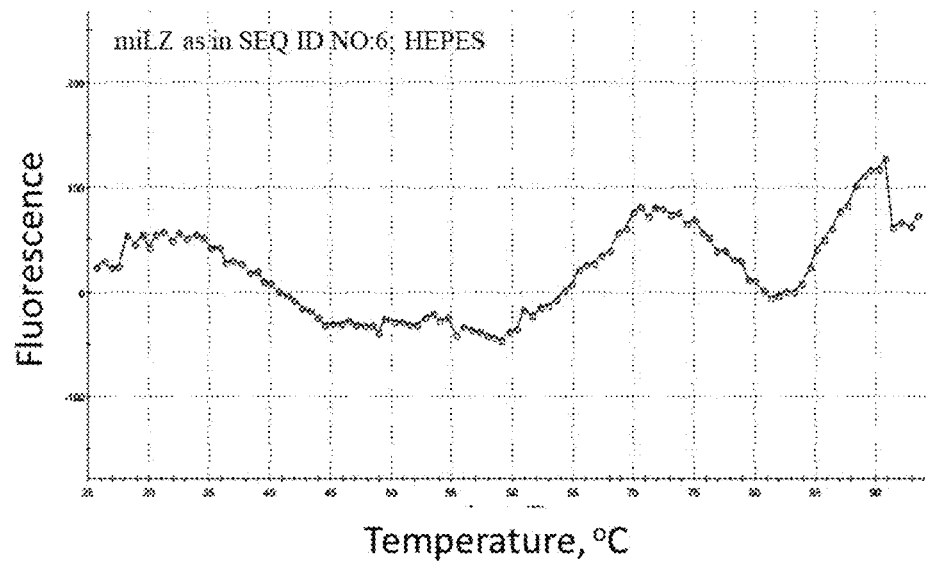
Figure 5D:
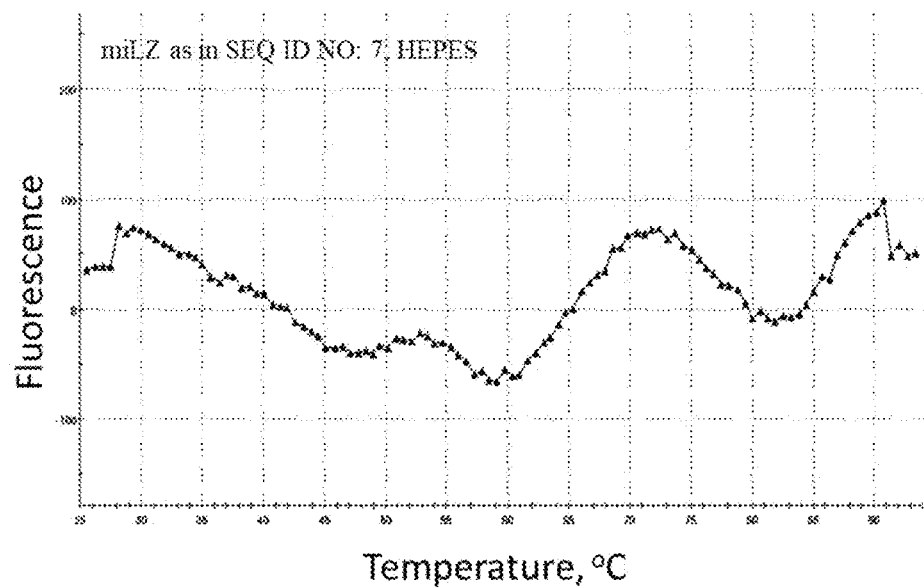
Figure 5E:
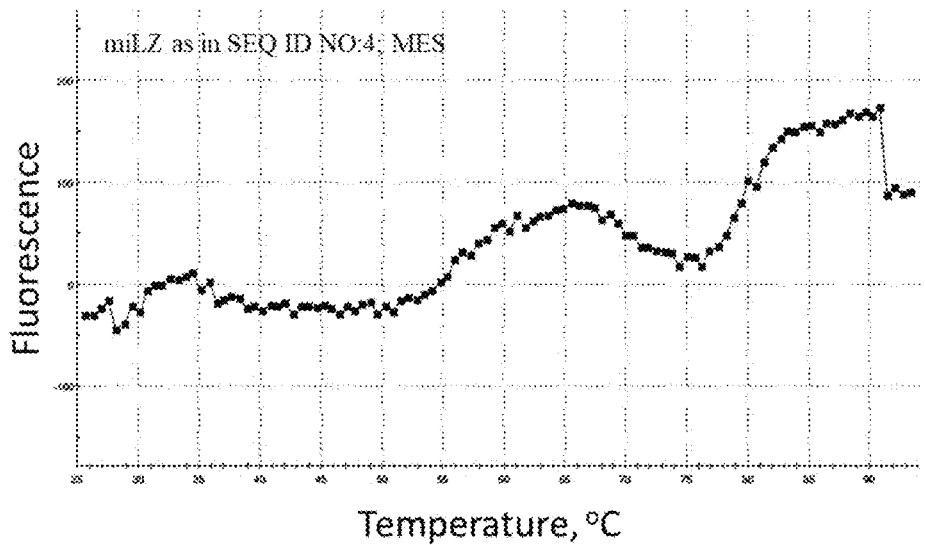
Figure 5F:
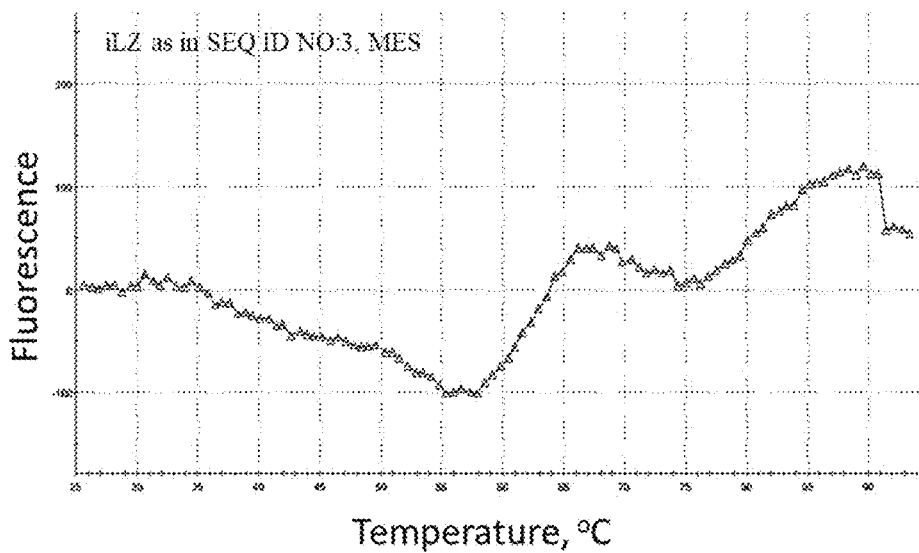
Figure 5G:
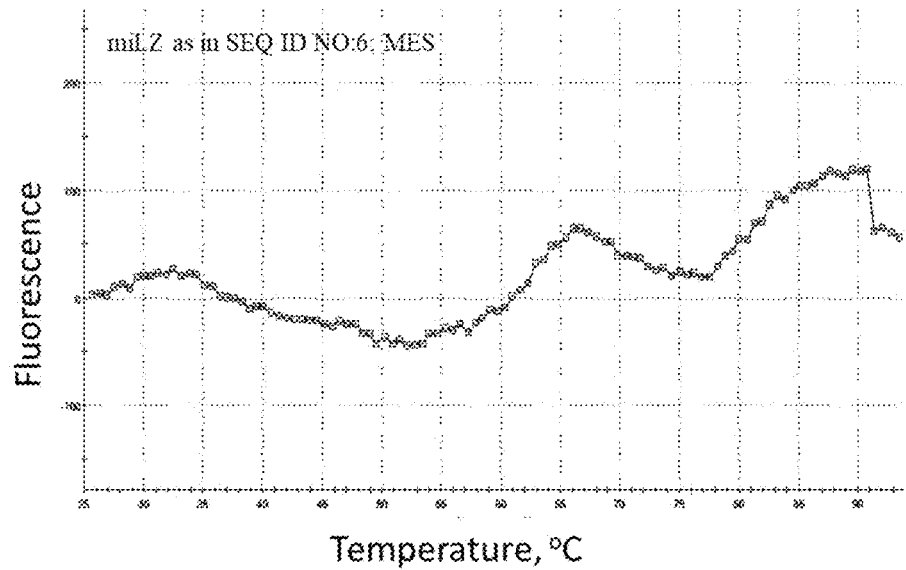
Figure 5H:
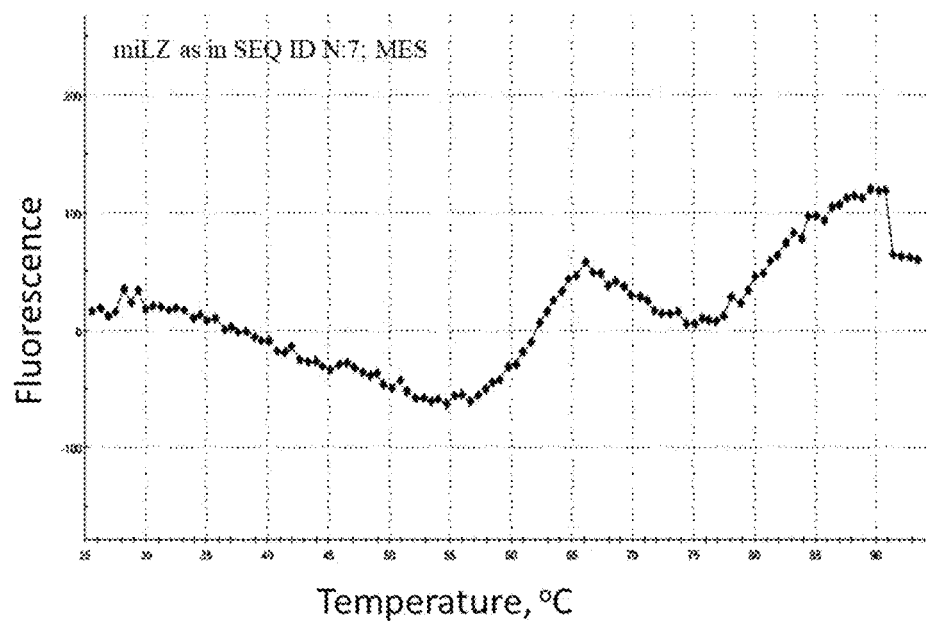
Figure 7A:
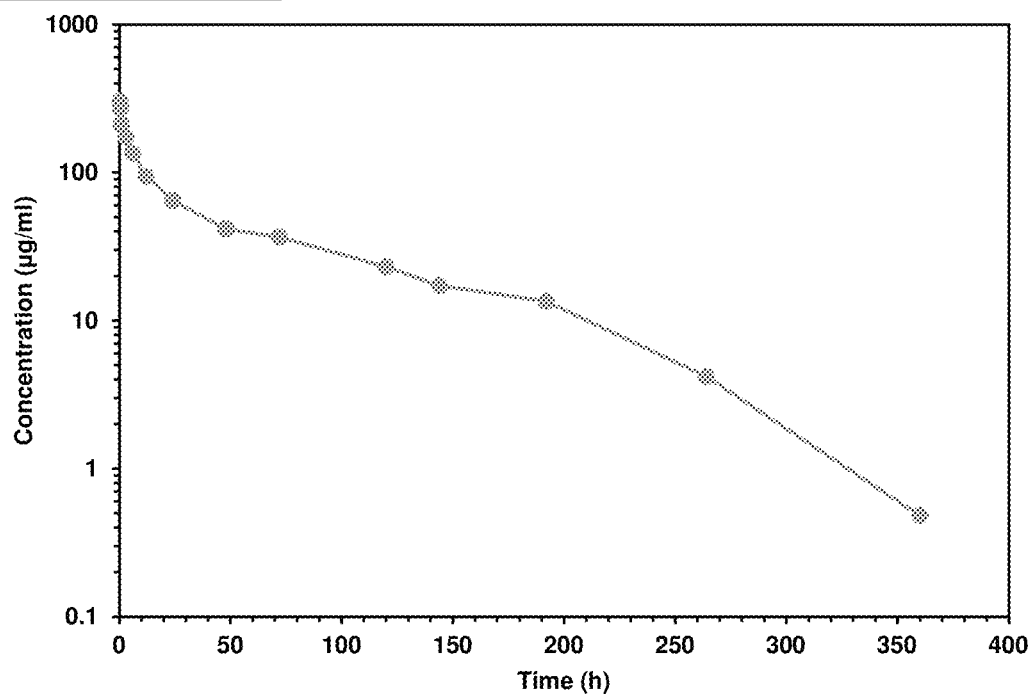
FIGS. 7A-7D are graphs showing change in serum concentration of TLY012 over time (hours) when injected intravenously (IV, at 10 mg/kg, FIG. 7A), or subcutaneously (SC, at 2 mg/kg or 10 mg/kg, FIGS. 7B and 7C), or 50 mg/kg (FIG. 7D).
Figure 7B:
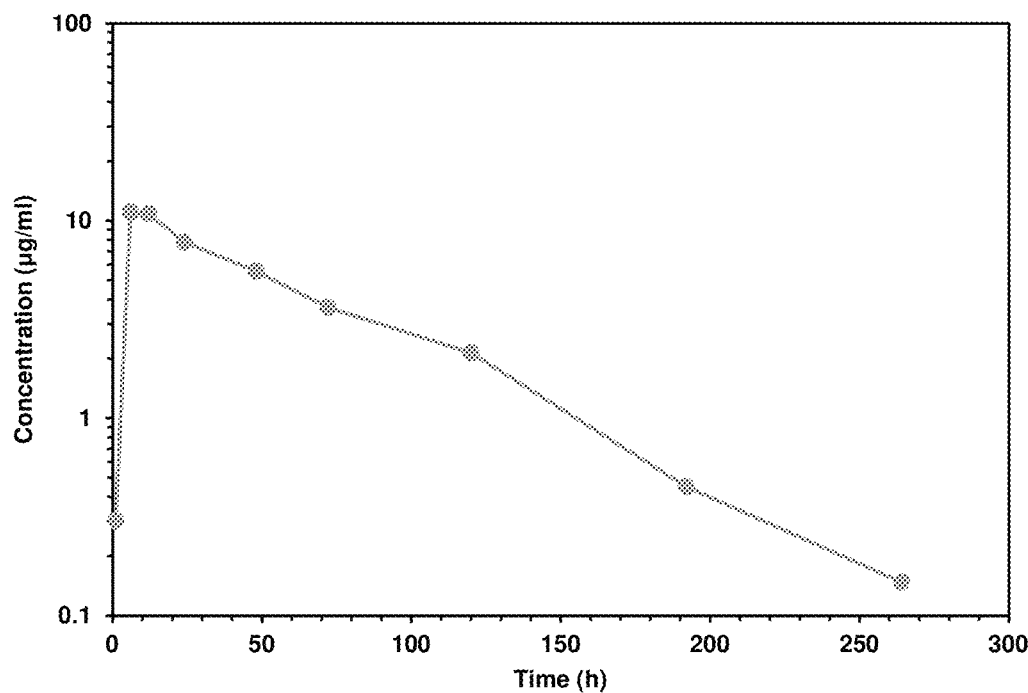
Figure 7C:
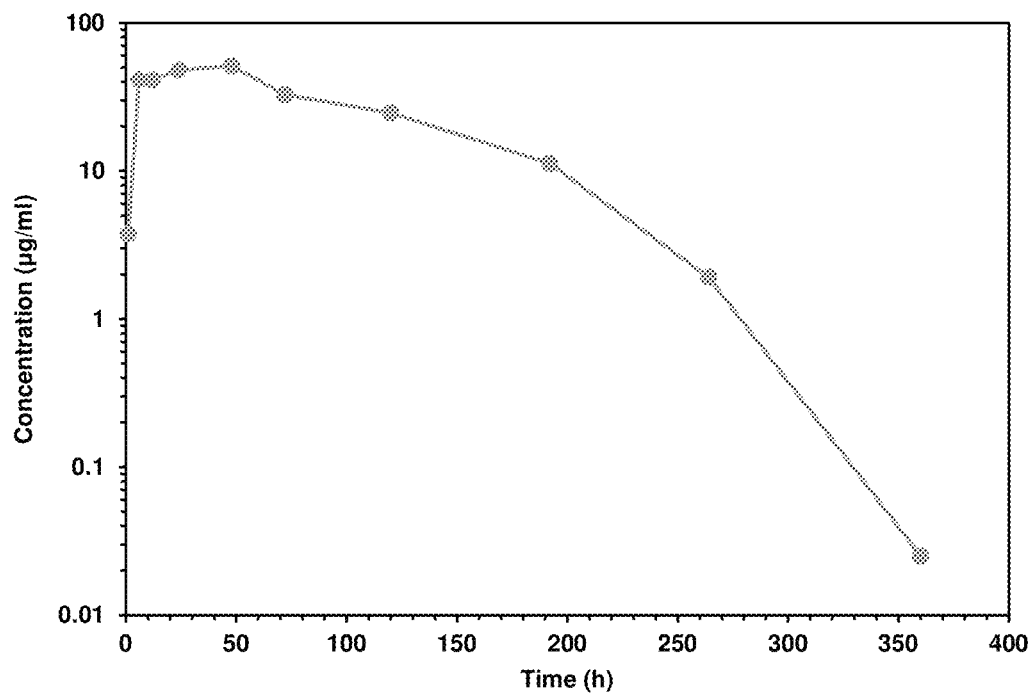
Figure 7D:
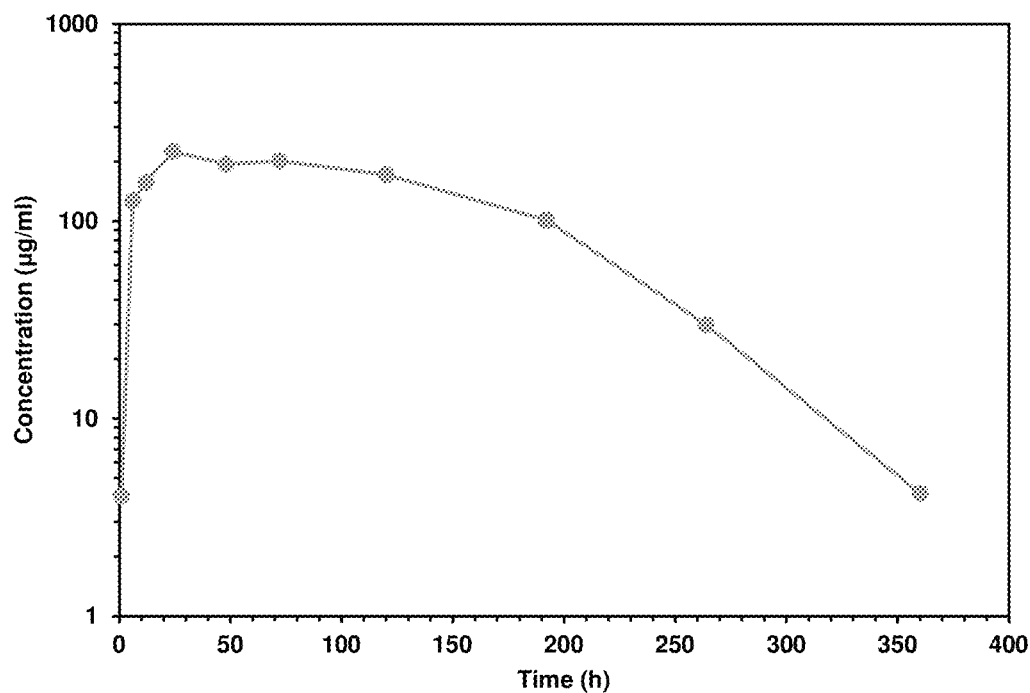

Typically, the conjugates have improved biological activity when compared to the conjugates in the art having the iLZ motif. Generally, the conjugates have an IC50 in vitro between about 0.001 nM and about 0.1 nM, preferably between about 0.001 nM and about 0.05 nM when tested on COLO 205 cells (FIG. 4). The miLZ conjugates have an IC50 in vitro between about 0.01 nM and about 1 nM when tested on activated hepatic stellate cells (HSCs) Colo-205 cells (FIG. 2B).

The conjugates typically have at least about 1.5, at least about 2, at least about 3, at least about 4, at least about 5, at least about 6, at least about 7, at least about 8, at least about 9, at least about 10 or more fold higher biological activity (such as IC50) when compared to the conjugates having iLZ motif. The biological activity is typically expressed as (such as IC50 (half maximum inhibitory concentration) which decreases with an increase in biological activity.

Figure 3:
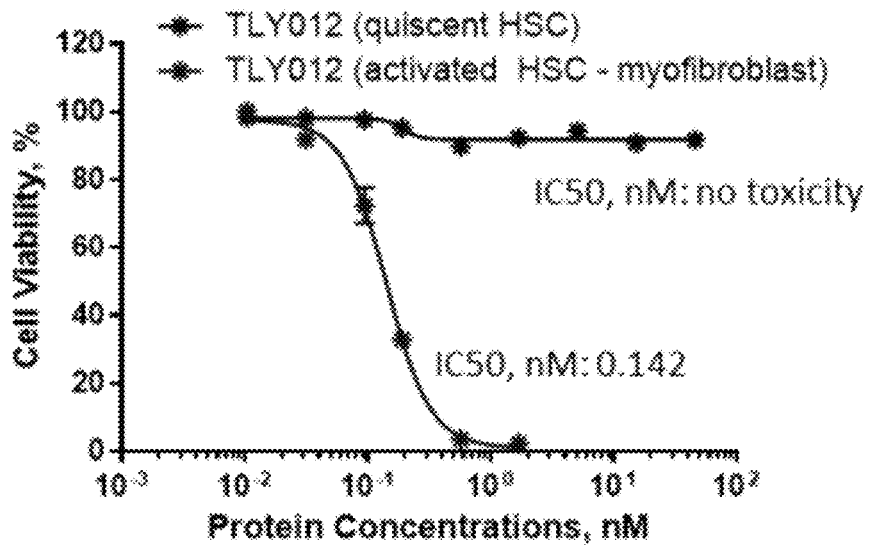
FIG. 3 is a line graph showing the selective cytotoxicity (a change in cell viability (%) over a range of protein concentrations (nM)) for the TLY012 tested on quiescent HSCs and activated HSCs (myofibroblasts). The IC50 (nM) for both concentrations is shown.

As show in the examples below, a TLY012 conjugate containing SEQ ID NO:4 as the first sequence and SEQ ID NO:15 as the second sequence, was cytotoxic to activated HSCs at IC50 of 0.142 nM, and had no effect on quiescent HSCs at high concentrations (100 nM) (FIG. 3).

d. Low Immunogenicity

The low immunogenicity of the PEGylated modified fusion polypeptides is typically similar to that of the low immunogenicity of the modified fusion polypeptides.

Typically, the modified fusion polypeptides carrying miLZ have a lower immunogenicity in a host when compared to the immunogenicity of unmodified polypeptides carrying iLZ in the same host. Generally, the host is a mammal, preferably, human.

The lower immunogenicity may be a lower immunogenicity score for the modified fusion polypeptides carrying miLZ when compared to that of the unmodified polypeptides carrying iLZ. This is described above.

The low immunogenicity of miLZ-TRAIL conjugates in general is comparable to the immunogenicity of therapeutic human proteins such as monoclonal human antibodies. Thus, the total MHCII-binding score in silico for miLZ-TRAIL (SEQ ID 4 and SEQ ID 15) is comparable or better than the immunogenicity of typical human monoclonal antibodies. The lower immunogenicity of miLZ-TRAIL, as compared to iLZ-TRAIL, is defined by a several-fold reduced Total Score (5 vs 27) for MHCII binding in silico.

For example, two protein sequences of interest were analyzed by Abzena using predictive algorithm iTope-AI to identify peptides that bind to human MHC class II and/or share homology to known T cell epitopes. From this analysis, it was determined that SEQ ID NO:32 (contains SEQ ID NO:3 and SEQ ID NO:15) and SEQ ID NO:31 (contains SEQ ID NO:4 and SEQ ID NO:15) had a Total Score of 27 and 5 respectively, with none of the peptide sequences matching a T cell epitope from the TCED™ (Abzena database).

SEQ ID NO:31 contains miLZ sequence with more favorable properties than the iLZ sequence in SEQ ID NO:32, shown below) and has a significantly better Total Score (5 vs 27) which matches the best scores of monoclonal human antibodies.

The low immunogenicity of miLZ-TRAIL conjugates in general is as comparable to the immunogenicity of therapeutic human proteins such as monoclonal human antibodies. Thus the total MHCII-binding score in silico for miLZ-TRAIL (SEQ ID 4 and SEQ ID 15) is comparable or better than the immunogenicity of typical human monoclonal antibodies. The lower immunogenicity of miLZ-TRAIL, as compared to iLZ-TRAIL, is several-fold reduced Total Score (5 vs 27) for MHCII binding in silico. Typically, the immunogenicity of the modified fusion polypeptides is reduced by at least about 1.5, 2, 3, 4, 5, 6, 7, 8, 9, 10, or more fold, preferably between about 2 and 10 fold.

4. Exemplary Fusion Polypeptide-PEG Conjugate

An exemplary conjugate of a PEG moiety and a TRAIL fusion polypeptide is a TLY012 molecule. It is a PEGylated form of recombinant human TRAIL (rhTRAIL), genetically fused to a humanized coiled-coil isoleucine "zipper" (iLZ) at the N-terminus, which favors trimer formation (FIG. 1D). The TRAIL portion of the construct is the extracellular domain starting with V36 as shown in SEQ ID NO:31. The miLZ "zipper" domain is derived from a yeast protein called GCN41. The miLZ "zipper" contains isoleucine substitutions at positions 6, 10, 13, 17, 24, 27 and 31 to enhance trimer formation and two amino acid substitutions, I20V and K29E (substitutions shown relative to SEQ ID NO:2) to reduce the probability of immunogenicity based on in silico analysis. Residues may be added to promote miLZ-TRAIL expression in E. coli, such as the initial G and/or the amino acid linker D, or DG.

Prior to PEGylation, the miLZ-rhTRAIL is a Zn complexed homotrimer, consisting of three identical single-chain polypeptides with an estimated molecular weight of 71.2 kDa (71,175 Da). TLY012 is a mixture of several miLZ-rhTRAIL forms which are PEGylated to different degrees and at different positions with 5 kDa PEG-aldehyde with mono- and di-PEGylated forms being predominant. All PEGylated forms of miLZ-TRAIL present in TLY012 are functionally active in cell-based bioassays (FIG. 3). The amino acid sequence of TLY012 is shown below, an N-terminal Methionine is processed following expression of miLZ-TRAIL in E. coli:

```
                                            (SEQ ID NO: 30)
GRMKQIEDKIEEILSKIYHVENEIARIKELIGEDGVRERGPQ

RVAAHITGTRGRSNTLSSPNSKNEKALGRKINSWESSRSGHS

FLSNLHLRNGELVIHEKGFYYIYSQTYFRFQEEIKENTKNDK

QMVQYIYKYTSYPDPILLMKSARNSCWSKDAEYGLYSIYQGG

IFELKENDRIFVSVTNEHLIDMDHEASFFGAFLVG.
```

5. Complexes

The fusion polypeptides can be complexed with a negatively charged moiety. In some embodiments the negatively charged moiety can facilitate loading the fusion polypeptides into a nanoparticle for extended, sustained, or time released delivery. In some embodiments, the negatively charged moiety itself mediates extended, sustained, or time released delivery of the fusion polypeptides. Preferably, the negatively charged moiety does not substantially reduce the ability of the fusion polypeptides to induce or enhance apoptosis.

The formation of a complex between positively charged TRAIL and the negatively charged chondroitin sulfate (CS) (CS/TRAIL) was shown to facilitate loading of TRAIL in poly(lactide-co-glycolide) (PLGA) microspheres (MSs), without compromising the activity of the TRAIL (Kim, et al., *Journal of Pharmacy and Pharmacology*, 65(1):11-21 (2013)). A nanocomplex of approximately 200 nm was formed in a weight ratio of 2 TRAIL to CS (TC2) at pH 5.0. The complex had >95% higher loading efficiency in PLGA MSs prepared by the multi-emulsion method than that of native TRAIL. Therefore, in some embodiments, the fusion polypeptides or conjugates are complexed with chondroitin sulfate and optionally loaded into micro- or nanoparticles, for example, PLGA-based particles.

In other embodiments, fusion polypeptides or conjugates thereof are complexed with hyaluronic acid (HA). Nanocomplexes of PEG-TRAIL and HA prepared by mixing positively charged PEG-TRAIL and negatively charged HA, were shown to have sustained delivery in vivo, with negligible loss of bioactivity compared with the PEG-TRAIL (Kim, et al., *Biomaterials*, 31(34):9057-64 (2010)). Delivery was further enhanced by administering the nanoparticles in a 1% HA containing solution.

C. Polynucleotides Encoding Fusion Polypeptides

Disclosed are polynucleotides that encode the recombinant fusion polypeptides. Such polynucleotides can be provided in an expression vector. The expression vector typically includes a promoter operably linked to the polynucleotide. The promoter can be any promoter including a constitutively active, inducible, conditional, or tissue specific promoter. The polynucleotide can be suitable for expression in yeast (such as *Pichia pastoris*) or *E. coli* expression systems.

Methods of expressing these polynucleotides are known in the art. Such methods involve transfecting an *E. coli* cell with the expression vector, provided that the expression vector includes an inducible promoter. The transfected *E. coli* cells are used to inoculate a media. The media typically includes zinc ions, such as in a form of zinc chloride.

Nucleotide sequences encoding the fusion polypeptides are listed below, with codons of interest shown in boxes:

(SEQ ID NO: 33)
CATATGGGCCATCATCACCACCATCATCATCACCCAGGCATGTGC

GGCGGCAAACAGATCGAAGATAAGATTGAAGAAATTCTGTCCAA

GATTTACCAC[ATC]GAGAATGAAATCGCACGTATCAAA[AAG]CTGA

TCGGTGAGGACGGTGTCCGCGAGCGTGGTCCGCAGCGTGTTGCGG

CGCATATCACGGGTACTCGTGGTCGCAGCAACACCCTGAGCAGCC

CGAATAGCAAAAATGAAAAGGCTCTGGGTCGTAAGATTAACTCCT

GGGAGAGCAGCCGCTCCGGTCACAGCTTCCTGAGCAATCTGCACT

TGCGTAACGGTGAGCTGGTTATTCACGAGAAAGGCTTCTATTACA

TTTACAGCCAAACCTATTTTCGTTTTCAAGAGGAAATCAAAGAGA

ATACCAAAAACGATAAGCAAATGGTTCAGTACATCTACAAGTACA

CCTCGTATCCGGACCCGATCCTGTTGATGAAAAGCGCGCGTAATA

GCTGTTGGTCTAAAGATGCAGAGTATGGTCTGTATAGCATTTACC

AGGGTGGCATTTTCGAGCTGAAAGAAAACGACCGCATCTTTGTCT

CTGTGACGAACGAACACCTGATTGACATGGATCACGAAGCGAGCT

TCTTTGGCGCCTTCCTGGTGGGTTAATAAGAGCTC;

(SEQ ID NO: 34)
CATATGGGGAGGATGAAGCAAATAGAGGATAAGATCGAGGAGAT

CCTCTCGAAGATATACCAC[GTC]GAGAACGAGATAGCCCGTATCAA

A[GAG]CTTATTGGGGAAGATGGAGTCAGGGAGAGGGGTCCCCAGA

GAGTGGCAGCACACATTACCGGTACAAGAGGCCGTAGTAATACC

CTCAGTAGCCCTAATAGTAAAAACGAGAAAGCCCTCGGACGCAA

GATTAACTCGTGGGAATCTTCTCGCTCCGGGCACTCTTTTCTTTCG

AACTTGCATCTGAGAAATGGGGAGCTGGTGATTCACGAGAAGGG

ATTCTACTACATCTATTCCCAGACGTACTTCCGGTTCCAGGAGGA

GATAAAAGAGAACACGAAGAACGACAAGCAGATGGTCCAGTACA

TCTACAAGTACACGTCTTACCCGGACCCTATCCTCTTAATGAAGTC

GGCGCGTAGCTCCTGTTGGTCTAAAGACGCAGAGTATGGATTGTA

CAGTATTTACCAGGGAGGGATATTCGAGCTGAAGGAAAACGATC

GGATCTTCGGATCGGTTACCGATGAGCACCTGATAGACATGGATC

ATGAGGCTAGCTTCTTTGGAGCATTTTTGGTGGGATAATAAGAGC

TC;

(SEQ ID NO: 35)
CATATGGGCCATCATCACCACCATCATCATCACCCAGGCATGTGC

GGCGGCAAACAGATCGAAGATAAGATTGAAGAAATTCTGTCCAA

GATTTACCAC[ATC]GAGAATGAAATCGCACGTATCAAA[AAG]CTGA

TCGGTGAGGACGGTGTCCGCGAGCGTGGTCCGCAGCGTGTTGCGG

CGCATATCACGGGTACTCGTGGTCGCAGCAACACCCTGAGCAGCC

CGAATAGCAAAAATGAAAAGGCTCTGGGTCGTAAGATTAACTCCT

GGGAGAGCAGCCGCTCCGGTCACAGCTTCCTGAGCAATCTGCACT

TGCGTAACGGTGAGCTGGTTATTCACGAGAAAGGCTTCTATTACA

TTTACAGCCAAACCTATTTTCGTTTTCAAGAGGAAATCAAAGAGA

ATACCAAAAACGATAAGCAAATGGTTCAGTACATCTACAAGTACA

CCTCGTATCCGGACCCGATCCTGTTGATGAAAAGCGCGCGTAATA

GCTGTTGGTCTAAAGATGCAGAGTATGGTCTGTATAGCATTTACC

AGGGTGGCATTTTCGAGCTGAAAGAAAACGACCGCATCTTTGTCT

CTGTGACGAACGAACACCTGATTGACATGGATCACGAAGCGAGCT

TCTTTGGCGCCTTCCTGGTGGGTTAATAAGAGCTC;

(SEQ ID NO: 36)
CATATGGGCCATCATCACCACCATCATCATCACCCAGGCATGTGC

GGCGGCAAACAGATCGAAGATAAGATTGAAGAAATTCTGTCCAA

GATTTACCAC[GTG]GAGAATGAAATCGCACGTATCAAA[GAA]CTGA

TCGGTGAGGACGGTGTCCGCGAGCGTGGTCCGCAGCGTGTTGCGG

CGCATATCACGGGTACTCGTGGTCGCAGCAACACCCTGAGCAGCC

CGAATAGCAAAAATGAAAAGGCTCTGGGTCGTAAGATTAACTCCT

GGGAGAGCAGCCGCTCCGGTCACAGCTTCCTGAGCAATCTGCACT

TGCGTAACGGTGAGCTGGTTATTCACGAGAAAGGCTTCTATTACA

TTTACAGCCAAACCTATTTTCGTTTTCAAGAGGAAATCAAAGAGA

ATACCAAAAACGATAAGCAAATGGTTCAGTACATCTACAAGTACA

CCTCGTATCCGGACCCGATCCTGTTGATGAAAAGCGCGCGTAATA

GCTGTTGGTCTAAAGATGCAGAGTATGGTCTGTATAGCATTTACC

AGGGTGGCATTTTCGAGCTGAAAGAAAACGACCGCATCTTTGTCT

CTGTGACGAACGAACACCTGATTGACATGGATCACGAAGCGAGCT

TCTTTGGCGCCTTCCTGGTGGGTTAATAAGAGCTC;

(SEQ ID NO: 37)
CATATGGGCCATCATCACCACCATCATCATCACCCAGGCATGTGC

GGCGGCAAACAGATCGAAGATAAGATTGAAGAAATTCTGTCCAA

GATTTACCAC`GTG`GAGAATGAAATCGCACGTATCAAA`AAG`CTGA

TCGGTGAGGACGGTGTCCGCGAGCGTGGTCCGCAGCGTGTTGCGG

CGCATATCACGGGTACTCGTGGTCGCAGCAACACCCTGAGCAGCC

CGAATAGCAAAAATGAAAAGGCTCTGGGTCGTAAGATTAACTCCT

GGGAGAGCAGCCGCTCCGGTCACAGCTTCCTGAGCAATCTGCACT

TGCGTAACGGTGAGCTGGTTATTCACGAGAAAGGCTTCTATTACA

TTTACAGCCAAACCTATTTTCGTTTTCAAGAGGAAATCAAAGAGA

ATACCAAAAACGATAAGCAAATGGTTCAGTACATCTACAAGTACA

CCTCGTATCCGGACCCGATCCTGTTGATGAAAAGCGCGCGTAATA

GCTGTTGGTCTAAAGATGCAGAGTATGGTCTGTATAGCATTTACC

AGGGTGGCATTTTCGAGCTGAAAGAAAACGACCGCATCTTTGTCT

CTGTGACGAACGAACACCTGATTGACATGGATCACGAAGCGAGCT

TCTTTGGCGCCTTCCTGGTGGGTTAATAAGAGCTC;

(SEQ ID NO: 38)
CATATGGGCCATCATCACCACCATCATCATCACCCAGGCATGTGC

GGCGGCAAACAGATCGAAGATAAGATTGAAGAAATTCTGTCCAA

GATTTACCAC`ATC`GAGAATGAAATCGCACGTATCAAA`GAA`CTGA

TCGGTGAGGACGGTGTCCGCGAGCGTGGTCCGCAGCGTGTTGCGG

CGCATATCACGGGTACTCGTGGTCGCAGCAACACCCTGAGCAGCC

CGAATAGCAAAAATGAAAAGGCTCTGGGTCGTAAGATTAACTCCT

GGGAGAGCAGCCGCTCCGGTCACAGCTTCCTGAGCAATCTGCACT

TGCGTAACGGTGAGCTGGTTATTCACGAGAAAGGCTTCTATTACA

TTTACAGCCAAACCTATTTTCGTTTTCAAGAGGAAATCAAAGAGA

ATACCAAAAACGATAAGCAAATGGTTCAGTACATCTACAAGTACA

CCTCGTATCCGGACCCGATCCTGTTGATGAAAAGCGCGCGTAATA

GCTGTTGGTCTAAAGATGCAGAGTATGGTCTGTATAGCATTTACC

AGGGTGGCATTTTCGAGCTGAAAGAAAACGACCGCATCTTTGTCT

CTGTGACGAACGAACACCTGATTGACATGGATCACGAAGCGAGCT

TCTTTGGCGCCTTCCTGGTGGGTTAATAAGAGCTC;

(SEQ ID NO: 39)
CATATGGGCCATCATCACCACCATCATCATCACCCAGGCATGTGC

GGCGGCAAACAGATCGAAGATAAGATTGAAGAAATTCTGTCCAA

GATTTACCAC`ATC`GAGAATGAAATCGCACGTATCAAA`CAA`CTGAT

CGGTGAGGACGGTGTCCGCGAGCGTGGTCCGCAGCGTGTTGCGGC

GCATATCACGGGTACTCGTGGTCGCAGCAACACCCTGAGCAGCCC

GAATAGCAAAAATGAAAAGGCTCTGGGTCGTAAGATTAACTCCTG

GGAGAGCAGCCGCTCCGGTCACAGCTTCCTGAGCAATCTGCACTT

GCGTAACGGTGAGCTGGTTATTCACGAGAAAGGCTTCTATTACAT

TTACAGCCAAACCTATTTTCGTTTTCAAGAGGAAATCAAAGAGAA

TACCAAAAACGATAAGCAAATGGTTCAGTACATCTACAAGTACAC

CTCGTATCCGGACCCGATCCTGTTGATGAAAAGCGCGCGTAATAG

CTGTTGGTCTAAAGATGCAGAGTATGGTCTGTATAGCATTTACCA

GGGTGGCATTTTCGAGCTGAAAGAAAACGACCGCATCTTTGTCTC

TGTGACGAACGAACACCTGATTGACATGGATCACGAAGCGAGCTT

CTTTGGCGCCTTCCTGGTGGGTTAATAAGAGCTC;

(SEQ ID NO: 40)
CATATGGGCCATCATCACCACCATCATCATCACCCAGGCATGTGC

GGCGGCAAACAGATCGAAGATAAGATTGAAGAAATTCTGTCCAA

GATTTACCAC`GTG`GAGAATGAAATCGCACGTATCAAA`CAA`CTGA

TCGGTGAGGACGGTGTCCGCGAGCGTGGTCCGCAGCGTGTTGCGG

CGCATATCACGGGTACTCGTGGTCGCAGCAACACCCTGAGCAGCC

CGAATAGCAAAAATGAAAAGGCTCTGGGTCGTAAGATTAACTCCT

GGGAGAGCAGCCGCTCCGGTCACAGCTTCCTGAGCAATCTGCACT

TGCGTAACGGTGAGCTGGTTATTCACGAGAAAGGCTTCTATTACA

TTTACAGCCAAACCTATTTTCGTTTTCAAGAGGAAATCAAAGAGA

ATACCAAAAACGATAAGCAAATGGTTCAGTACATCTACAAGTACA

CCTCGTATCCGGACCCGATCCTGTTGATGAAAAGCGCGCGTAATA

GCTGTTGGTCTAAAGATGCAGAGTATGGTCTGTATAGCATTTACC

AGGGTGGCATTTTCGAGCTGAAAGAAAACGACCGCATCTTTGTCT

CTGTGACGAACGAACACCTGATTGACATGGATCACGAAGCGAGCT

TCTTTGGCGCCTTCCTGGTGGGTTAATAAGAGCTC.

D. Pharmaceutical Compositions

Pharmaceutical compositions contain an effective amount of the disclosed fusion polypeptides (or polynucleotides), or conjugates, and, optionally, a pharmaceutically acceptable carrier. These pharmaceutical compositions may be used in the treatment of proliferative, autoimmune, or fibrotic diseases.

The pharmaceutical compositions may include the fusion polypeptides (or polynucleotides), or the conjugates as the first therapeutic, prophylactic or diagnostic agent and include a second therapeutic, prophylactic or diagnostic agent.

Typical excipients include sterile water, sterile saline or sterile buffered water or saline, typically formulated for administration by injection.

III. Methods of Making

A. Methods of Making Fusion Polypeptides

The fusion polypeptides can be manufactured using conventional techniques that are known in the art. Isolated polypeptides can be obtained by, for example, chemical synthesis or by recombinant production in a host cell. To recombinantly produce a polypeptide, a nucleic acid containing a nucleotide sequence encoding the fusion protein can be used to transform, transduce, or transfect a bacterial or eukaryotic host cell (e.g., an insect, yeast, or mammalian cell). In general, nucleic acid constructs include a regulatory sequence operably linked to a nucleotide sequence encoding the polypeptides. Regulatory sequences (also referred to herein as expression control sequences) typically do not encode a gene product, but instead affect the expression of the nucleic acid sequences to which they are operably linked.

Useful prokaryotic and eukaryotic systems for expressing and producing polypeptides are well known in the art and include, for example, *Escherichia coli* strains such as BL-21, and cultured mammalian cells such as CHO cells.

The expression of glycoproteins in mammalian cells typically results in mammalian-type glycosylation. For human proteins this is ideal, however some cell lines add the non-human Gal α1-3 Gal epitope and the N-glycolyl-neuraminic acid (NGNA). Insect expression systems add shorter N-glycans, with little sialylation. Plant cells typically have glycans that contain extra fucose and xylose residues. Yeast expression systems have a very different glycosylation pattern from mammalian cells, with only mannose-containing glycans. Generally, the iLZ-TRAIL and miLZ are not dependent on glycosylation so bacterial and mammalian cell lines are useful for expressing the constructs.

In eukaryotic host cells, a number of viral-based expression systems can be utilized to express polypeptides. Viral based expression systems are well known in the art and include, but are not limited to, baculoviral, SV40, retroviral, or vaccinia based viral vectors.

Mammalian cell lines that stably express polypeptides can be produced using expression vectors with appropriate control elements and a selectable marker. For example, the eukaryotic expression vectors pCR3.1 (Invitrogen Life Technologies) and p91023(B) (see Wong et al. (1985) *Science* 228:810-815) are suitable for expression of variant polypeptides in, for example, Chinese hamster ovary (CHO) cells, COS-1 cells, human embryonic kidney 293 cells, NIH3T3 cells, BHK21 cells, MDCK cells, and human vascular endothelial cells (HUVEC). Additional suitable expression systems include the GS Gene Expression System™ available through Lonza Group Ltd.

Following introduction of an expression vector by electroporation, lipofection, calcium phosphate, or calcium chloride co-precipitation, DEAE dextran, or other suitable transfection method, stable cell lines can be selected (e.g., by metabolic selection, or antibiotic resistance to G418, kanamycin, or hygromycin). The transfected cells can be cultured such that the polypeptide of interest is expressed, and the polypeptide can be recovered from, for example, the cell culture supernatant or from lysed cells.

Polypeptides can be isolated using, for example, chromatographic methods such as affinity chromatography, ion exchange chromatography, hydrophobic interaction chromatography, DEAE ion exchange, gel filtration, and hydroxyapatite chromatography. In some embodiments, polypeptides can be engineered to contain an additional domain containing amino acid sequence that allows the polypeptides to be captured onto an affinity matrix. For example, an Fc-fusion polypeptide in a cell culture supernatant or a cytoplasmic extract can be isolated using a protein A column. A tag such as c-myc, hemagglutinin, polyhistidine, or FLAG™ (Kodak) can be used to aid polypeptide purification. Such tags can be inserted anywhere within the polypeptide, including at either the carboxyl or amino terminus. Other fusions that can be useful include enzymes that aid in the detection of the polypeptide, such as alkaline phosphatase Immunoaffinity chromatography also can be used to purify polypeptides. Polypeptides can additionally be engineered to contain a secretory signal (if there is not a secretory signal already present) that causes the polypeptide to be secreted by the cells in which it is produced. The secreted polypeptides can then conveniently be isolated from the cell media.

1. Exemplary Method

The fusion polypeptide containing SEQ ID NO:4 as the first sequence and SEQ ID NO:15 as the second sequence may be according to the following method.

A polynucleotide encoding SEQ ID NO:4 and SEQ ID NO:15 in an expression cassette is produced in *Escherichia coli* using pET23 expression vector. After amplification in *E. coli*, the expression of the fusion polypeptide is induced from an inducible promoter using isopropyl-L-thio-B-D-galactopyranoside (0.02-1 mmol/L, 7 h at 27° C.). The cells are then harvested, lysed and the soluble fusion polypeptide is purified by affinity (Zn-NTA) and HIC (C4) chromatography.

B. Methods of Making Conjugates

The PEG-fusion polypeptide conjugates can be obtained by reacting an N-terminal amine of the first or second sequence of the fusion polypeptide with an aldehyde group of the PEG in the presence of a reducing agent. PEG and the fusion polypeptide can be reacted at a molar ratio (PEG/miLZ-TRAIL) of 2 to 50, or preferably 5 to 7.5.

A method for making the PEG-fusion polypeptide conjugates typically includes reacting the fusion polypeptide with an aldehyde group of a PEG or a derivative thereof. Exemplary derivatives of PEG include methoxypolyethylene glycol succinimidyl propionate, methoxypolyethylene glycol N-hydroxysuccinimide, methoxypolyethylene glycol aldehyde, methoxypolyethylene glycol maleimide and multiple-branched polyethylene glycol. The reaction typically occurs in the presence of a reducing agent. The PEG or the derivative thereof typically has a molecular weight of between 1,000 and 100,000 as determined by SDS-PAGE and MALDI-TOF.

In an exemplary method, PEG and the fusion polypeptide are reacted at a molar ratio (PEG/fusion polypeptide) of 2 to 10, and preferably 5 to 7.5. The reducing agent is typically NaCNBH$_3$.

IV. Methods of Using

The formulations are typically used in methods for preventing or treating a disease. The methods generally include administering a solid or liquid composition of the fusion polypeptide, polynucleotide, or the conjugate, to a subject in need thereof.

The fusion polypeptides, polynucleotides, conjugates or pharmaceutical compositions containing an effective amount of the fusion polypeptides, polynucleotides, or conjugates, to treat or alleviate one or more symptoms of the disease or disorder, optionally with a pharmaceutically acceptable carrier are typically administered parenterally, such as by injection, topically (as during surgery) or to a mucosal surface (rectally, vaginally, orally or pulmonarily). These may be administered in solution, in implants or gels, or as dry powders in dry form or redissolved or resuspended.

The methods typically include using the fusion polypeptides, polynucleotides, or the conjugate, alone or in the form of a composition to treat proliferative diseases, such as cancer, autoimmune diseases, such as rheumatoid arthritis, or fibrotic diseases.

Following administration, the state, symptoms, or manifestations, of the disease are typically monitored by the subject and the treating physician. In preferred embodiments, administration of the formulation reduces, partially or completely, the severity of one or more symptoms, or manifestations, of the disease is when compared to the severity of the symptoms prior to administration. This reduction in symptom severity alleviates, ameliorates, relieves, delays onset of, inhibits progression of, reduces severity of, and/or reduces incidence of the same or other symptom, or of a particular disease, disorder, and/or condition, in the subject.

The fusion polypeptides, polynucleotides, or conjugates, or their compositions, may be formulated into various formulations for parenteral administration upon clinical application. The administration of the formulation to a subject delivers a therapeutically effective amount of the fusion polypeptides, polynucleotides, or conjugates, or their compositions, to cells and tissue.

The desired dosage may be delivered once a day or multiple times a day. For example, the desired dosage may be delivered three times a day, two times a day, once a day, twice a week, once a week, or once every week. In certain embodiments, the desired dosage may be delivered using multiple administrations (e.g., two, three, four, five, six, seven, eight, nine, ten, eleven, twelve, thirteen, fourteen, or more administrations).

The dosage for a specific patient will be adjusted according to the patient's weight, age, gender, state of health and diet, administration duration, administration routes, excretion rates and severity of illness. Typically, it is possible to administer an effective dosage once every one to two weeks. Alternatively, the dosage may be taken in a single dose or in several divided doses within a daily effective dosage.

The fusion polypeptides, polynucleotides, or conjugates, or their compositions, are typically formulated in dosage unit form for ease of administration and uniformity of dosage. It will be understood, however, that the total daily usage of the compositions will be decided by the attending physician within the scope of sound medical judgment. The specific therapeutically effective dose level for any particular subject will depend upon a variety of factors including the disorder being treated and the severity of the disorder; the activity of the specific active agent employed; the specific composition employed; the age, body weight, general health, sex and diet of the subject; the time of administration, route of administration, and rate of excretion of the specific active agent employed; the duration of the treatment; drugs used in combination or coincidental with the specific active agent employed; and like factors known in the medical arts.

In certain embodiments, dosage units contain the fusion polypeptides, polynucleotides, or conjugates, or their compositions, in amounts from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

A. Diseases to be Treated

1. Proliferative Disorders Such as Cancer

The fusion polypeptides, polynucleotides, conjugates, or their compositions are useful for treating subjects with benign or malignant tumors, or other excessive proliferation disorders, by delaying or inhibiting the growth of a tumor in a subject, reducing the growth or size of the tumor, inhibiting or reducing metastasis of the tumor, and/or inhibiting or reducing symptoms associated with tumor development or growth.

Malignant tumors which may be treated can be classified according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The proliferative disease may be cancer, with primary tumors originating in the liver, pancreas, colon, brain, breast, prostate, lung, head and neck, stomach, lymph nodes, and skin. The tumors may be primary tumors or metastatic tumors. The tumors may be solid tumors.

a. Targeting Cancer-Associated Fibroblasts

Immunotherapy, or more specifically, the use of monoclonal antibodies that block inhibitory immune checkpoint molecules to enhance the immune response to tumors, has shown clinical promise in advanced solid tumors. Therapies in this category include PD-1, PD-L1, CTLA-4, IDO pathway blockers. Significant advances have been made in oncology treatment, including the development of checkpoint inhibitor-based cancer immunotherapy. However, immunotherapy only benefits patients with selected cancer types such as melanoma and lung cancer, and the development of effective immunotherapy for solid cancers including Hepatocellular carcinoma (HCC), Pancreatic ductal adenocarcinoma (PDAC), or Colon cancer (CRC) has been relatively slow. It is now widely accepted that one of the major components of primary resistance to immunotherapy is the immunosuppressive tumor microenvironment (TME). The establishment of the tumor microenvironment (TME) not only allows the tumor to develop but permits it to recruit components of the host immune system. The TME components primarily act as cellular barriers to prevent any infiltration by antitumor immune cells in addition to promoting tumor growth (Weiner, *Clinical Advances in Hematology & Oncology*.; 13(5):299-306 (2015), Chiriva-Internati and Bot. *International Reviews of Immunology*; 34(2):101-103 (2015)). The development of a stromal layer surrounding the cancerous mass creates a physical barrier that is characterized by several features known to promote cancer growth, including the development of hypoxic conditions and abnormal tumor neovascularization (Klener et al., *Current Pharmaceutical Biotechnology*; 16(9):771-781 (2015)). The TME is a heterogeneous population of cells consisting of tumor cells and fibrotic stromal cells. The most important sources of stromal cells are alpha-smooth muscle actin (α-SMA)+myofibroblasts (MFBs, activated fibroblasts) and cancer-associated fibroblasts (CAFs), which are known to contribute to the production of excessive extracellular matrix (ECM) depositions, tumor initiation, and progression, and strong immunosuppressive properties in solid cancers.

The fusion polypeptides and the fusion polypeptide conjugates, when used in cancer therapy, target cancer associated fibroblasts and induce apoptosis in cancer associated fibroblasts.

It is shown here that the fusion polypeptide conjugate TLY012 has anti-fibrogenic function and targets the fibrogenic tumors with cancer associated fibroblasts, which, without therapy, are resistant to immunotherapy because of the fibrotic cell barrier.

2. Autoimmune Diseases

The fusion polypeptides, polynucleotides, conjugates, or their compositions can be administered to prevent or treat one or more symptoms of an autoimmune disease. Representative autoimmune diseases include lupus, rheumatoid arthritis, and type I diabetes.

Systemic lupus erythematosus (SLE) is an autoimmune disease with a broad spectrum of clinical and immunological abnormalities. The presence of autoantibodies, especially those directed to double stranded DNA, is characteristic of the disease. SLE may affect different organ systems, including the skin, joints, central and peripheral nervous system, kidneys, and liver. The etiology of the disease remains unknown. There is, however, increasing evidence that the presence and accumulation of apoptotic cells play a role in autoimmunity (Hooge et al., *Ann Rheum Dis,* 64:854-858 (2005)).

Increased serum soluble TRAIL concentrations in SLE patients were observed and were found to be disease specific. Levels in patients with inactive disease were more often increased than in patients with active disease.

Rheumatoid arthritis (RA) is a form of arthritis that causes pain, swelling, stiffness and loss of function in joints. It can affect any joint but is common in the wrist and fingers. More women than men get rheumatoid arthritis. The disease may be present for only a short time, or symptoms might come and go. The severe form can last a lifetime.

Rheumatoid arthritis is different from osteoarthritis (OA), the common arthritis that often comes with older age. RA can affect body parts besides joints, such as eyes, mouth and lungs. RA is an autoimmune disease, which means the arthritis results from your immune system attacking body's own tissues.

Patients with rheumatoid arthritis (RA) show elevated TRAIL expression when compared with that in patients with osteoarthritis (OA). The inflammatory environment in the arthritic joints of patients with RA appears to promote TRAIL expression in fibroblast-like synoviocytes (FLS) (Audo et al., *Arthritis and Rheumatism,* 63(4):904-913 (2011)).

Diabetes, or diabetes mellitus, is due to either the pancreas not producing enough insulin or the cells of the body not responding properly to the insulin produced. There are three main types of diabetes mellitus:

Type 1 Diabetes results from the pancreas' failure to produce enough insulin. This form was previously referred to as "insulin-dependent diabetes mellitus" (IDDM) or "juvenile diabetes", Type 2 Diabetes begins with insulin resistance, a condition in which cells fail to respond to insulin properly. As the disease progresses a lack of insulin may also develop. This form was previously referred to as "non-insulin-dependent diabetes mellitus" (NIDDM) or "adult-onset diabetes"; and Gestational diabetes, the third main form, occurs when pregnant women, without a previous history of diabetes, develop a high blood sugar level.

Type 1 diabetes must be managed with insulin therapy to survive. Type 1 diabetes is an autoimmune inflammatory disease of the pancreatic islets. In human type 1 diabetes and its rodent models, pancreatic β-cells that produce insulin are selectively destroyed by infiltrating inflammatory cells.

The role of TRAIL in vivo may include inhibiting autoimmune inflammation in the islets of Langerhans. TRAIL may inhibit insulitis and suppresses autoimmune diabetes.

Both T-cells and macrophages are involved in mediating β-cell injury in this disease. TRAIL may regulate diabetes through acting on one or both of these cells. TRAIL also may block DNA synthesis and cell cycle progression of T-cells activated by anti-CD3 antibody. TRAIL may mediate negative selection of thymocytes. Therefore, TRAIL may inhibit diabetic inflammation and autoreactive T-cell activation (Lamhamedi-Cherradi et al., *Diabetes* 52:2274-2278 (2003)).

The Examples below illustrate that activated cells, such as hepatic stellate cells, can be specifically targeted and killed by a PEGylated fusion polypeptide conjugate TLY012 without affecting the quiescent hepatic stellate cells. This treatment led to TRAIL-induced apoptosis to prevent or reverse fibrosis. Importantly, by eliminating such activated stellate cells, highly upregulated fibrosis-associated molecules may be simultaneously down-regulated. This demonstrates that the compounds can be used for treating pathological conditions in which activated fibroblasts, myofibroblastic cells, myofibroblasts, and activated endothelial and epithelial cells produce or induce an excess amount of extracellular matrix resulting in unwanted fibrosis or scarring are disclosed. The scarring or fibrosis can be in the liver, pancreas, lungs, heart, kidneys, intestine, skin or arteries.

B. Combination Therapies

One or more of the recombinant fusion polypeptides, polynucleotides, or the fusion polypeptide conjugates can be administered to subjects in need thereof alone, or in combination, with one or more additional active agents. In these embodiments, the recombinant fusion polypeptides, polynucleotides, or the fusion polypeptide conjugates are the first active agent additional active agents are the second active agent. In some embodiments, the second active agent is an agent that is known in the art for treatment of a proliferative disease, autoimmune disease, or fibrotic disease. In some embodiments, the second active agent is one that modulates host cells, for example, an agent that modulates cancer cell proliferation, reduces stellate cell activation or activity, increases cancer cell or stellate cell apoptosis, reduces deposition of extracellular matrix or components thereof, particularly collagen, increases degradation of extracellular matrix or components thereof, particularly collagen, or any combination thereof. In some embodiments, the first active agent increases the efficacy, enhances the effect, or otherwise improves the performance or sensitivity of cells to the second active agent.

1. Second Active Agents

The second active agents that can be used with the recombinant fusion polypeptides, the recombinant polynucleotides, or the recombinant fusion polypeptide conjugates and can be chemotherapeutic agents or anti-inflammatory agents.

a. Chemotherapeutic Agents

The recombinant fusion polypeptides, recombinant polynucleotides, or the recombinant fusion polypeptide conjugates have been investigated for use in the treatment of cancer, both alone and in combination with conventional cancer treatments such as chemotherapeutic agents. Some reports indicate that chemotherapeutic drugs can sensitize cells to TRAIL-induced apoptosis, and some results indicate that the combination of the two agents is more effective than the sum of effects of the agents when used alone (Cuello, et al., *Gynecol Oncol.*, 81(3):380-90 (2001); Wu, et al., *Vitam Horm.*, 67:365-83 (2004)). Therefore, in some embodiments, the subjects and diseases disclosed are treated with a combination of one or more of the recombinant fusion polypeptides or the one or more recombinant fusion polypeptide conjugates and a chemotherapeutic agent. In some embodiments, the subjects have cancer. In some embodiments, the subjects have cancer with solid tumors.

Exemplary chemotherapeutic drugs include, but are not limited to, doxorubicin, etoposide, camptothecin, irinotecan, cisplatin, oxaliplatin, docetaxel, cyclophosphamide, 5-fluorouracil, carboplatin, mechlorethamine, sorafenib, schlorambucil, vincristine, vinblastine, vinorelbine, vindesine, taxol and derivatives thereof, topotecan, amsacrine, etoposide phosphate, teniposide, epipodophyllotoxins, trastuzumab (HERCEPTIN®), cetuximab, and rituximab (RITUXAN® or MABTHERA®), bevacizumab (AVASTIN®), and combinations thereof.

i. Immune Checkpoint Inhibitors

The second active agent may include one or more immune checkpoint inhibitors (ICI). Generally, the ICI include small molecules, antibodies, or an antibody fragment against programmed cell death protein 1 (PD-1), against PD-1 Ligand 1 (PD-L1), and against cytotoxic T-lymphocyte-associated antigen 4 (CTLA-4).

Typically, the second active agent include ICI at between about between about 0.1 mg/kg and about 100 mg/kg of the body weight of the patient in an injection dose. Suitable amounts of the ICI in the vaccine include between about 0.1 mg/kg and about 500 mg/kg, between about 0.1 mg/kg and about 250 mg/kg, between about 0.1 mg/kg and about 100 mg/kg, between about 0.1 mg/kg and about 80 mg/kg, and between about 0.1 mg/kg and about 60 mg/kg, such as between about 0.5 mg/kg and about 20 mg/kg, or between about 1 mg/kg and about 10 mg/kg. Specific concentrations of the ICI include 0.1 mg/kg, 0.2 mg/kg, 0.3 mg/kg 0.4 µM, 0.5 mg/kg, 0.6 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, and 50 mg/kg.

PD-1 Antagonists

The second active agent may be a PD-1 and/or PD-L1/PD-L2 antagonist.

Activation of T cells normally depends on an antigen-specific signal following contact of the T cell receptor (TCR) with an antigenic peptide presented via the major histocompatibility complex (MHC) while the extent of this reaction is controlled by positive and negative antigen-independent signals emanating from a variety of co-stimulatory molecules. The latter are commonly members of the CD28/B7 family Conversely, Programmed Death-1 (PD-1) is a member of the CD28 family of receptors that delivers a negative immune response when induced on T cells. Contact between PD-1 and one of its ligands (B7-H1 or B7-DC) induces an inhibitory response that decreases T cell multiplication and/or the strength and/or duration of a T cell response. Suitable PD-1 antagonists are described in U.S. Pat. Nos. 8,114,845, 8,609,089, and 8,709,416, and include compounds or agents that either bind to and block a ligand of PD-1 to interfere with or inhibit the binding of the ligand to the PD-1 receptor, or bind directly to and block the PD-1 receptor without inducing inhibitory signal transduction through the PD-1 receptor.

In some embodiments, the PD-1 receptor antagonist binds directly to the PD-1 receptor without triggering inhibitory signal transduction and also binds to a ligand of the PD-1 receptor to reduce or inhibit the ligand from triggering signal transduction through the PD-1 receptor. By reducing the number and/or amount of ligands that bind to PD-1 receptor and trigger the transduction of an inhibitory signal, fewer cells are attenuated by the negative signal delivered by PD-1 signal transduction and a more robust immune response can be achieved.

It is believed that PD-1 signaling is driven by binding to a PD-1 ligand (such as B7-H1 or B7-DC) in close proximity to a peptide antigen presented by major histocompatibility complex (MHC) (see, for example, Freeman, *Proc. Natl. Acad. Sci. U.S.A*, 105: 10275-10276 (2008)).

Therefore, proteins, antibodies or small molecules that prevent co-ligation of PD-1 and TCR on the T cell membrane are also useful PD-1 antagonists.

Other PD-1 antagonists include antibodies that bind to PD-1 or ligands of PD-1, and other antibodies.

Suitable anti-PD-1 antibodies include, but are not limited to, those described in the following publications: PCT/IL03/00425 (Hardy et al, WO/2003/099196), PCT/JP2006/309606 (Korman et al, WO/2006/121168), PCT/US2008/008925 (Li et al, WO/2009/014708), PCT/JP03/08420 (Honjo et al, WO/2004/004771), PCT/JP04/00549 (Honjo et al, WO/2004/072286), PCT/IB2003/006304 (Collins et al, WO/2004/056875), PCT/US2007/088851 (Ahmed et al, WO/2008/083174), PCT/US2006/026046 (Korman et al, WO/2007/005874), PCT/US2008/084923 (Terrett et al, WO/2009/073533), and Berger et al, *Clin. Cancer Res.*, 14(10):3044-51 (2008).

A specific example of an anti-PD-1 antibody is MDX-1106 (nivolumab, see clinical trial number NCT00441337 and Kosak, US 20070166281 (pub. 19 Jul. 2007) at par. 42), a human anti-PD-1 antibody, preferably administered at a dose of 3 mg/kg.

Exemplary anti-B7-H1 antibodies include, but are not limited to, those described in the following publications: PCT/US06/022423 (WO/2006/133396, pub. 14 Dec. 2006), PCT/US07/088851 (WO/2008/083174, pub. 10 Jul. 2008) US 2006/0110383 (pub. 25 May 2006)

A specific example of an anti-B7-H1 antibody is MDX-1105 (WO/2007/005874, published 11 Jan. 2007)), a human anti-B7-H1 antibody. See U.S. Pat. Nos. 7,411,051, 7,052, 694, 7,390,888, and U.S. Published Application No. 2006/0099203 for additional anti-B7-DC antibodies.

The antibody can be a bi-specific antibody that includes an antibody that binds to the PD-1 receptor bridged to an antibody that binds to a ligand of PD-1, such as B7-H1. In some embodiments, the PD-1 binding portion reduces or inhibits signal transduction through the PD-1 receptor.

Other exemplary PD-1 receptor antagonists include, but are not limited to B7-DC polypeptides, including homologs and variants of these, as well as active fragments of any of the foregoing, and proteins that incorporate any of these. In a preferred embodiment, the protein includes the soluble portion of B7-DC coupled to the Fc portion of an antibody, such as human IgG, and does not incorporate all or part of the transmembrane portion of human B7-DC.

The PD-1 antagonist can also be a fragment of a mammalian B7-H1, preferably from mouse or primate, preferably human, wherein the fragment binds to and blocks PD-1 but does not result in inhibitory signal transduction through PD-1. The fragments can also be part of a fusion protein, for example an Ig fusion protein.

Other useful polypeptides PD-1 antagonists include those that bind to the ligands of the PD-1 receptor. These include the PD-1 receptor protein, or soluble fragments thereof, which can bind to the PD-1 ligands, such as B7-H1 or B7-DC, and prevent binding to the endogenous PD-1 receptor, thereby preventing inhibitory signal transduction. B7-H1 has also been shown to bind the protein B7.1 (Butte et al, *Immunity*, Vol. 27, pp. 1 11-122, (2007)). Such fragments also include the soluble ECD portion of the PD-1 protein that includes mutations, such as the A99L mutation, that increases binding to the natural ligands (Molnar et al, *PNAS*, 105: 10483-10488 (2008)). B7-1 or soluble fragments thereof, which can bind to the B7-H1 ligand and prevent binding to the endogenous PD-1 receptor, thereby preventing inhibitory signal transduction, are also useful.

PD-1 and B7-H1 anti-sense nucleic acids, both DNA and RNA, as well as siRNA molecules can also be PD-1 antagonists. Such anti-sense molecules prevent expression of PD-1 on T cells as well as production of T cell ligands, such as B7-H1, PD-L1 and/or PD-L2. For example, siRNA (for example, of about 21 nucleotides in length, which is specific for the gene encoding PD-1, or encoding a PD-1 ligand, and which oligonucleotides can be readily purchased commercially) complexed with carriers, such as polyethyleneimine (see Cubillos-Ruiz et al, *J. Clin. Invest.* 119(8): 2231-2244 (2009), are readily taken up by cells that express PD-1 as well as ligands of PD-1 and reduce expression of these receptors and ligands to achieve a decrease in inhibitory signal transduction in T cells, thereby activating T cells.

CTLA-4 Antagonists

Other molecules useful in combination therapies include CTLA-4 antagonists. For example, in some embodiments, the molecule is an agent that binds to CTLA4.

Dosages for anti-PD-1, anti-B7-H1, and anti-CTLA4 antibody, are known in the art and can be in the range of 0.1 to 100 mg/kg, with shorter ranges of 1 to 50 mg/kg preferred and ranges of 10 to 20 mg/kg being more preferred. An appropriate dose for a human subject is between 5 and 15 mg/kg, with 10 mg/kg of antibody (for example, human anti-PD-1 antibody, like MDX-1106).

Specific examples of an anti-CTLA4 antibody useful in the methods of the invention are Ipilimumab, also known as MDX-010 or MDX-101, a human anti-CTLA4 antibody, preferably administered at a dose of about 10 mg/kg, and Tremelimumab a human anti-CTLA4 antibody, preferably administered at a dose of about 15 mg/kg. See also Sammartino, et al, *Clinical Kidney Journal*, 3(2): 135-137 (2010), published online December 2009.

In other embodiments, the antagonist is a small molecule. A series of small organic compounds have been shown to bind to the B7-1 ligand to prevent binding to CTLA4 (see Erbe et al, *J. Biol. Chem.*, 277:7363-7368 (2002)). Such small organics could be administered alone or together with an anti-CTLA4 antibody to reduce inhibitory signal transduction of T cells.

ii. Exemplary ICI

The recombinant fusion polypeptides or the recombinant fusion polypeptide, recombinant polynucleotide, or recombinant fusion polypeptide conjugate may be used in combination with one or more ICI. Exemplary ICI include nivolumab (targets PD-1), pembrolizumab (targets PD-1), atezolizumab (targets PD-L1), avelumab (targets PD-L1), durvalumab (blocks the interaction of PD-L1 with the PD-1 (CD279)), cemiplimab (targets PD-L1), pidilizumab (targets Delta-like 1 (DLL1) as primary binding target and PD-1 as secondary binding target), vopratelimab (targets Inducible CO-Stimulator of T cells (ICOS) to generate an anti-tumor immune response), danvatirsen, cetrelimab, and ipilimumab (targets CTLA-4).

b. Anti-Inflammatory Agents

Second active agents used in combination with the recombinant fusion polypeptide, recombinant polynucleotide, or recombinant fusion polypeptide conjugate may be proteins, peptides, carbohydrates, nucleic acids, lipids, small molecules, or combinations thereof for treating inflammatory or autoimmune diseases. In some embodiments, the second active agent is an agent that is known in the art for treatment of inflammatory or autoimmune diseases. Exemplary agents include analgesics, non-steroidal anti-inflammatory drugs, biologic disease-modifying anti-rheumatic drugs (DMARDs) that target components of the immune response. Some such therapies target excessive inflammatory mediators, released by infiltrating lymphocytes that are responsible for tissue destruction. TNF-α antagonist are considered by some to be the most efficient of conventional biologics to treat inflammation (Audo, et al., *Cytokine*, 63(2):81-90 (2013)). Others targets in the TNF family include receptor activator for nuclear factor kappa-beta ligand (RANKL) and its receptor RANK, and osteoprotegerin (OPG) (Lamhamedi-Cherradi, et al., *Nature immunology* 4(3):255-60 (2003)).

Therefore, the second active agent can be one that modulates immune cells. The active agent can reduce or inhibit the proliferation or activity of pro-inflammatory immune cells, induce or increase the proliferation or activity of anti-inflammatory immune cells (e.g., regulatory T cells), or any combination thereof. In some embodiments, the second active agent reduces the expression or circulation of one or more pro-inflammatory molecules, including, but not limited to TNF-α, IL-1α, IFN-γ, IL-2, 11-6, IL-8, IL-1β, TGF-β, IL-17, IL-6, IL-23, IL-22, IL-21, prostanoids, and matrix metalloproteinases (MMPs).

2. Dosage and Treatment Regimes for Combination Therapies

The methods of treatment disclosed herein typically include treatment of a disease or symptom thereof, or a method for achieving a desired physiological change, including administering to an animal, such as a mammal, especially a human being, an effective amount of the recombinant fusion polypeptides, the recombinant polynucleotides, or the recombinant fusion polypeptide conjugates to treat a proliferative, autoimmune, or fibrotic disease, symptoms thereof, or to produce the physiological change. In some embodiments, the recombinant fusion polypeptide, the recombinant polynucleotide, or the recombinant fusion polypeptide conjugate is in combination with an additional active agent. The recombinant fusion polypeptide, the recombinant polynucleotide, or the recombinant fusion polypeptide conjugate and the additional active agent can be administered together, such as part of the same composition, or administered separately and independently at the same time or at different times (i.e., administration of the recombinant fusion polypeptide, the recombinant polynucleotide, or the recombinant fusion polypeptide conjugate and the second active agent is separated by a finite period of time from each other). Therefore, the term "combination" or "combined" is used to refer to either concomitant, simultaneous, or sequential administration of the recombinant fusion polypeptide, the recombinant polynucleotide, or the recombinant fusion polypeptide conjugate and the second active agent. The combinations can be administered either concomitantly (e.g., as an admixture), separately but simultaneously (e.g., via separate intravenous lines into the same subject; one agent is given orally while the other agent is given by infusion or injection, etc.), or sequentially (e.g., one agent is given first followed by the second).

In preferred embodiments, administration of the recombinant fusion polypeptide, the recombinant polynucleotide, or the recombinant fusion polypeptide conjugate in combination with the second active agent achieves a result greater than when the recombinant fusion polypeptide, the recombinant polynucleotide, or the recombinant fusion polypeptide conjugate and the second active agent are administered alone or in isolation (i.e., the result achieved by the combination is more than additive of the results achieved by the individual components alone). In some embodiments, the effective amount of one or both agents used in combination is lower than the effective amount of each agent when administered separately. In some embodiments, the amount of one or both agents when used in the combination therapy is sub-therapeutic when used alone.

A treatment regimen of the combination therapy can include one or multiple administrations.

In some embodiments, the recombinant fusion polypeptide, the recombinant polynucleotide, or the recombinant fusion polypeptide conjugate is administered prior to the first administration of the second active agent. In other embodiments, the recombinant fusion polypeptide, the recombinant polynucleotide, or the recombinant fusion polypeptide conjugate is administered simultaneously with the first administration of the second active agent. In other embodiments, the recombinant fusion polypeptide, the recombinant polynucleotide, or the recombinant fusion polypeptide conjugate is administered after the first administration of the second active agent.

The recombinant fusion polypeptide, the recombinant polynucleotide, or the recombinant fusion polypeptide conjugate can be administered at least 1, 2, 3, 5, 10, 15, 20, 24 or 30 hours or days prior to or after administering of the second active agent.

Dosage regimens or cycles of the agents can be completely, or partially overlapping, or can be sequential. For example, in some embodiments, all such administration(s) of the recombinant fusion polypeptide, the recombinant polynucleotide, or the recombinant fusion polypeptide conjugate occur before or after administration of the second active agent. Alternatively, administration of one or more doses of the recombinant fusion polypeptide, the recombinant polynucleotide, or the recombinant fusion polypeptide conjugate can be temporally staggered with the administration of second therapeutic agent to form a uniform or non-uniform course of treatment whereby one or more doses of the recombinant fusion polypeptide, the recombinant polynucleotide, or the recombinant fusion polypeptide conjugate are administered, followed by one or more doses of second active agent, followed by one or more doses of the recombinant fusion polypeptide, the recombinant polynucleotide, or the recombinant fusion polypeptide conjugate; or one or more doses of second active agent are administered, followed by one or more doses of the recombinant fusion polypeptide, the recombinant polynucleotide, or the recombinant fusion polypeptide conjugate, followed by one or more doses of second active agent; etc., all according to whatever schedule is selected or desired by the researcher or clinician administering the therapy.

An effective amount of each of the agents can be administered as a single unit dosage (e.g., as dosage unit), or sub-therapeutic doses that are administered over a finite time interval. Such unit doses may be administered on a daily basis for a finite time period, such as up to 3 days, or up to 5 days, or up to 7 days, or up to 10 days, or up to 15 days or up to 20 days or up to 25 days.

Typically, the first active agent and the second active agent are administered at effective amounts for each of the agent. The effective amounts for each agent may be between about between about 0.1 mg/kg and about 100 mg/kg of the body weight of the patient in an injection dose. Suitable amounts for each agent include between about 0.1 mg/kg and about 500 mg/kg, between about 0.1 mg/kg and about 250 mg/kg, between about 0.1 mg/kg and about 100 mg/kg, between about 0.1 mg/kg and about 80 mg/kg, and between about 0.1 mg/kg and about 60 mg/kg, such as between about 0.5 mg/kg and about 20 mg/kg, or between about 1 mg/kg and about 10 mg/kg. Specific concentrations for each agent include 0.1 mg/kg, 0.2 mg/kg, 0.3 mg/kg 0.4 µM, 0.5 mg/kg, 0.6 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, and 50 mg/kg.

V. Kits

Medical kits are also disclosed. The medical kits can include, for example, a dosage supply of the recombinant fusion polypeptide, the recombinant polynucleotide, or the recombinant fusion polypeptide, alone or in combination with a second therapeutic agent. When in combination with a second therapeutic agents, the active agents can be supplied alone (e.g., lyophilized), or in a pharmaceutical composition (e.g., an admixture). The active agents can be in a unit dosage, or in a stock that should be diluted prior to administration. In some embodiments, the kit includes a supply of pharmaceutically acceptable carrier. The kit can also include devices for administration of the active agents or compositions, for example, syringes. The kits can include printed instructions for administering the compound in a use as described above.

The present invention will be further understood by reference to the following non-limiting examples.

EXAMPLES

Example 1. miLZ-TRAIL Variants with High Expression Levels and Low Immunogenicity Materials and Methods Structural elements incompatible with clinical use were identified using in silico analysis (FIG. 1A, boxed regions). Thirty expression constructs were made and tested for expression levels.

Constructs were cloned into pSX2 plasmid (Scarab Genomics). Transformed E. coli cells (strain SG6620; Scarab Genomics) were grown at 28° C. in TB medium and protein expression was induced with 0.02-1 mM IPTG at a cell density of about 2 absorbance units (AU) (A600). Cells were grown over different periods of time, collected by centrifugation and lysed using BugBuster. The TRAIL contents were analyzed by SDG-PAGE.

Figure 1B:
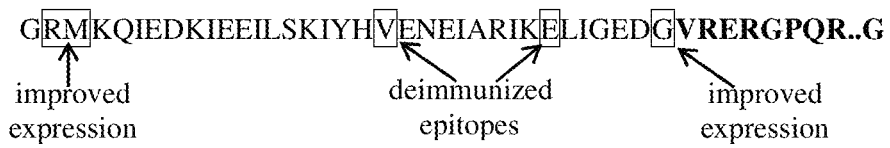
Figure 1C:
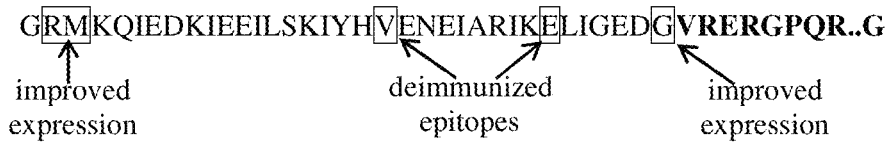
Figure 1D:
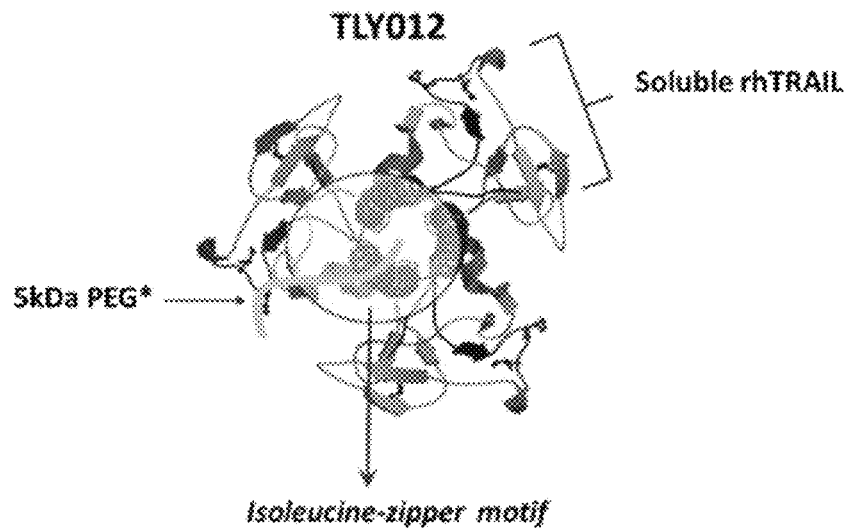
FIG. 1D is a diagram showing the structural elements of TLY012, each monomer of the trimer having the amino acid sequence SEQ ID NO:31.

Two lead sequences were selected based on enhanced expression levels of soluble protein. Both sequences were designed without a HisTag at the N-terminus and amino acid substitutions were made in the iLZ domain to disrupt immunogenic epitopes (FIG. 1B) indicated with arrows). A total amount of 400 mg protein was made for further pegylation experiments.

Proteins were purified using NTA agarose and tested for purity, thermodynamic stability and biological activity. iLZ-TRAIL-containing cells were lysed and supernatant containing high salt (1M NaCl) was prepared by centrifugation. Nucleic acids were digested using benzonase and the resultant cell lysate was incubated with Zn-NTA resin (batch or column) in the presence of low imidazole (typically 10 mM) until the binding capacity of the resin was saturated with respect to iLZ-TRAIL binding. The resin was washed with high-salt buffer in the presence of low imidazole as a batch or as a column content and iLZ-TRAIL was eluted with 125-250 mM imidazole. Eluted proteins were dialyzed against the buffers required for specific assays.

Results

The data demonstrated high purity (over 95%) of the protein preparations. Significantly higher thermodynamic stability was observed in the Thermal Shift assay compared to the HisTag-iLZ-TRAIL protein prototype (FIG. 2A). HisTag-iLZ-TRAIL produced two peaks: the first one in the range of 55-75° C. and the second—in the range of 75-98° C. miLZ-TRAIL had just a small shoulder instead of the first peak, while its second peak was larger than the one observed for His-tag-iLZ-TRAIL. Both lead candidates demonstrated about 5-fold higher biological activity in the cell viability bioassay (FIG. 2B). Table 1 shows the IC50 (nM) of the tested polypeptides.

miLZ-TRAIL could be repeatedly frozen and thawed (up to 5 cycles was tested) without significant loss of its functional activity (cell assay) or noticeable changes in its IEX-HPLC profile.

TABLE 1

The IC50 (nM) of the polypeptides tested in FIG. 2B.

| Protein | IC50, nM |
|---|---|
| His-iLZ-TRAIL | 0.07670 |
| miLZ-TRAIL #5-06 | 0.01558 |
| miLZ-TRAIL#5-05 | 0.01787 |

Example 2. In Vitro Bioactivity of PEGylated Leading Compounds (as TLY012 Leads) for In Vivo Use Materials and Methods In addition to the standard physico-chemical characterization, the leads were tested for the target potency and off-target toxicity. Initially, selective apoptotic activities of various TLY012 leads were tested in normal (off-target) and myofibroblasts (target cells) by utilizing quiescent and activated primary human hepatic stellate cells (HSCs) respectively. Briefly, quiescent and culture-activated HSCs were incubated with TLY012 leads and cell viability was determined by cell cytotoxicity assays.

TLY012 is a PEGylated form of rhTRAIL, genetically fused to a humanized coiled-coil isoleucine "zipper" (miLZ) at the N-terminus. It is a DR4/DR5 receptor agonist and as such is known to induce apoptosis in Human colon adenocarcinoma cells COLO 205 resulting in inhibition of cell proliferation. CELL TITER-GLO™ (Promega, WI) was used to measure luminescence in conventional luciferase assay system. This assay is a homogeneous method to determine the number of metabolically active cells based on quantitation of the ATP present. Addition of a single reagent (CELLTITER-GLO® Reagent) directly to the cells cultured in serum-supplemented medium results in cell lysis and generation of a luminescent signal proportional to the amount of ATP present which is directly proportional to the number of cells present in culture.

Assay Procedure. TLY012 samples were tested in triplicate over a range of serial dilutions from 1000 ng/mL to 0.05 ng/mL. Initially 2× concentration of TLY012 was prepared by making two 10× dilutions of TLY012. All other concentrations were made sequentially using one ⅒-fold and eight ⅓-fold dilutions. Dilutions were made using sterile 12-channel reservoir. 50 µl of each dilution of reference standard and test samples were transferred to the 96-well plate according to the plate map. The 96-well plates were placed into a 37±1.0° C.; 5±0.5% CO2; ≥85% relative humidity cell culture incubator in a single layer and incubated for 1±0.5 hours until cells are ready. 20000 cells in 50µ 1 growth medium were plated in a 96-well plate with previously added TLY012 dilutions and assayed for 22-24 hours. DR5 receptor agonist TLY012 binds to the receptor and causes cytotoxic effect. The level of ATP present in culture shows metabolic activity of the COLO 205 cells. As a result, inhibition of cell proliferation is measured by adding the CELL TITER-GLO™ solution to the cells, the lysed cells release ATP. The reaction between released ATP and Cell Titer Glow solution generates a stable "glow-type" luminescent signal.

The growth medium was RPMI1640 with 10% FBS, glutamine, penicillin/streptomycin solution. Using a 12-channel pipette, cell suspension was transferred (50 µL/well–2×10⁴ cells) to inner 60 wells of the 96-well assay plate. In addition, wells BCD12 were loaded with cell suspension. Wells EFG12 and B1-G1 were loaded with medium alone. Remaining wells contained 100 µL of assay media. The 96-well plates were placed into a 37±1.0° C.; 5±0.5% CO2; ≥85% relative humidity cell culture incubator in a single layer and incubated for 22-24 hours. After incubation CELL TITER-GLO™ Luciferase Assay System solution was added to the cells. Cell suspension was transferred to the white 96-well plates and luminescence was measured by BIOTEK plate reader.

Data Analysis.

Data were analyzed using BioTek Gen5secure software. The dose response curves were generated using the four-parameter fit logistic model and the $IC_{50}$ values for reference standard and test samples were calculated. Potency of the test sample is expressed as the ratio of the $IC_{50}$ values of the test and reference standard samples.

Statistical Analysis.

For the statistical analysis, the measurement of ATP release as a function of TLY012 concentration was modeled using a four-parameter logistic model. The statistical model applied to this assay is given by the following nonlinear regression equation:

$$Y=(A-D)/(1+(X/C)^B)+D$$

In this equation Y (Relative Luminescence Units) is a function of X (concentration) and the four parameters A, B, C ($IC_{50}$) and D have a specific interpretation. Asymptote A refers to the upper response limit, asymptote D refers to the lower response limit, $IC_{50}$ refers to the inhibitory concentration to inhibit 50% of the maximum signal, and B is a scale parameter related to the shape and steepness of the curve itself. By fitting this model to the reference standard and test samples analyzed within the same assay, relative potency (RP) was calculated as:

$$RP=IC_{50}(\text{reference})/IC50(\text{test})$$

when both concentrations produce the same effect.

All relative potency values as well as EC50 and four parameters values were calculated using BIOTEK software Gen5 secure.

Results

TLY012 leads demonstrated no off-target toxicity in quiescent stellate cells, but showed strong potency only in activated stellate cells (FIG. 3). Importantly, TLY012 leads did not show any off-target toxicity at the concentrations up to 100 nM in primary human hepatocytes, while demonstrating subnanomolar potency (0.142 nM in activated HSCs and 0.01545 nm in colorectal cancer cells COLO-205, FIGS. 3 and 4) in cell viability bioassays. The IC50 values for the PEGylated polypeptides are shown in Table 2.

TABLE 2

The IC50 (nM) of the PEGylated polypeptides tested in FIG. 4.

| Protein | IC50, nM |
| --- | --- |
| PEG-TRAIL | 0.01545 |
| His-TRAIL-PEG | 0.1414 |

Example 3. miLZ-TRAIL has Significantly Increased Production Yield in *E. coli* when Compared to Compositions with Histidine-Tag-iLZ-TRAIL Materials and Methods Constructs were cloned into pSX2 plasmid (Scarab Genomics). Transformed *E. coli* cells (strain SG6620; Scarab Genomics) were grown at 28° C. in TB medium and protein expression was induced with IPTG at a cell density of about 2 AU (A600). Cells were grown overnight in TB medium, collected by centrifugation and lysed using BUG-BUSTER. The TRAIL contents were analyzed by SDG-PAGE.

The following fusion polypeptides were used in this study:

```
Original His-tag-TRAIL containing sequence
SEQ ID NO: 3 (in bold) and
SEQ ID NO: 15 (italic)
MGHHHHHHHHPGMCGGKQIEDKIEEILSKIYHIENEIARIKKL

IGEDGVRERGPQRVAAHITGTRGRSNTLSSPNSKNEKALGRKI

NSWESSRSGHSFLSNLHLRNGELVIHEKGFYYIYSQTYFRFQEE

IKENTKNDKQMVQYIYKYTSYPDPILLMKSARNSCWSKDAEYG

LYSIYQGGIFELKENDRIFVSVTNEHLIDMDHEASFFGAFLV

G miLZ-TRAIL (Clone #5) containing
SEQ ID NO: 4 (in bold) and
SEQ ID NO: 15 (italic)
MGRMKQIEDKIEEILSKIYHVNEIARIKELIGEDGVRERGPQ

RVAAHITGTRGRSNTLSSPNSKNEKALGRKINSWESSRSGHS

FLSNLHLRNGELVIHEKGFYYIYSQTYFRFQEEIKENTKNDK

QMVQYIYKYTSYPDPILLMKSARNSCWSKDAEYGLYSIYQGG

IFELKENDRIFVSVTNEHLIDMDHEASFFGAFLVG
```

Results

The efficiency of the histidine-tag-iLZ-TRAIL (Chae, et al., *Molecular cancer therapeutics* 9(6):1719-29 (2010)) production in rich media (TB) did not exceed 100 mg/L. The histidine-tag-iLZ-TRAIL produced in minimal media was unstable inside cells and could not be stored as frozen cell mass.

The efficiency of miLZ-TRAIL production was around 1 g/ml and the protein was stored over months within frozen cells.

Example 4. The miLZ-TRAIL has Significantly Increased Solubility

Materials and Methods

The fusion polypeptides used in this study were the same as those in Example 3.

Results

The histidine-tag-iLZ-TRAIL had a very limited solubility. The maximum concentration of His-iLZ-TRAIL used for PEGylation in solution at pH 5.0 did not exceed 100 μg/ml (Chae et al. (2010) *Mol Cancer Ther.* 9(6): 1719-1729). The latest PEGylation experiments at pH 5.0 were done at the starting concentration of miLZ-TRAIL of 15 mg/ml. No solubility issues were observed, and the final product met all quality control ("QC") requirements.

Example 5. PEGylated miLZ-TRAIL Shows Significantly Increased Solubility and Stability when Compared to the PEGylated TRAIL in the Art Materials and Methods The fusion polypeptides used in this study were the same as those in Example 4.

Results

PEGylated miLZ-TRAIL formulation was stable at concentrations up to 25 mg/ml in the presence of physiological concentrations of salt. The formulation retained the same concentration of protein, showed no detectable precipitation and demonstrated the same protein pattern when analyzed by IEX-HPLC. The stability studies demonstrated that formulated PEGylated miLZ-TRAIL (21-22 mg/mi) was resistant to multiple freeze-thaw cycles both in term of biological activity and the appearance in HPLC analysis.

Melting/aggregation curves having three readily discernable phases were observed for all iLZ-TRAIL and miLZ-TRAIL variants when the protein was heated in the presence of a fluorescent dye sensitive to protein aggregation/denaturation using an ENZO PROTEOSTAT aggregation kit.

Phase 1 (25-55° C.), which reflected weak protein-dye interactions, was more pronounced at pH 8.0 than at pH 6.0. This may have been caused by the initial differences in the exposure of hydrophobic regions or by charge-mediated binding background.

Phase 2 (60-80° C. at pH 8.0 and 55-75° C. at pH 6.0) and phase 3 (80-98° C. at pH 8.0 and 75-98° C. at pH 6.0) peaked at temperature values that were similar for all variants melted in the same buffer.

Phase 2 at pH 6.0 showed the highest signal a few degrees lower than phase 2 at pH 8.0.

The variant with the lowest predicted immunogenicity, miLZ-TRAIL (1876 (K32E, I23V), corresponding to miLZ sequence of SEQ ID NO:4), had a less pronounced phase 1 at pH 6.0 as compared to all other variants.

The results are shown in FIGS. 5A-5H.

Example 6. PEGylated miLZ-TRAIL Demonstrates Significantly Increased Potency (IC50, In Vitro) when Compared to the PEGylated TRAIL with HIS-Tag Materials and Methods The fusion polypeptides used in this study were the same as those in Example 4.

Results

The biological activity of the final PEGylated TRAIL is 9-fold higher compared to the prototype (FIG. 3 and Table 2) when measured as cytotoxicity in a cell assay with COLO 205 cells.

Example 7. PEGylated miLZ-TRAIL Pharmacokinetic (PK) Parameters in Primates

Materials and Methods

PK parameters were addressed in Cynomolgus monkeys. This was a single dose, parallel group, dose escalation study in 5 males and 5 females normal Cynomolgus monkeys ranging in age from 34 to 44 months. At the start date of the study body weights ranged from 2.9 to 3.9 kg for males and 2.9 to 3.2 kg for females. The study design is summarized in Table 3. Blood samples were collected at time point indicated in Table 3 and serum samples prepared for analyzing drug levels.

TABLE 3

Test drug assignment and blood specimen collection schedule in monkeys.

| Treatment Group | Route of administration | # of monkeys | Dose mg/kg | Dose concentration. mg/mL | Blood specimen collection times |
| --- | --- | --- | --- | --- | --- |
| 1 | Intravenous | 1M/1F | 10 | 4 | Predose, 0.25, 0.5, 1, 3, 6, 12, 24, 48, 72, 120, 144, 192, 264, and 360 hours post dose |
| 2 | Subcutaneous | 1M/1F | 2 | 0.8 | Predose, 1, 6, 12, 24, 48, 72, 120, 192, 264, and 360 hours post dose |
| 3 | | 1M/1F | 10 | 4 | |
| 4 | | 1M/1F | 50 | 20 | |

Sample Analysis.

A sandwich enzyme-linked immunosorbent assay (ELISA) for human TRAIL was developed to measure the concentrations of TLY012 in monkey serum. Briefly, serum samples were diluted in 0.5% normal monkey serum and incubated with anti-TRAIL capturing antibodies immobilized on ELISA plates. Test samples were analyzed at 1:200-1:168000 dilutions (depending on the predicted concentrations) to fit into the range of the standard curve (97 pg/mL-12.5 ng/mL). All data within the assay range were reported and provided for pharmacokinetic analysis PK Parameters Analysis.

A compartment model independent pharmacokinetic analysis was conducted on dose and serum concentration-time data with Phoenix 64 WinNonlin software. The parameters addressed: maximum serum concentrations ($C_{max}$), time ($T_{max}$) to reach $C_{max}$, time ($T_{last}$) to reach the last quantifiable concentration ($C_{last}$), elimination half-life (t½). Area under the curve from zero to $C_{last}$ ($AUC_{last}$), the total area under the curve from zero to infinity (AUC). Total systemic clearance (CL) and steady state volume of distribution ($V_{ss}$) was calculated for IV group. Clearance (CL/F) and volume of distribution (Vz/F) and bioavailability (F) was computed for the SC groups. In addition, dose-exposure relationship was evaluated by linear regression analysis.

Results

Following 10 mg/kg IV dose, TLY012 serum concentrations declined in a log-linear manner with first order terminal elimination half-lives (Table 4) of 30.9 hours in female and 38.0 hours in males. Serum concentrations appeared to decline in a log-linear manner with a slight deviation towards a barrel shape, suggesting a nonlinear elimination process (FIGS. 7A-7D).

TABLE 4

| | | | Dose | $t_{1/2}$ | $T_{max}$ | $C_{max}$ | $T_{last}$ | $C_{last}$ | AUC | $AUC_{ext}$ |
|---|---|---|---|---|---|---|---|---|---|---|
| Group | ID | Sex | mg/kg | h | h | ug/mL | h | ug/mL | h*ug/mL | % |

TLY012 Pharmacokinetic parameters after IV administration in Cynomolgus monkeys

| 1 | 1 | M | 10 | 38.0 | 0.250 | 289 | 360 | 0.643 | 8590 | 0.411 |
| | 401 | F | 10 | 30.9 | 0.250 | 319 | 360 | 0.322 | 7780 | 0.185 |

Following SC doses (2, 10, or 50 mg/kg) of TLY012 (Groups 2-4), time to reach maximum ($T_{max}$) serum concentrations ranged from 6 to 72 hours post dose. Serum concentrations following 2 mg/kg declined in an apparent log linear manner with first order terminal elimination half-lives of 34.7 hours in the male and 42.7 hours in the female. The half-life values for the 10 mg/kg group were 20.7 h in male and 30.4 h in female, and in the 50 mg/kg group-43.9 h in male and in 46.7 female. The absolute bioavailability of TLY012 appeared to increase with dose following SC administration to monkeys. After 2, 10 and 50 mg/kg TYL012 administered to males, the absolute bioavailability (F %) was 37.4%, 75.4% and 77.8%, respectively. In females, F was 53.7%, 79.6% and 114% after administration of 2, 10 and 50 mg/kg TYL012.

transplantation, mice were injected with TLY012 via intravenous (IV) injection (10 mg/kg, every other day) for 2 weeks, while control mice received PBS. Western blot was performed on tissue extracts with antibodies against GAPDH (Santa Cruz 5 Biotechnology, sc-1694), α-SMA (Sigma, A2547), GRP78 (Santa Cruz Biotechnology, sc-13968), DR4 (Abcam, Cambridge, Mass., #13890), DR5 (Abcam, #47179), PDGF-Rb (Santa Cruz Biotechnology, sc-432), and Cl.PARP-1 (Cell Signaling Technology, #5625).

Comparative quantitative RT-PCR (qPCR) was performed in the tumor sample for fibrogenic markers. qPCR was performed in triplicate for each sample using fast SYBR Green Master Mix (Thermo Fisher Scientific) and StepOnePlus Real-Time PCR System (Thermo Fisher Scientific).

TABLE 5

TLY012 Pharmacokinetic parameters after SC administration in Cynomolgus monkeys

| Group | ID | Sex | Dose mg/kg | $t_{1/2}$ h | $T_{max}$ h | $C_{max}$ ug/mL | $T_{last}$ h | $C_{last}$ ug/mL | AUC h*ug/mL | F % | $AUC_{ext}$ % |
|---|---|---|---|---|---|---|---|---|---|---|---|
| 2 | 101 | M | 2 | 34.7 | 6.00 | 10.8 | 264 | 0.0999 | 642 | 37.4 | 0.779 |
| | 501 | F | 2 | 42.7 | 12.0 | 12.1 | 264 | 0.196 | 836 | 53.7 | 1.45 |
| 3 | 201 | M | 10 | 20.7 | 24.0 | 51.7 | 360 | 0.0501 | 6480 | 75.4 | 0.0231 |
| | 601 | F | 10 | 30.4 | 48.0 | 52.7 | 264 | 0.376 | 6190 | 79.6 | 0.266 |
| 4 | 301 | M | 50 | 43.9 | 72.0 | 186 | 264 | 16.5 | 33400 | 77.88 | 3.13 |
| | 701 | F | 50 | 46.7 | 24.0 | 296 | 360 | 8.39 | 44200 | 114 | 1.28 |

Over the dose range (2-50 mg/kg) studied, maximum serum ($C_{max}$) concentrations increased dose proportionately and total area under the curve (AUC) while exposure (AUC) increases over-proportionately with dose. The dose increased 25-fold while the exposure increased 40 to 70-fold (Table 5).

Elimination half-lives ranged from 20.7 to 46.7 hours. While in comparison, the $t_{1/2}$ of His-iLZ-TRAIL (containing SEQ ID 3 and SEQ ID 15) injected IV into monkeys was just 0.9 h as compared to the $t_{1/2}$ of 8.6 h observed for same protein after PEGylation (*Hepatology*; 64(1): 209-223 (2016)).

Example 8. TLY012 Induces Apoptosis and Reduced the Fibrosis in In Vivo Analysis of PSC/ASPC-1 Xenograft Materials and Methods Six-week-old athymic nude mice were anesthetized for all procedures $5\times10^6$ ASPC-1 cells (human pancreas adenocarcinoma ascites metastasis cell line derived from nude mouse xenografts initiated with cells from the ascites of a 62-year-old female Caucasian patient with cancer of the pancreas) were mixed with $5\times10^4$ PSC cells and injected in a subcutaneous in athymic nude mice. Before injection, the cells were trypsinized, counted, washed twice in 1×PBS and resuspended in 100 μl of Matrigel® matrix (Corning), and injected between the scapulae. Two weeks after the tumor The expression levels of target genes were normalized to the expression of 18s and calculated based on the comparative cycle threshold Ct method ($2^{-\Delta\Delta Ct}$).

Collagen deposition was detected with Masson's Trichrome staining and microscopy.

Results

Figure 8A:
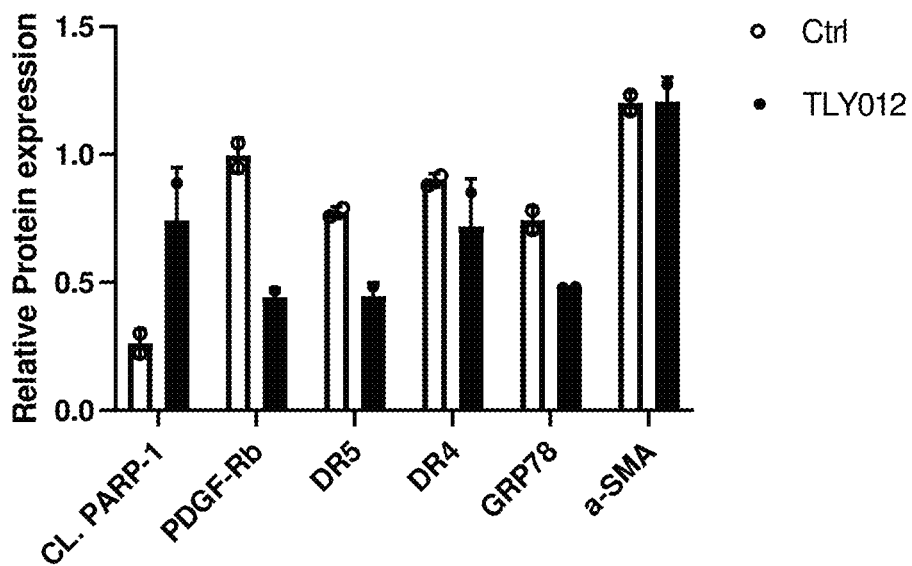
FIG. 8A is a bar graph showing results from the Western blot analysis of tissue extracts for α-SMA, GRP78, DR4, DR5, PDGF-Rb, and Cl.PARP-1

The results from the Western blot analysis showed, compared to PBS-treated controls, markedly reduced levels of PDGF-Rb, DR5, DR4, and GRP78. The level of Cl.PARP-1 was increased (FIG. 8A).

The antitumor/fibrogenic efficacy of TLY012 was investigated in PSC/AsPC-1 (human primary pancreatic stellate cells/pancreatic adenocarcinoma cell line) tumor-bearing mice. The tissue samples treated with TLY012 showed high levels of cleaved PARP-1, a representative apoptosis marker. Also, PDGF-Rb, DR5, and DR4 protein levels are significantly decreased in the tumor as assessed by Western blotting. The levels of mRNA Acta2, Pdgf-r, and Tgf-b are decreased in TLY012 treatment, and the collagen positive signals were highly increased in the tissue samples of PSC-AsPC-1 mixed tumor, but TLY012 treatment reduced the levels of collagen as assessed by Masson's Trichrome staining.

Figure 8B:
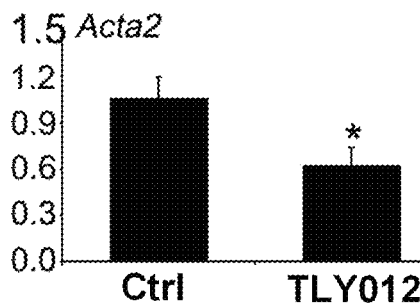
FIGS. 8B-8D are bar graphs showing the mRNA expression levels of fibrogenic markers Acta2, TGF-b, and Pdgf-r.
Figure 8C:
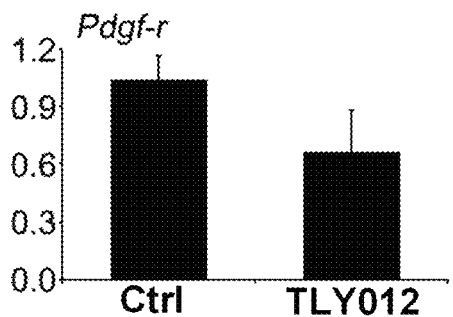
Figure 8D:
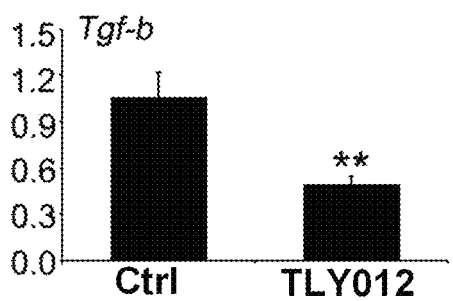

The expression levels of Acta2 and Tgf-β, when normalized to GAPDH, were significantly reduced in TLY012 treated group when compared to control group (FIGS. 8B-8D).

Captured image of Masson's Trichrome staining for collagen positive area after TLY012 treatment and digital quantification showed markedly reduced collagen deposition.

Example 9. TLY012 and Sorafenib Combination Treatment Reduced the Tumor Size in PSC/ASPC-1 Xenografts Materials and Methods ASPC-1 cells or ASPC-1 cells with PSC CM (PSC-conditioned medium) were incubated in culture wells in vitro for 24 h followed by either control treatment (DMSO) or treatment with TLY012 at 100 ng/mL and 1 µM of Sorafenib for 8 h. Microscopy images were taken from the culture wells after 8 h incubation.

Mouse xenografts were generated as in Example 8. Two weeks after the tumor transplantation, mice were injected with TLY012 via intravenous (IV) injection (10 mg/kg, every other day) and/or sorafenib (20 mg/kg, oral everyday) for 2 weeks. The mice were euthanized when the tumor volume reached 1500 mm$^3$ and images of the excised xenografts recorded and tumor weight measured.

Results

Figure 9A:
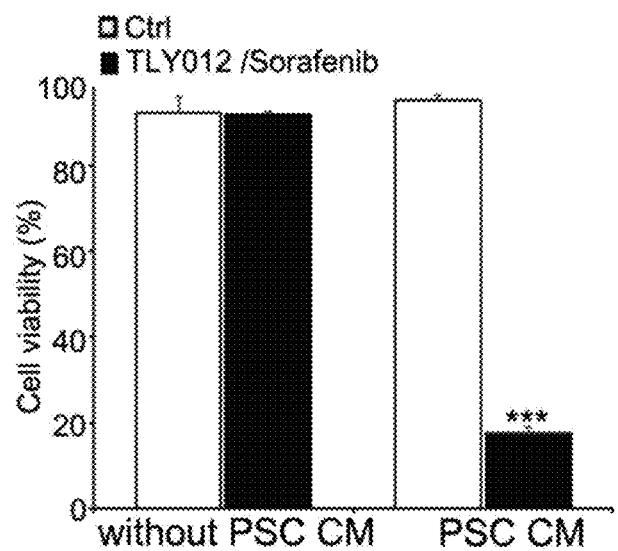
FIG. 9A is a bar graph showing cell viability (%) of ASPC-1 cells grown with or without PSC-CM and treated with combination of TLY012 and sorafenib.

Captured images of ASPC-1 cells, or ASPC-1 cells with PSC CM, incubated for 24h followed by TLY012 and Sorafenib treatment for 8h showed that ASPC-1 cells treated with TLY012 and Sorafenib for 8 h showed reduction in cell number relative to ASPC-1 cells with control treatment. The reduction in ASPC-1 cell number was significantly greater when ASPC-1 cells were with PSC CM and were treated with TLY012 and Sorafenib. This significant reduction was statistically significant relative to the number of ASPC-1 cells with PSC CM that received the control treatment, or relative to the ASPC-1 cells treated with TLY012 and Sorafenib for 8 h. The results are shown in FIG. 9A.

Figure 9B:
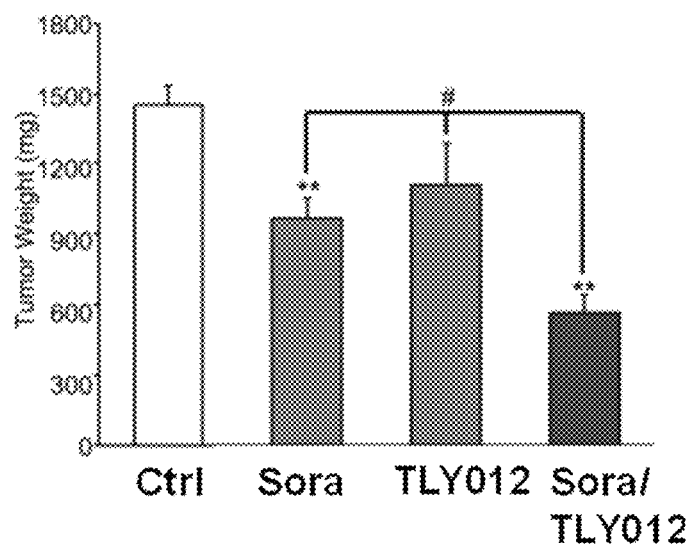
FIG. 9B is a bar graph showing the quantified data of tumor weight (mg) from ASPC-1/PSC xenografts obtained from mice treated with Sorafenib, TLY012, or the combination of TLY012 and Sorafenib.

FIG. 9B shows tumor weight (mg) from control and treated mice. The effect of the combination of was synergistic. Table 6 summarizes the data for FIG. 9B.

TABLE 6

Quantified data of tumor weight (mg) from ASPC-1/PSC xenografts obtained from mice treated with Sorafenib, TLY012, or the combination of TLY012 and Sorafenib.

| Group | Mean | S.E.M |
|---|---|---|
| Ctrl | 1454 | 79.71449 |
| Sorafenib | 967 | 89.83207 |
| TLY012 | 1109.5 | 180.3952 |
| Sorafenib/TLY012 | 567.6667 | 76.09059 |

This confirmed that the sensitization of the pancreatic cells with Sorafenib (multi-kinase inhibitor) highly increased the TLY012 induced apoptosis in AsPC-1 after pretreatment with conditioned culture medium from activated PSC. Also, the antitumor efficacy of TLY012 in PSC bearing AsPC-1 was investigated with 5×10$^6$ AsPC-1 cells mixed with 5×10$^4$ PSC cells with 100 µl of Matrigel® matrix (Corning) and injected s.c. in xenografted athymic mice. The data from FIG. 9 shows that Sorafenib sensitizes the antitumor effect in fibrogenic tumor priming with TLY012.

Example 10. DR5 Agonist, TLY012 Induced Apoptosis in Pancreatic CAF and aPSCs Alpha-SMA+MFBs is one of the major sources of cancer-associated fibroblast (CAF) and desmoplasia, known to contribute to the onset and progression of tumors with potent immunosuppressive properties in solid tumor. However, TRAIL-based therapy has received much attention because of its antitumor effect rather than the anti-fibrotic function. The potential anti-fibrotic role of TRAIL signaling on fibrosis-associated tumor microenvironment (TME) with CAF or α-SMA+MFBs, and immune cells, has not been previously reported. The main reason for immunotherapy treatment challenges in cancer treatment are deficient effector T cell responses and lack of immunogenicity. In particular, the presence of cancer-associated fibroblasts (CAFs), the major component of TME, is involved in regulating the innate immune system by interfering with the function of cytotoxic T cells. Stromal cells, including stellate cells, endothelial cells, and diverse immune cells, are known to be a source of TME for cancer survival and progression with potent immunosuppressive properties.

Materials and Methods

Human primary pancreatic stellate cells (PSCs) and stellate cell medium (SteCM) were obtained from ScienCell Research Laboratories (Carlsbad, Calif.). PSCs were cultured on Poly-L-Lysine coated plates in SteCM medium supplemented with 2% of FBS, 1% of stellate cell growth supplement, and 1% of penicillin/streptomycin solution according to the manufacturer's instructions. Pancreatic cancer associated fibroblasts (CAF08) and maintenance media (PC00B5) were obtained from Vitro Biopharma. 100 of PSCs were culture-activated for 7 to have the confluent population of activated cells or 2×10$^4$ cells of CAF08 were cultured on a 96 well microplate (Corning, CLS3917) for 24h and were incubated with TLY012 (at 30 ng/ml or 100 ng/ml) for 3h. After incubation, 50 µL of Caspase 3/7 substrate/lysis buffer was added to each well and incubated for 30 min after 30 min of equilibration period to room temperature. The luminescence of each sample was measured on a plate reader (Bio-Tek Instruments Inc) with parameters of 1 min lag time and 0.5 sec/well-read time (n=3).

For immunoblot, 100 of PSCs were culture activated on a 6 well plate for 7 days or 2×10$^5$ of CAF08 cells were plated on 6-well plates followed by control treatment or treatment with TLY012 (at 30 ng/ml or 100 ng/ml) for 3h. The lysates from the cells were tested for the presence of Cl.PARP-1 and SMA using Western bot.

Results

Figure 10:
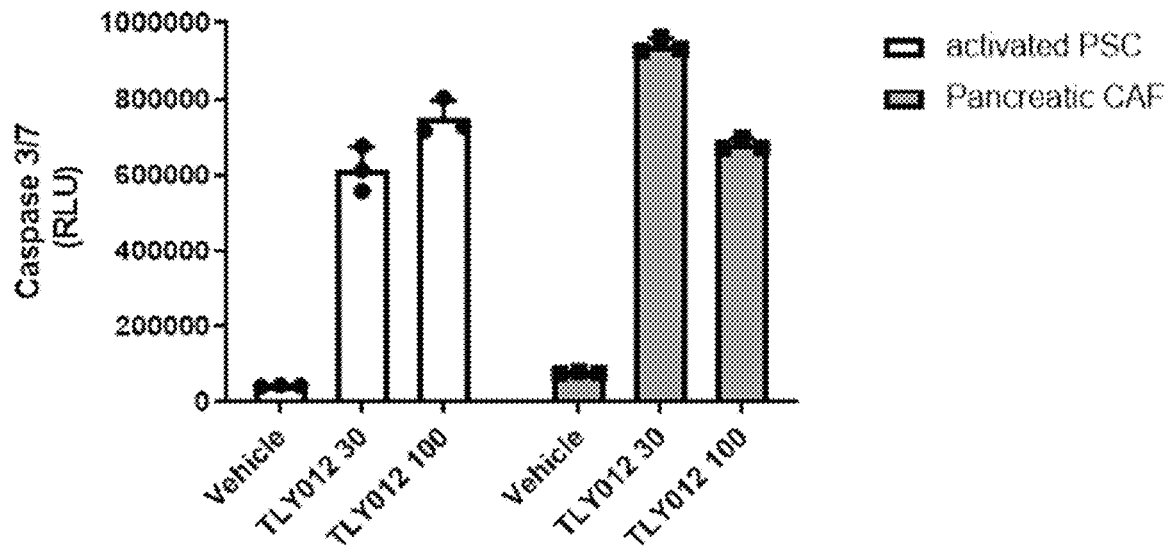
FIG. 10 is a bar graph showing caspase 3/7 activity (RLU) in pancreatic CAF cells treated with different doses of TLY012 as compared to caspase 3/7 activity (RLU) in activated PSC treated with the same doses of TLY012.

The luminescence from each well was reported as relative luminescence units (RLU) and the data showed that both PSCs and CAF08 cells had activated caspase 3/7 following TLY012 treatment, but not control treatment (FIG. 10).

The immunoblot test detected Cl.PARP-1 in both PSCs and CAF08 cells with TLY012 treatment. Cl.PARP-1 was not detected in the PSCs and CAF08 cells with control treatment. CAF08 cells under both treatments had significantly greater amounts of SMA than the PSCs under the two treatments.

This confirmed the TLY012 induced apoptosis in primary cancer-associated fibroblast originated from pancreatic cancer patients compared with activated primary human pancreatic stellate cells as assessed with Caspase3/7 activity assay and Western blotting by cleaved PARP-1. This study also found that pancreatic CAF highly expresses α-SMA protein compared to activated stellate cells.

Example 11. TLY012 Outperforms Other Cancer Therapeutics in Inducing Apoptosis in Human Pancreatic Cancer Associated Fibroblasts Materials and Methods Pancreatic cancer associated fibroblasts (CAF08) and maintenance media (PC00B5) were obtained from Vitro Biopharma and maintained in Pancreatic Stellate CAF maintenance media (Vitro Biopharma, Cat. No. PC00B5). About $2\times10^4$ cells were cultured on a 96 well microplate (Corning, CLS3917) for 24h and were incubated with 30 ng/ml TLY012 for 3h at dose dependent manner, or with cytotoxic agents Gemcitabine at 50 μM for 24 hours, Doxorubicin at 10 μM for 24 hours, Cisplatin at 50 μM for 24 hours, 5-Fluorouracil (5-FU) at 25 μg/mL for 24 hours, or Irinotecan at 10 μM for 24 hours, as indicated.

After incubation, 50 uL of Caspase 3/7 substrate/lysis buffer from Caspase3/7 Glo assay kit (Promega, Madison USA) was added to each well and incubated for 30 min after 30 min of equilibration period to room temperature. The luminescence of each sample was measured on a plate reader (Bio-Tek Instruments Inc) with parameters of 1 min lag time and 0.5 sec/well-read time (n=3).

For Western blot, $2\times10^5$ cells were plated on 6-well plates and were incubated with the same cytotoxic agents as indicated followed by Western blot detection of Cl.PARP-1, PD-L1, DR5, DR4, α-SMA, and β-actin.

Results

Figure 11:
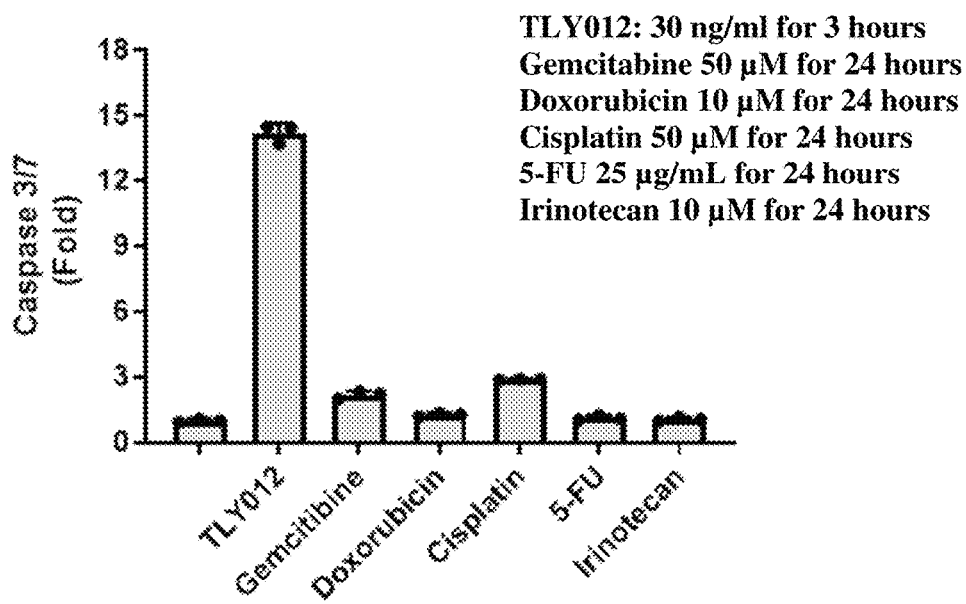
FIG. 11 is a bar graph showing fold increase in caspase 3/7 activity (Fold) in pancreatic CAF cells treated with the indicated various cytotoxic agents.

FIG. 11 shows the results of the luminescence reported as fold increase in luminescence (fold) from the different treated conditions. TLY012 outperformed other cancer therapeutics in activating caspase 3/7 in human pancreatic cancer associated fibroblasts.

The data showed that only TLY012 induced apoptosis among tested cytotoxic agents including Gemcitabine, Doxorubicin, Cisplatin, 5-FU, and Irinotecan (FIG. 11). Importantly, the protein levels of α-SMA were significantly decreased by TLY012 treatment in pancreatic CAF as assessed by Western blotting.

Example 12. TLY012 Induced Apoptosis, and Outperforms Other Cancer Therapeutics in Inducing Apoptosis, in Human Colon Cancer Associated Fibroblasts Materials and Methods Human Colon Carcinoma Fibroblasts HC-6231 were obtained from Cell Biologics (Catalog Number HC-6231) and maintained in fibroblast media (Cell Biologics, Catalog Number M2267). About $2\times10^4$ cells were cultured on a 96 well microplate (Corning, CLS3917) for 24h and were (a) incubated with TLY012 for 3h at dose dependent manner at doses 0 ng/ml, 10 ng/ml, 30 ng/ml, 100 ng/ml, or 1000 ng/ml; orb) incubated with TLY012 or with cytotoxic agents as indicated: 30 ng/ml TLY012 for 3h, Gemcitabine at 50 μM for 24 hours, Doxorubicin at 10 μM for 24 hours, Cisplatin at 50 μM for 24 hours, 5-FU at 25 μg/mL for 24 hours, or Irinotecan at 10 μM for 24 hours.

Then, 50 uL of Caspase 3/7 substrate/lysis buffer was added to each well and incubated for 30 min after 30 min of equilibration period to room temperature. The luminescence of each sample was measured on a plate reader (Bio-Tek Instruments Inc) with parameters of 1 min lag time and 0.5 sec/well-read time (n=3).

Results

Figure 12A:
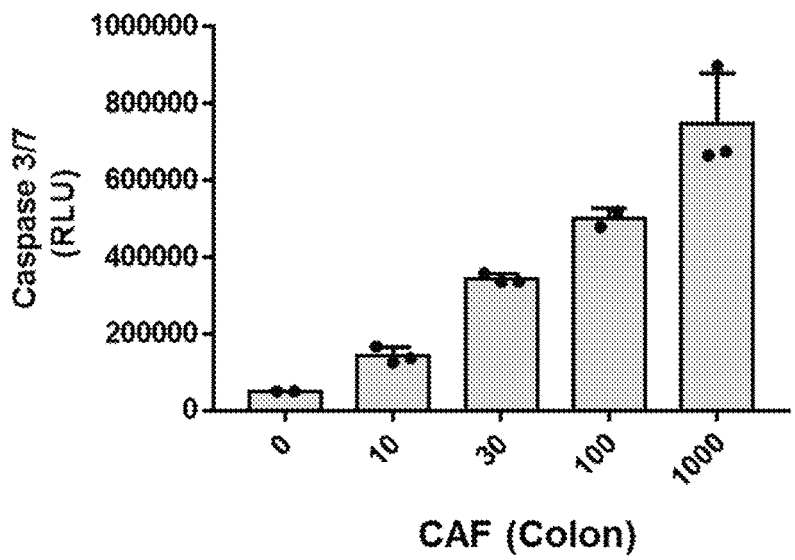
FIG. 12A is a bar graph showing caspase 3/7 activity (RLU) in colon CAF cells treated with different doses (ng/ml) of TLY012.
Figure 12B:
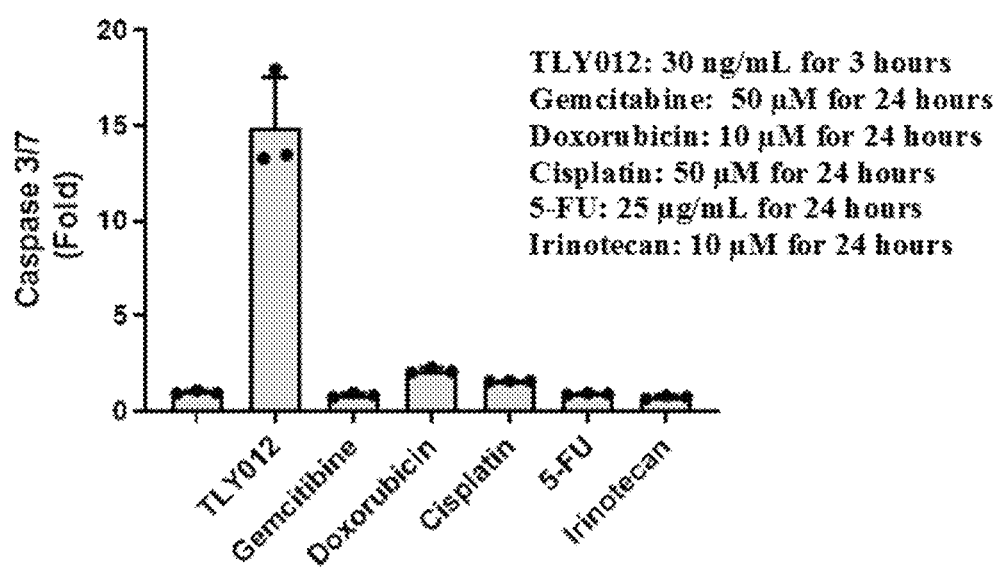
FIG. 12B is a bar graph showing fold increase in caspase 3/7 activity (Fold) in colon CAF cells treated with the indicated various cytotoxic agents.

FIG. 12A shows the results of the luminescence in relative luminescence units (RLU) from activated caspase 3/7 in Colon Carcinoma Fibroblasts treated with the different doses of TLY012 for 3 h. FIG. 12B shows the fold increase (Fold) in caspase 3/7 activation in the Colon Carcinoma Fibroblasts treated with the different cytotoxic agents at the indicated doses and times. TLY012

This study confirmed the TLY012 induced apoptosis in primary cancer-associated fibroblast originated from colon cancer patients as assessed with Caspase3/7 activity assay (FIG. 12A). TLY012 induced significantly greater apoptosis among tested cytotoxic agent including Gemcitabine, Doxorubicin, Cisplatin, 5-FU, and Irinotecan (FIG. 12B).

Example 13. CAFs Highly Express the Fibrogenic Markers and PD-L1/2

Programmed Cell Death Protein 1 (PD-1) on T cells and PD-1 ligands PD-L1 or PD-L2 on tumor cells are important contributors to tumor cells evading host immunity. PD-1/PD-L1 pathway controls the induction and maintenance of immune tolerance within the tumor microenvironment. The activity of PD-1 and its ligands PD-L1 or PD-L2 are responsible for T cell activation, proliferation, and cytotoxic secretion in cancer to degenerating anti-tumor immune responses (Han et al., Am J Cancer Res; 10(3):727-742 (2020)). By eliminating CAFs, TLY012 opens the tumor microenvironment susceptible to host's anti-tumor immune reactions. Systemic DR5 agonist (TLY012) combined with established, emerging immunotherapy (e.g., checkpoint inhibitor) can gain entry of the delivery of drugs and immune cells to tumors while restoring immune responses in the tumor microenvironment, thus demonstrate synergy in Hepatocellular carcinoma (HCC), Colorectal cancer, or Pancreatic ductal adenocarcinoma (PDAC).

Materials and Methods

Total RNA from the cultured cells was extracted with Purelink RNA kit (Thermo Fisher Scientific, Waltham, Mass.) according to the manufacturer's instructions. The RNA concentration was measured spectrophotometrically using NanoDrop 2000 (Thermo Fisher Scientific). 1-2 μg of total RNA was reverse-transcribed to cDNA using the High-Capacity cDNA Reverse Transcription System (Thermo Fisher Scientific). Comparative quantitative RT-PCR (qPCR) was performed in triplicate for each sample using fast SYBR Green Master Mix (Thermo Fisher Scientific) and StepOnePlus Real-Time PCR System (Thermo Fisher Scientific). The expression levels of target genes were normalized to the expression of 18s and calculated based on the comparative cycle threshold Ct method ($2^{-\Delta\Delta Ct}$). The sequences for the primers are shown in Table 7.

TABLE 7

Primer sequence used for qPCR.

| Target Gene | Forward (5'-3') | SEQ ID NO: | Reverse (5'-3') | SEQ ID NO: |
|---|---|---|---|---|
| Dr4 | GGG AAG AAG ATT CTC CTG AGA TGT G | 41 | ACA TTG TCC TCA GCC CCA GGT CG | 42 |
| Dr5 | AAG ACC CTT GTG CTC GTT G | 43 | AGG TGG ACA CAA TCC CTC TG | 44 |

TABLE 7-continued

Primer sequence used for qPCR.

| Target Gene | Forward (5'-3') | SEQ ID NO: | Reverse (5'-3') | SEQ ID NO: |
|---|---|---|---|---|
| Acta2 | CCA GAG CCA TTG TCA CAC AC | 45 | CAG CCA AGC ACT GTC AGG | 46 |
| Tgf-b | CTT CCA GCC GAG GTC CTT | 47 | CCC TGG ACA CCA ACT ATT GC | 48 |
| Col1a2 | AGC AGG TCC TTG GAA ACC TT | 49 | GAA AAG GAG TTG GAC TTG GC | 50 |
| PD-L1 | AAA TGG AAC CTG GCG AAA GC | 51 | GAT GAG CCC CTC AGG CAT TT | 52 |
| PD-L2 | GTC TTG GGA GCC AGG GTG AC | 53 | TGA AAA GTG CAA ATG GCA AGC | 54 |
| 18sRNA | CTA CCA CAT CCA AGG AAG CA | 55 | TTT TTC GTC ACT ACC TCC CCG | 56 |

Results

Figure 13A:
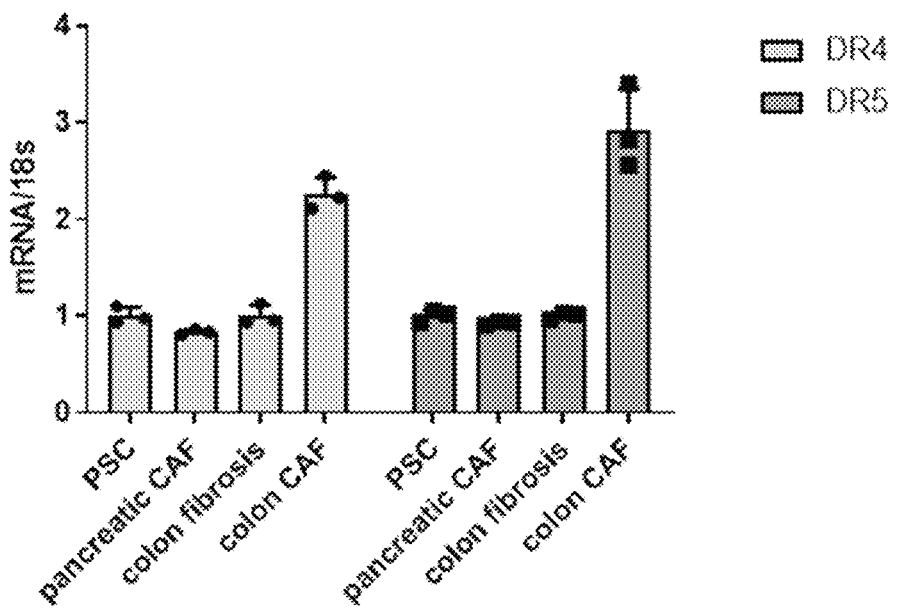
FIGS. 13A-13C are bar graphs showing the mRNA expression levels of Dr4, DR5, Acta2, TGF-b, Col1a2, PD-L1, and PD-L2 in the pancreatic and colon CAFs compared to normal (quiescent) PSC.
Figure 13B:
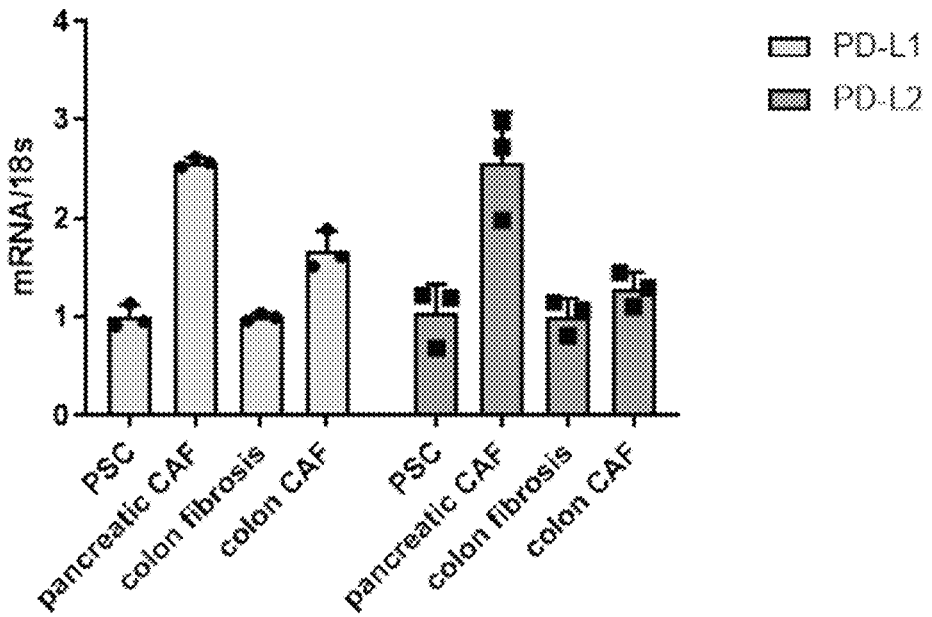
Figure 13C:
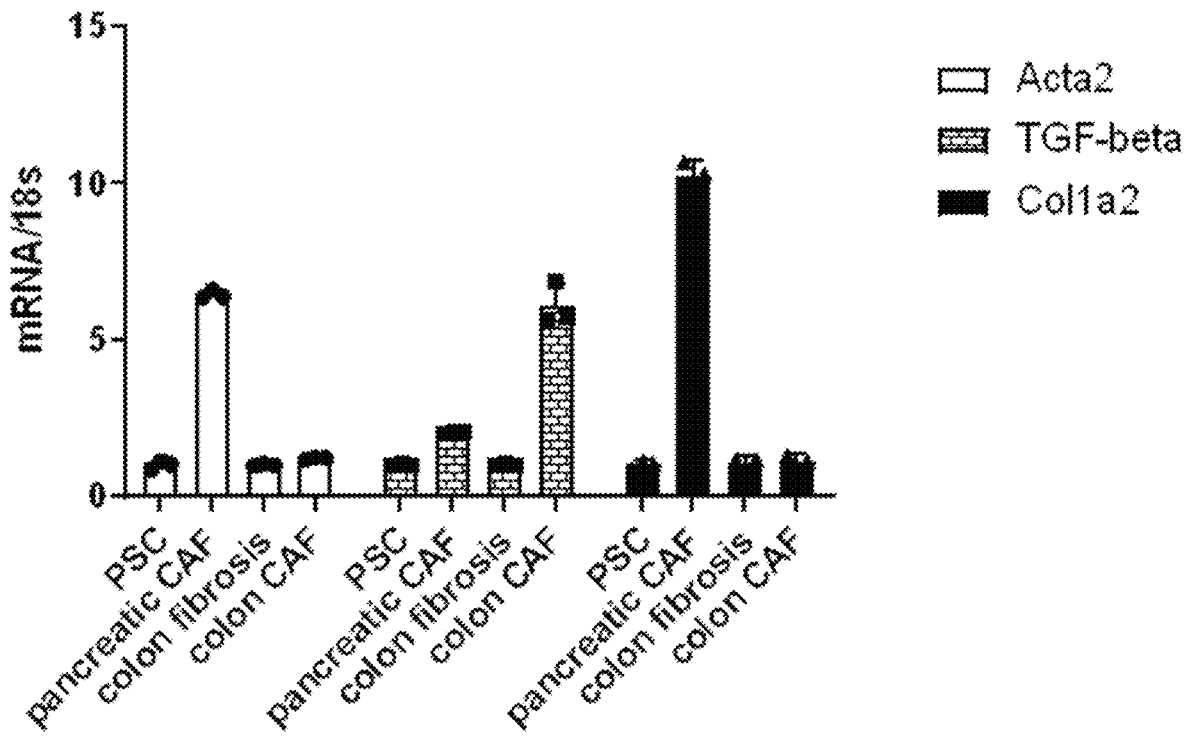

FIGS. 13A-13C show relative expression of mRNA for DR4 or DR5 (FIG. 13A), for PD-L1 or PD-L2 (FIG. 13B), or for Acta2, TGF-beta, or Col1a2 (FIG. 13C). FIGS. 13B and 13C show that CAFs highly express the fibrogenic markers and PD-L1/2.

This study showed the expression levels of mRNA Dr4, Dr5, Acta2, Tgf-b, Col1a2, PD-L1, and PD-L2 in both pancreatic CAF and colon CAF compared to normal cells, quiescent PSC, or Conlon fibroblasts. Both pancreatic CAF and colon CAF showed high levels of mRNA PD-L1 or PD-L2. Colon CAF shows high levels of Dr4/5 compared to normal cells and the pancreatic CAF shows significantly high levels of mRNA fibrogenic marker of Acta2, Tgf-b, Col1a2. Taken together, these data show that removal of fibrosis is an effective strategy to treat cancer.

Example 14. TLY012 Reduced the Levels of Fibrosis and Tumor Volume in Orthotopic Xenografts of Mouse KPC Cells Materials and Methods The Procedures of Inoculating KPC in the Pancreas of B6.129 Mice To generate the solid tumor, $10^7$ of mouse pancreatic ductal adenocarcinoma UN-KPC-960-luc2 cells suspended in 100 µl PBS were inoculated into flank of syngeneic B6.129 mice. The KPC tumors from the donor mice were excised under sterile conditions once the tumor was grown up to 8-10 mm$^3$ in diameter. The donor tumors were cut into 1-1.5 mm$^3$ pieces using surgical blade.

For the orthotopic xenografted tumors in pancreas, a laparotomy via left flank incision was performed to expose the pancreatic head and donor tumor pieces were inserted into the pancreas of recipient B6.129 mice (n=7/group) followed by closing in two layers with 5-0 absorbable sutures. Two weeks after the tumor transplantation, mice were injected with TLY012 via intraperitoneal route (10 mg/kg, every other day) and/or anti-PD-L1 (B7-H1, anti-mouse PD-L1, 2.5 mg/kg, twice of a week) for 2 weeks. Transplanted animals were imaged once a week for 5 weeks. Bioluminescent images using IVIS were acquired 10-15 minutes after intraperitoneal administration of D-Luciferin (150 mg/kg) (GOLDBIO, St. Louis, Mo., USA).

For tumor volume studies, orthotopic xenografted tumors were generated in pancreas. A laparotomy via left flank incision was performed to expose the pancreatic head and 5×10$^6$ of UN-KPC-960 cells were transplanted into the pancreas of recipient B6.129 mice (n=5/group) followed by closing in two layers with 5-0 absorbable sutures. four weeks after the transplantation, mice were injected with TLY012 via intraperitoneal route (10 mg/kg, every other day) or saline for 2 weeks. Then excised tumors were studied by: a) captured image and tumor volume of ½ab$^2$, and b) measured collagen and α-SMA positive area after TLY012 treatment using Sirius red and anti-α-SMA staining Double Immunofluorescence Staining Paraffin sectioned KPC tumor samples were used for immunofluorescence staining (IF) stain with α-SMA and either CD4 or CD8. Tissues were deparaffinized, hydrated, and heated in citrate buffer (Thermo Fisher Scientific) by microwave for antigen retrieval. Slides were washed, treated with blocking solution (3% of normal horse serum, Vectastain ABC System, Vector Labs, Burlingame, Calif.), and primary antibodies, rabbit anti-CD4 antibody (Abcam, ab183685) or rabbit anti-CD8 antibody (Abcam, ab217344) were applied with mouse anti-α-SMA antibody. Tissues were incubated overnight at 4° C., washed and anti-rabbit IgG conjugated with Alexa fluor 488 and anti-mouse IgG conjugated with Alexa fluor 633 (Thermo Fisher Scientific) were applied and incubated at room temperature. After washing the slides, samples were mounted with Fluorescence Mounting Medium with DAPI and captured under Axiovert microscope (Carl Zeiss Microscopy, LLC. Thornwood, N.Y.).

Histologic Study and Immunohistochemistry

The excised tumors were immediately fixed in 10% buffered formalin, embedded in paraffin, and cut at 4 µm thickness. The sections were then stained for Masson's Trichrome or Sirius-Red staining for determining the collagen deposition. Stained tissues were imaged under a light microscope (Nikon Eclipse E600 connected with Nikon DS-Fi2 camera, Nikon USA). Stained pancreatic tissues were randomly selected 10 photos from individual mice, and the positively stained area was quantified using Image J software (NIH, Bethesda, Md.).

Results

Figure 14:
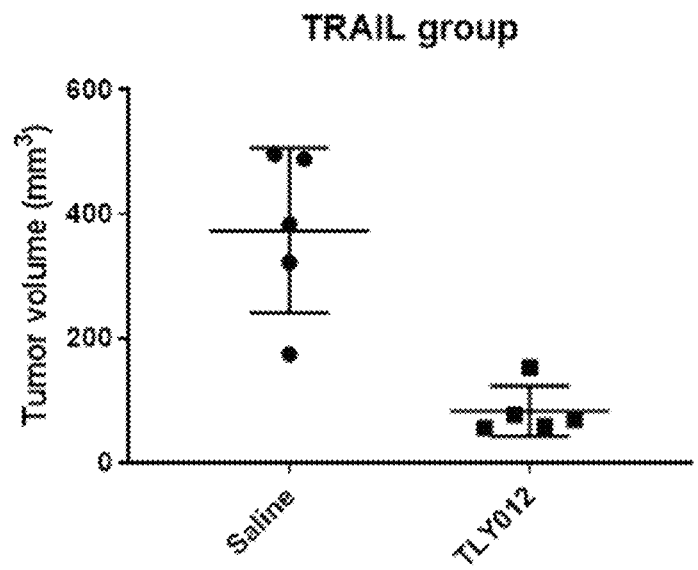
FIG. 14 is a graph showing change in tumor volume ($mm^3$) of tumors obtained from orthotopic pancreatic xenografts of KPC cell in mice treated with saline or TLY012.

TLY012 reduced the levels of fibrosis and tumor volume in orthotopic xenografts of mouse KPC cells (FIG. 14). The data showed that only TLY012 reduced the tumor volume compared to the saline-treated group. The tissue samples of the xenografted tumor showed high levels of collagen deposition and α-SMA positive area but TLY012 treatment decreased the levels of collagen as assessed by immunohistochemistry.

Treatment of TLY012 promoted the migration of cytotoxic T cells to the tumor site in orthotopic xenografts of mouse KPC cells. CD4+ and CD8+ cells were detected in tumor tissues. This data showed that cytotoxic T cells including CD8 and CD4 cells colocalized with α-SMA cells in TLY012 samples of tumor tissue compared to Saline treat specimen. Such a strategy reduced fibrosis and disrupted stromal barriers in PDAC tumors. Finally, TLY012 enhanced cytotoxic T cell infiltration to the tumor site.

Figure 15A:
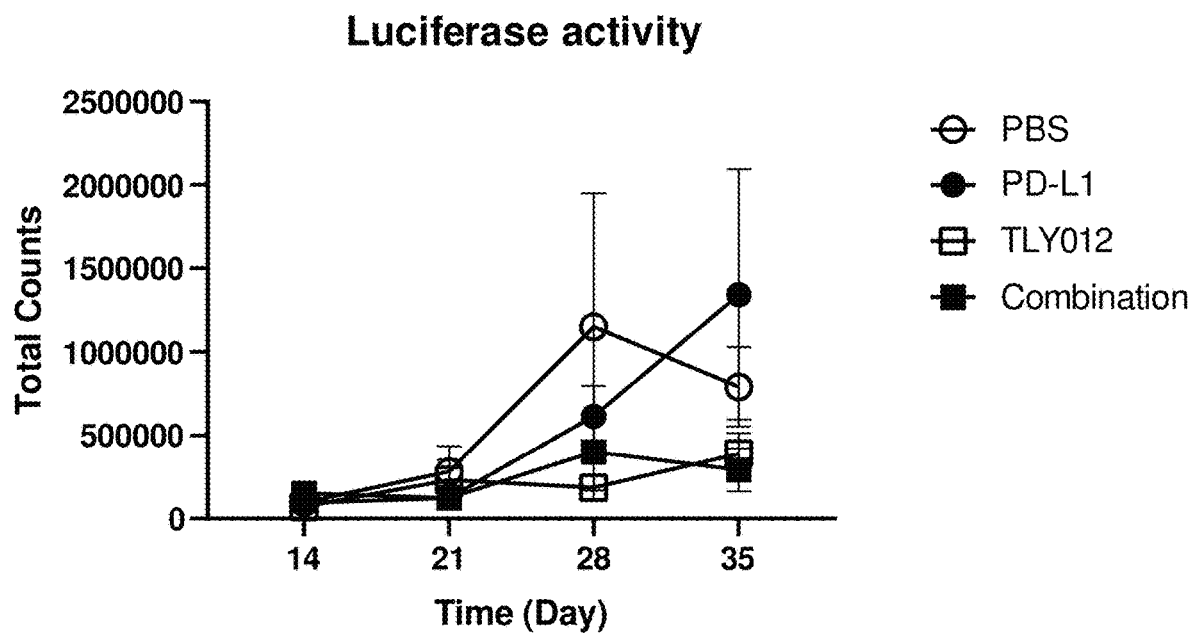
FIG. 15A is a line graph of bioluminescence activity (Total Counts) over time (days) obtained from tumors of mice with orthotopic xenografts of mouse KPC cells and treated with PBS, anti-PD-L1 antibody (B7-H1, anti-mouse PD-L1), TLY012, or with the combination of anti-PD-L1 antibody and TLY012.
Figure 15B:
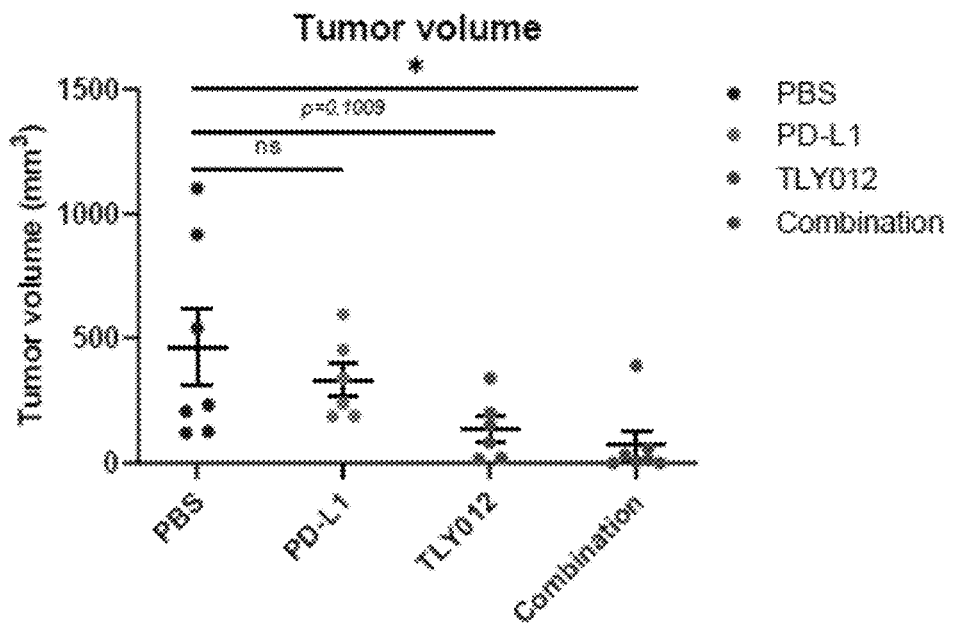
FIG. 15B is a graph showing tumor volume ($mm^3$) of tumors obtained from mice with orthotopic xenografts of mouse KPC cells and treated with PBS, anti-PD-L1 antibody, TLY012, or with the combination of anti-PD-L1 antibody and TLY012.
Figure 15C:
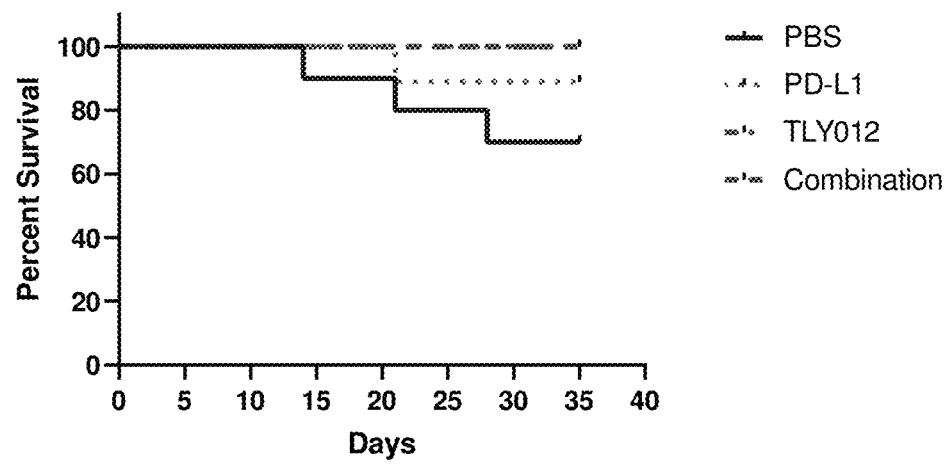
FIG. 15C is a survival curve showing percent survival over days of mice with orthotopic xenografts of mouse KPC cells and treated with PBS, anti-PD-L1 antibody, TLY012, or with the combination of anti-PD-L1 antibody and TLY012.

The combination treatment of TLY012 and anti-PD-L1 reduced the luciferase activity in the tumors, reduced tumor volume, and increased percent survival in mice with orthotopic xenografts of mouse KPC cells (FIGS. 15A-15C). The results are also show in Tables 8-10.

TABLE 8

Bioluminescence activity (Total Counts) over time (days) obtained from tumors of mice with orthotopic xenografts of mouse KPC cells and treated with PBS, anti-PD-L1 antibody, TLY012, or with the combination of anti-PD-L1 antibody and TLY012

| Day | PBS Mean | PBS S.E.M. | Anti-PD-L1 Mean | Anti-PD-L1 S.E.M. |
|---|---|---|---|---|
| 14 | 96750 | 35252.69 | 94771.4286 | 35887.57 |
| 21 | 269275 | 153229 | 123900 | 64283.08 |
| 28 | 1150814.29 | 799024.8 | 615800 | 165854.2 |
| 35 | 791571.429 | 239455.4 | 1343671.43 | 748171.4 |

| Day | TLY012 Mean | TLY012 S.E.M. | Combination Mean | Combination S.E.M. |
|---|---|---|---|---|
| 14 | 72300 | 20122.91 | 150585.714 | 63546.97 |
| 21 | 233157.143 | 121882 | 124585.714 | 71989.12 |
| 28 | 185128.571 | 72941.85 | 401900 | 215512.1 |
| 35 | 390357.143 | 123196.4 | 292400 | 129211.9 |

TABLE 9 showing tumor volume (mm3) of tumors obtained from mice with orthotopic xenografts of mouse KPC cells and treated with PBS, anti-PD-L1 antibody, TLY012, or with the combination of anti-PD-L1 antibody and TLY012.

| Group | Average | S.E.M. |
|---|---|---|
| PBS | 463.8599 | 152.148313 |
| Anti-PD-L1 | 332.9315 | 62.0521868 |
| TLY012 | 135.0695 | 46.6929957 |
| Combination | 71.81133 | 53.4457007 |

TABLE 10

Percent survival over days of mice with orthotopic xenografts of mouse KPC cells and treated with PBS, anti-PD-L1 antibody, TLY012, or with the combination of anti-PD-L1 antibody and TLY012.

| Day | PBS | Anti-PD-L1 | TLY012 | Combination |
|---|---|---|---|---|
| 0 | 100 | 100 | 100 | 100 |
| 14 | 90 | | | |
| 21 | 80 | 88.889 | | |
| 28 | 70 | | | |
| 35 | 70 | 88.899 | 100 | 100 |

The intensity of bioluminescence was significantly decreased in the tumors as assessed by IVIS® Spectrum in vivo imaging system from the samples treated with TLY012 or PD-L1 combinational treatment (FIG. 15A). This confirmed that PD-L1 and TLY012 combined treatment showed the most effective efficacy among the treatment group (FIG. 15B). Also, it was found that the combination treatment increased the survival rate of the animals (FIG. 15C).

Figure 16:
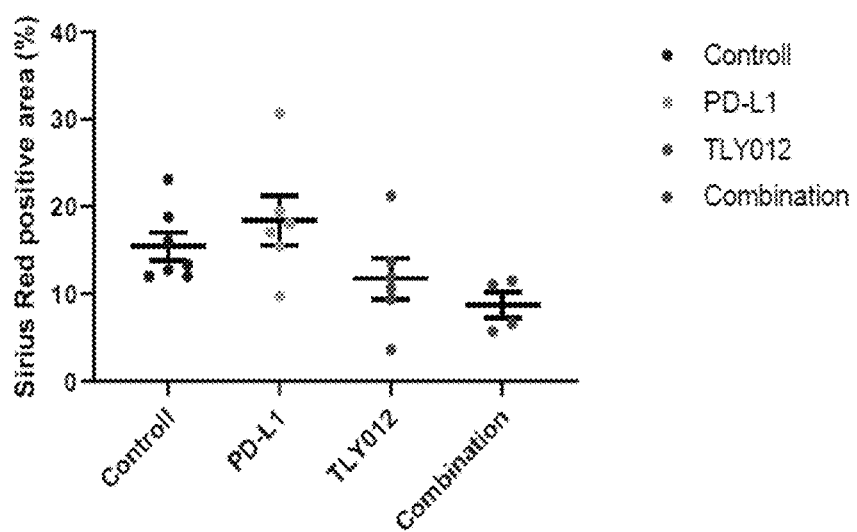
FIG. 16 is a graph showing Sirius Red positive area (%) in tissues of mice with orthotopic xenografts of mouse KPC cells and treated with PBS, anti-PD-L1 antibody, TLY012, or with the combination of anti-PD-L1 antibody and TLY012.

The combination of TLY012 and anti-PD-L1 reduced the levels of collagen deposition as determined from captured image of Sirius Red staining for collagen positive area (FIG. 16). This confirmed that tissue samples of the xenografted tumors showed high levels of collagen deposition in the control mice but the combination treatment of PD-L1 and TLY012 reduced the collagen positive area (Sirius Red) compared to other groups (FIG. 16).

The current knowledge on tumor microenvironment, focusing on T cells, cancer associated fibroblasts and extracellular matrix has been discussed (Di Modugno et al., *Journal of Experimental and Clinical Cancer Research*, 38(117) (2019)). A deep analysis of the complexity of the tumor microenvironment further advances the field and hopefully identifies more effective combined immunotherapeutic strategies.

TRAIL signaling interacting with CAF and immune cells plays a potential anti-fibrotic role in the fibrosis-associated tumor microenvironment.

Activated PSC are the major source of cancer-associated fibroblasts (CAF) and desmoplasia, which are known to contribute to the onset and progression of tumors with potent immunosuppressive properties. Importantly, PDAC, with excessive tumor microenvironment, is highly resistant to conventional anticancer drugs because drug delivery is difficult due to the penetration.

The combination TLY012 with anti-PD-L1 immunotherapy showed the best results and may be the main treatment including PD-1, PD-L1, CTLA-4, IDO. The blockade of immune checkpoints is the most promising approach to activating therapeutic antitumor immunotherapy so far. The programmed cell death-1 (PD-1) is an essential immune checkpoint of T-lymphocytes. However, PD-L1 from tumor cell binds to PD-1 inhibiting the antitumor ability of T-lymphocytes by reducing T cell activity and proliferation, known as a "don't eat me signal". One of the major contributing factors to this poor prognosis of immunotherapy is desmoplasia, the excessive proliferation of fibrotic tissue. The desmoplastic reaction induces physiological and biological signaling that promotes tumor cell proliferation and drug resistance.

It is shown here that TLY012 has anti-fibrogenic function and targets the fibrogenic tumors with cancer associated fibroblasts, which, without therapy, are resistant to immunotherapy because of the fibrotic cell barrier.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A recombinant fusion polypeptide comprising a first amino acid sequence comprising an amino acid sequence having at least 90% identity to any one of SEQ ID NOs: 4-8,
   wherein at least one of the amino acids at positions 14, 17, and 26 of SEQ ID NOs: 4-8 is selected from the group consisting of Valine (V), Glutamic acid (E), and/or Glutamine (Q), and wherein immunogenic epitopes of Isoleucine at position 17 and Lysine at position 26 are not present together in the first amino acid sequence, and
   a second amino acid sequence comprising a tumor necrosis factor-related apoptosis ligand (TRAIL) domain.

2. The recombinant fusion polypeptide of claim 1, wherein the second amino acid sequence comprises an amino acid sequence of any one of SEQ ID NOs: 9-26.

3. The recombinant fusion protein of claim 1, wherein the first amino acid comprises SEQ ID NO:4 and the second amino acid comprises SEQ ID NO:15.

4. The recombinant fusion polypeptide of claim 1, wherein the polypeptide further comprises a linker between the first amino acid and the second amino acid.

5. The recombinant fusion polypeptide of claim 4, wherein the linker comprises an amino acid linker.

6. The recombinant fusion polypeptide of claim 1, wherein the first amino acid and the second sequence are linked with a linker selected from the group consisting of amino acids Asp (D), Gly (G), DG, KGSG (SEQ ID NO:27), GSG, SG, and RGSG (SEQ ID NO:28).

7. The recombinant fusion polypeptide of claim 1, wherein the fusion polypeptide comprises the amino acid sequence of SEQ ID NO:30 SEQ ID NO: 31 or SEQ ID NO: 32.

8. The recombinant fusion polypeptide of claim 1, wherein two or more of the polypeptides are in a form of dimers, trimers, tetramers, or multimers.

9. The recombinant fusion polypeptide of claim 1, having a solubility in physiological buffer and pH at between about 0.2 mg/ml and 100 mg/ml.

10. The recombinant fusion polypeptide of claim 1, wherein the polypeptide is an inhibitory polypeptide having half maximal inhibitory concentration (IC50) in vitro between about 0.001 nM and about 0.1 nM.

11. The recombinant fusion polypeptide of claim 1, having a half-life in vivo between about 1 hour and 24 hours.

12. The recombinant fusion polypeptide of claim 1, having a substantially lower immunogenicity in a mammalian host, relative to immunogenicity of a corresponding polypeptide with a first amino acid having at least 90% identity to any one of SEQ ID NOs: 4-8 and without at least one Valine (V), Glutamic acid (E), and/or Glutamine (Q) at positions 14, 17, or 26.

13. A conjugate comprising the recombinant fusion polypeptide of claim 1 and a half-life extending molecule.

14. The conjugate of claim 13, wherein the half-life extending molecule comprises polyethylene glycol or a derivative thereof.

15. The conjugate of claim 13, wherein the half-life extending molecule comprises polyethylene glycol or a derivative thereof having a molecular weight between about 5 000 Da and about 100 000 Da.

16. The conjugate of claim 13, having solubility of up to about 50 mg/ml in presence of a physiological concentration of salts.

17. The conjugate of claim 13, having a half-life in vivo between about 20 hours and about 50 hours in non-human primates.

18. The conjugate of claim 13, having an IC50 in vitro between about 0.01 nM and about 1 nM when tested on activated hepatic stellate cells (HSCs).

19. The conjugate of claim 13, wherein two or more freeze-thaw cycles of the recombinant fusion polypeptide do not substantially reduce the conjugate's solubility and activity.

20. The conjugate of claim 13, having a substantially lower immunogenicity in a mammalian host relative to immunogenicity of a corresponding conjugate with a first amino acid having at least 90% identity to any one of SEQ ID NOs: 4-8 and without at least one Valine (V), Glutamic acid (E), and/or Glutamine (Q) at positions 14, 17, or 26.

21. A method of treating a proliferative, autoimmune, or fibrotic disease, the method comprising administering to a subject in need thereof an effective amount of the recombinant fusion polypeptide of claim 1, or an effective amount of the conjugate of claim 13.

22. The method of claim 21, wherein the effective amount of the fusion polypeptide or the effective amount of the conjugate is between about 0.001 mg/kg and about 50 mg/kg.

23. The method of claim 21 wherein the fusion polypeptide or the conjugate is the first active agent and the method further comprises administering a second active agent.

24. The method of claim 21, wherein treating a proliferative disease comprises treating a proliferative disease with solid tumors.

25. The method of claim 21 comprising inducing apoptosis in cancer-associated fibroblasts.

26. The method of claim 21 comprising reducing the volume of tumors in proliferative disease.

27. The method of claim 21 comprising administering a second active agent, wherein the second active agent is a chemotherapeutic agent.

28. The method of claim 21 comprising treating with a second active agent, wherein the second active agent is a chemotherapeutic agent is a DNA topoisomerase I and II inhibitor and/or an immune checkpoint inhibitor (ICI).

29. The method of claim 21 comprising treating with a second active agent, wherein the second active agent is selected from the group consisting of doxorubicin, etoposide, camptothecin, irinotecan, cisplatin, oxaliplatin, docetaxel, cyclophosphamide, 5-fluorouracil, carboplatin, mechlorethamine, sorafenib, chlorambucil, vincristine, vinblastine, vinorelbine, vindesine, taxol and derivatives thereof, topotecan, amsacrine, etoposide phosphate, teniposide, epipodophyllotoxins, trastuzumab, cetuximab, rituximab, bevacizumab, nivolumab, pembrolizumab, atezolizumab, avelumab, durvalumab, cemiplimab, pidilizumab, vopratelimab, danvatirsen, cetrelimab, and ipilimumab.

30. The conjugate of claim 18, having an IC50 in vitro between about 0.01 nM and about 0.5 nM when tested on activated hepatic stellate cells (HSCs).

31. A recombinant fusion polypeptide comprising a first amino acid sequence selected from SEQ ID NOs: 4-8 and a second amino acid sequence comprising a TRAIL domain.

32. The recombinant fusion polypeptide of claim 31, further comprising a half-life extending molecule.

33. The recombinant fusion polypeptide of claim 32, wherein the half-life extending molecule comprises polyethylene glycol or a derivative thereof.

34. The recombinant fusion polypeptide of claim 32, wherein the half-life extending molecule comprises polyethylene glycol or a derivative thereof having a molecular weight between about 5,000 Da and about 100,000 Da.

35. The method of claim 25, comprising treating liver cancer, pancreatic cancer, or colon cancer to induce apoptosis in cancer associated fibroblasts.

* * * * *

UNITED STATES PATENT AND TRADEMARK OFFICE
CERTIFICATE OF CORRECTION

PATENT NO. : 11,767,353 B2
APPLICATION NO. : 17/223283
DATED : September 26, 2023
INVENTOR(S) : Alex Sokoloff et al.

Page 1 of 1

It is certified that error appears in the above-identified patent and that said Letters Patent is hereby corrected as shown below:

In the Specification

Column 21, Line 46, replace "acylic" with --acrylic--.

In the Claims

Claim 3, Column 103, Lines 18-19, replace "amino acid" with --amino acid sequence--.

Claim 4, Column 103, Line 22, replace "amino acid" with --amino acid sequence--.

Claim 6, Column 103, Line 26, replace "amino acid" with --amino acid sequence--.

Claim 6, Column 103, Line 26, replace "second sequence" with --second amino acid sequence--.

Claim 7, Column 103, Line 32, insert a --,-- after "SEQ ID NO:30".

Claim 12, Column 103, Line 49, replace "amino acid" with --amino acid sequence--.

Claim 20, Column 104, Line 11, replace "amino acid" with --amino acid sequence--.

Signed and Sealed this
Thirtieth Day of September, 2025

John A. Squires
*Director of the United States Patent and Trademark Office*